United States Patent [19]
Paoletti et al.

[11] Patent Number: 5,989,561
[45] Date of Patent: Nov. 23, 1999

[54] RECOMBINANT POXVIRUS-CALICIVIRUS RABBIT HEMORRHAGIC DISEASE VIRUS (RHDV) COMPOSITIONS AND USES

[75] Inventors: Enzo Paoletti, Delmar; Laurent Fischer, Albany, both of N.Y.; Francois-Xavier Legros, Oullins, France

[73] Assignee: Virogenetics Corporation, Troy, N.Y.

[21] Appl. No.: 08/471,025

[22] Filed: Jun. 6, 1995

Related U.S. Application Data

[63] Continuation-in-part of application No. 08/105,483, Aug. 13, 1993, Pat. No. 5,494,807, and application No. 08/036,217, Mar. 24, 1993, Pat. No. 5,364,773, which is a continuation of application No. 07/666,056, Mar. 7, 1991, abandoned, said application No. 08/105,483, is a continuation of application No. 07/847,951, Mar. 6, 1992, abandoned, which is a continuation-in-part of application No. 07/713,967, Jun. 11, 1991, abandoned, which is a continuation-in-part of application No. 07/666,056.

[51] Int. Cl.$^6$ .................. A61K 39/285; C12N 15/80; C12N 7/01
[52] U.S. Cl. .................. 424/199.1; 424/204.1; 435/235.1; 435/320.1; 435/325; 435/69.1; 536/24.31; 536/24.33; 536/23.72
[58] Field of Search ............... 424/199.1, 204.1; 435/235.1, 320.1, 325, 69.1; 536/24.31, 23.72, 24.33

[56] References Cited

U.S. PATENT DOCUMENTS 5,021,347  6/1991  Yasui et al. ............... 435/235
5,494,807  2/1996  Paoletti .................... 435/69.3

FOREIGN PATENT DOCUMENTS 9215672  9/1992  WIPO .

OTHER PUBLICATIONS

Guiver et al. 1992, J. of Virology, vol. 73, pp. 2429–2433.
Buller et al. 1985, Nature, vol. 317 (6040), pp. 813–815.
Meyers et al. 1991, Virology, vol. 184, pp. 664–676.
Tartajlia et al, 1992, Virol., vol. 188, pp. 217–232.
Boga et al, 1994, J. Gen. Virol., vol. 75, pp. 2409–2413.
Laurent et al, 1994, J. Virol., pp. 6794–6798.
Negesha et al, 1995, Arch. Virol., vol. 140, pp. 1095–1108.

*Primary Examiner*—Mary E. Mosher
*Assistant Examiner*—Ali R. Salimi
*Attorney, Agent, or Firm*—McDonnell Boehnen Hulbert & Berghoff

[57] ABSTRACT

Attenuated recombinant viruses containing DNA encoding a calicivirus antigen such as a RHDV antigen, e.g., a capsid gene, as well as methods and compositions employing the viruses, expression products therefrom, and antibodies generated from the viruses or expression products, are disclosed and claimed. The recombinant viruses can be NYVAC or ALVAC recombinant viruses. The recombinant viruses and gene products therefrom and antibodies generated by the viruses and gene products have several preventive, therapeutic and diagnostic uses. The DNA from the viruses can be used for probes or for primers.

21 Claims, 20 Drawing Sheets

```
   1 tgaatgtiaa atgnatact ttggatgaag ctataaatat gcattggaaa aataatccat
  61 ttaaagaaag gattcaaata ctacaaaacc taagcgataa tatgttaact aagcttattc
 121 ttaacgacgc tttaaatata cacaaataaa cataattttt gtataaccta acaaataact
 181 aaaacataaa aataataaaa ggaaatgtaa tatcgtaatt attttactca ggaatggggt
 241 taaatattta tatcacgtgt atatctatac tgttatcgta tactctttac aattactatt
 301 acgaatatgc aagagataat aagattacgt atttaagaga atcttgtcat gataattggg
 361 tacgacatag tgataaatgc tatttcgcat cgttacataa agtcagttgg aaagatggat
 421 ttgacagatg taacttaata ggtgcaaaaa tgttaaataa cagcattcta tcggaagata
 481 ggataccagt tatattatac aaaaatcact ggttggataa aacagattct gcaatattcg
 541 taaaagatga agattactgc gaatttgtaa actatgacaa taaaaagcca tttatctcaa
 601 cgacatcgtg taattcttcc atgttttatg tatgtgtttc agatattatg agattactat
 661 aaactttttg tatacttata ttccgtaaac tatattaatc atgaagaaaa tgaaaaagta
 721 tagaagctgt tcacgagcgg ttgttgaaaa caacaaaatt atacattcaa gatggcttac
 781 atatacgtct gtgaggctat catggataat gacaatgcat ctctaaatag gtttttggac
 841 aatggattcg accctaacac ggaatatggt actctacaat ctcctcttga aatggctgta
 901 atgttcaaga ataccgaggc tataaaaatc ttgatgaggt atggagctaa acctgtagtt
 961 actgaatgca caacttcttg tctgcatgat gcggtgttga gagacgacta caaaatagtg
1021 aaagatctgt tgaagaataa ctatgtaaac aatgttcttt acagcggagg ctttactcct
1081 ttgtgtttgg cagcttacct taacaaagtt aatttggtta aacttctatt ggctcattcg
1141 gcggatgtag atatttcaaa cacggatcgg ttaactcctc tacatatagc cgtatcaaat
1201 aaaaatttaa caatggttaa acttctattg aacaaaggtg ctgatactga cttgctggat
1261 aacatgggac gtactccttt aatgatcgct gtacaatctg gaaatattga aatatgtagc
1321 acactactta aaaaaaataa aatgtccaga actgggaaaa attgatcttg ccagctgtaa
1381 ttcatggtag aaaagaagtg ctcaggctac ttttcaacaa aggagcagat gtaaactaca
1441 tctttgaaag aaatggaaaa tcatatactg ttttggaatt gattaaagaa agttactctg
1501 agacacaaaa gaggtagctg aagtggtact ctcaaaatgc agaacgatga ctgcgaagca
1561 agaagtagag aaataacact ttatgacttt cttagttgta gaaaagatag agatataatg
1621 atggtcataa ataactctga tattgcaagt aaatgcaata ataagttaga tttatttaaa
1681 aggatagtta aaaatagaaa aaaagagtta atttgtaggg ttaaaataat acataagatc
1741 ttaaaattta taaatacgca taataataaa aatagattat acttattacc ttcagagata
1801 aaatttaaga tatttactta tttaacttat aaagatctaa aatgcataat ttctaaataa
1861 tgaaaaaaag tacatcatga gcaacgcgtt agtatatttt acaatggaga ttaacgctct
1921 ataccgttct atgtttattg attcagatga tgttttagaa aagaaagtta ttgaatatga
1981 aaactttaat gaagatgaag atgacgacga tgattattgt tgtaaatctg ttttagatga
2041 agaagatgac gcgctaaagt atactatggt tacaaagtat aagtctatac tactaatggc
2101 gacttgtgca agaaggtata gtatagtgaa aatgttgtta gattatgatt atgaaaaacc
2161 aaataaatca gatccatatc taaaggtatc tcctttgcac ataatttcat ctattcctag
2221 tttagaatac tttcattat atttgtttac agctgaagac gaaaaaaaata tatcgataat
2281 agaagattat gttaactctg ctaataagat gaaattgaat gagtctgtga taatagctat
2341 aatcagagaa gttctaaaag gaaataaaaa tctaactgat caggatataa aaacattggc
2401 tgatgaaatc aacaaggagg aactgaatat agctaaacta ttgttagata gaggggccaa
2461 agtaaattac aaggatgttt acgttcttc agctctccat agagctgcta ttggtaggaa
2521 acaggatatg ataaagctgt taatcgatca tggagctgat gtaaactctt taactattgc
2581 taaagataat cttattaaaa aaaataata tcacgtttag taatattaaa atatattaat
2641 aactctatta ctaataactc cagtggatat gaacataata cgaagtttat acattctcat
2701 caaaatctta ttgacatcaa gttagattgt gaaaatgaga ttatgaaatt aaggaataca
2761 aaaataggat gtaagaactt actagaatgt tttatcaata atgatatgaa tacagtatct
2821 agggctataa acaatgaaac gattaaaaat tataaaaatc atttccctat atataatacg
2881 ctcatagaaa aattcatttc tgaaagtata ctaagacacg aattattgga tggagttata
2941 aattcttttc aaggattcaa taataaattg ccttacgaga ttcagtacat tatactggag
3001 aatcttaata accatgaact aaaaaaaatt ttagataata tacattaaaa aggtaaatag
3061 atcatctgtt attataagca aagatgcttg ttgccaataa tatacaacag gtatttgttt
3121 ttatttttaa ctacatattt gatgttcatt ctctttatat agtatacaca gaaaattcat
3181 aatccactta gaatttctag ttatctag
```

FIG. 8

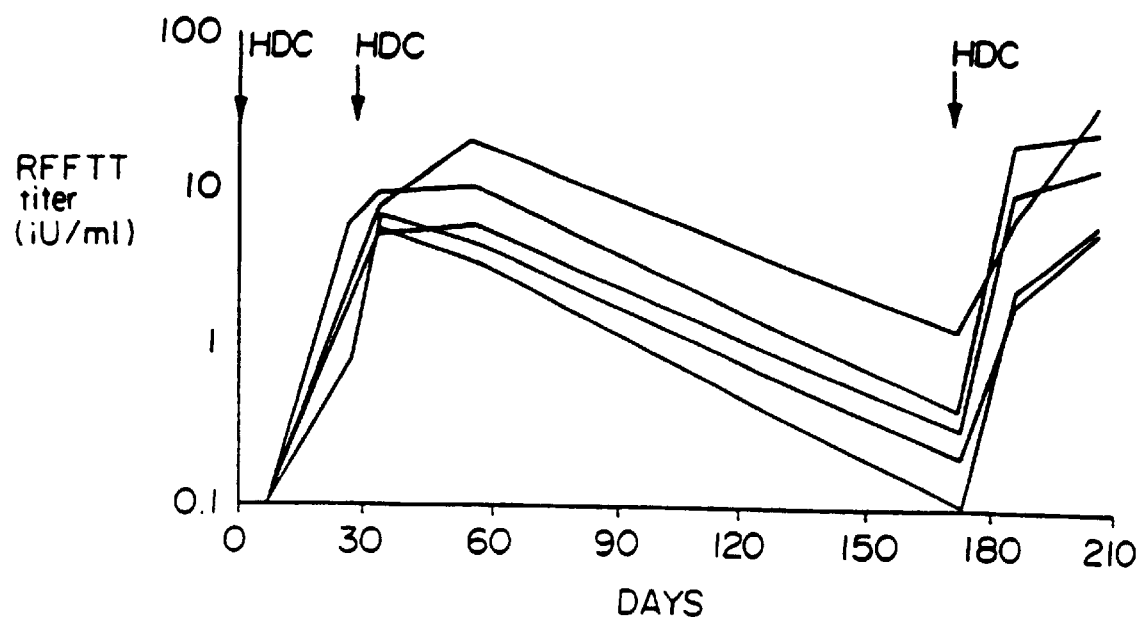
FIG. IIA
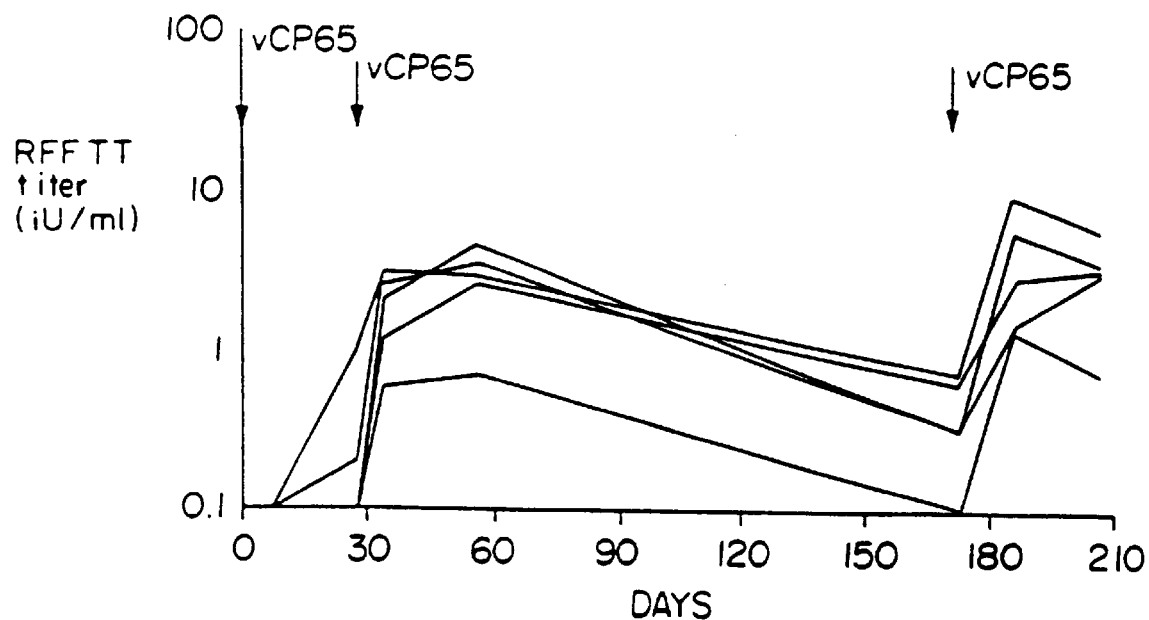
FIG. IIC

```
  1 ATG GAG GGC AAA GCC CGT GCA GCG CCG CAA GGC GAA GCA GCG GGC ACT GCC ACC ACA GCA
  1▶Met Glu Gly Lys Ala Arg Ala Ala Pro Gln Gly Glu Ala Ala Gly Thr Ala Thr Thr Ala

61 TCA GTT CCT GGA ACT ACG ACT GAT GGC ATG GAT CCT GGC GTT GTG GCC ACT ACC AGC GTG
 21▶Ser Val Pro Gly Thr Thr Thr Asp Gly Met Asp Pro Gly Val Val Ala Thr Thr Ser Val

121 ATC ACT GCA GAA AAT TCA TCC GCA TCG ATT GCA ACA GCA GGG ATT GGC GGA CCA CCC CAA
 41▶Ile Thr Ala Glu Asn Ser Ser Ala Ser Ile Ala Thr Ala Gly Ile Gly Gly Pro Pro Gln

181 CAG GTA GAC CAA CAA GAG ACA TGG AGA ACA AAT TTT TAT TAC AAT GAT GTT TTC ACT TGG
 61▶Gln Val Asp Gln Gln Glu Thr Trp Arg Thr Asn Phe Tyr Tyr Asn Asp Val Phe Thr Trp

241 TCA GTC GCG GAC GCC CCT GGC AGC ATA CTT TAC ACT GTC CAA CAT TCT CCA CAG TTT CGC
 81▶Ser Val Ala Asp Ala Pro Gly Ser Ile Leu Tyr Thr Val Gln His Ser Pro Gln Phe Arg

301 CCA TTC ACA GCC GTG CTG AGC CAG ATG TAC GCT GGC TGG GCT GGT GGC ATG CAG TGG
101▶Pro Phe Thr Ala Val Leu Ser Gln Met Tyr Ala Gly Trp Ala Gly Gly Met Gln Phe Arg

361 TTC ATA GTT GCC GGG TCA GGT GTG TTT GGT GGG CGA TTG GTC GCG GCT GTC ATA CCA CCA
121▶Phe Ile Val Ala Gly Ser Gly Val Phe Gly Gly Arg Leu Val Ala Ala Val Ile Pro Pro

421 GGC ATC GAA ATT GGA CCA GGG TTG GAG GTC AGG CAA TTT CCT CAT GTT CCT CAT GTC GAC GCC
141▶Gly Ile Glu Ile Gly Pro Gly Leu Glu Val Arg Gln Phe Pro His Val Val Ile Asp Ala

481 CGT TCA CTC GAA CCT GTT ACC ATC ACC ATG CCA GAC TTG CGT CCC AAC ATG TAC CAT CCA
161▶Arg Ser Leu Glu Pro Val Thr Ile Thr Met Pro Asp Leu Arg Pro Asn Met Tyr His Pro
```

FIG. 12A-1

```
541  ACT GGT GAC CCT GGT CTT GTA CCC ACA TTA GTC CTC AGT GTT TAC AAC AAC CTC ATC AAC
181▶ Thr Gly Asp Pro Gly Leu Val Pro Thr Leu Val Leu Ser Val Tyr Asn Asn Leu Ile Asn

601  CCG TTT GGT GGG TCC ACC AGC GCA ATC CAG GTG ACA GAA ACA ACG CCA AGT GAA GAC
201▶ Pro Phe Gly Gly Ser Thr Ser Ala Ile Gln Val Thr Glu Thr Thr Pro Ser Glu Asp

661  TTT GAG TTC GTG ATG ATT CGA GCC CCC TCC AGT AAG ACT GTT GAC TCA ATT TCA CCC GCA
221▶ Phe Glu Phe Val Met Ile Arg Ala Pro Ser Ser Lys Thr Val Asp Ser Ile Ser Pro Ala

721  GGC CTC CTC ACG ACC CCA GTC CTC ACT CTC GTT GGT AAT GAC AAC AGG TGG AAC GGC CAA
241▶ Gly Leu Leu Thr Thr Pro Val Leu Thr Leu Val Gly Asn Asp Asn Arg Trp Asn Gly Gln

781  ATA GTG GGA CTG CAA CCA GTA CCT GGA GGG TTT TCT ACG TGC AAC AGG CAT TGG AAC TTG
261▶ Ile Val Gly Leu Gln Pro Val Pro Gly Gly Phe Ser Thr Cys Asn Arg His Trp Asn Leu

841  AAT GGC AGC ACA TAT GGC TGG TCA AGC TTT CGG CCT TTT GCC GAC ATT GAC CAT CGA AGA GGC
281▶ Asn Gly Ser Thr Tyr Gly Trp Ser Ser Pro Arg Phe Ala Asp Ile Asp His Arg Arg Gly

901  AGT GCA AGT TAC TCT GGG AAC AAC GCA ACT AAC TCC CAG GTT GCA CCA GAC CAT TGG TAT GCC AAT GCT
301▶ Ser Ala Ser Tyr Ser Gly Asn Asn Ala Thr Asn Ser Gln Val Ala Pro Asp His Trp Tyr Ala Asn Ala

961  GGG TCT GCA ATC GAC GAT AAC CCC ATC TCC CAG GTT CAG CCA GAC ATG TCG
321▶ Gly Ser Ala Ile Asp Asp Asn Pro Ile Ser Gln Val Gln Pro Asp Met Ser

1021 TTC GTG CCC TTT AAC GGC CCT GGC ATT CCA GGC GCG GGG TGG GGA TTT GGT GCA ATC
341▶ Phe Val Pro Phe Asn Gly Pro Gly Ile Pro Gly Ala Ala Gly Trp Val Gly Phe Gly Ala Ile

1081 TGG AAC AGT AAC AGC GGT GCC CCC AAC GTT ACG ACT GTG CAG GCC TAT GAG TTA GGT TTT
361▶ Trp Asn Ser Asn Ser Gly Ala Pro Asn Val Thr Thr Val Gln Ala Tyr Glu Leu Gly Phe
```

FIG. 12A-2

```
1141 GCC ACT GGG GCA CCA GGC AAC CTC CAG CCC ACC AAC ACT TCA GGT GCA CAG ACT GTC
 381▸Ala Thr Gly Ala Pro Gly Asn Leu Gln Pro Thr Asn Thr Ser Gly Ala Gln Thr Val

1201 GCC AAG TCC ATT TAT GCC GTG ACT GTG CAA AAC GCC ACA GCC GGA TTG TTT GTG
 401▸Ala Lys Ser Ile Tyr Ala Val Val Thr Val Gln Asn Ala Thr Ala Gly Leu Phe Val

1261 ATG GCC TCG GGC GTT ATC TCC CCA AAT GCC AAC GCC ATC ACA TAC ACG CCC CAA CCA
 421▸Met Ala Ser Gly Val Ile Ser Pro Asn Ala Asn Ala Ile Thr Tyr Thr Pro Gln Pro

1321 GAC AGA ATT GTA ACC ACA CCC GGC ACT CCT GCC GCA CCT GTG GGT AAG AAC ACA CCC
 441▸Asp Arg Ile Val Thr Thr Pro Gly Thr Pro Ala Ala Pro Val Gly Lys Asn Thr Pro

1381 ATC ATG TTC GCG TCT GTC GTT AGG CGC ACC GGT GAC GTC AAC GCC ACA GCT GGG TCA GCT
 461▸Ile Met Phe Ala Ser Val Val Arg Arg Thr Gly Asp Val Asn Ala Thr Ala Gly Ser Ala

1441 AAC GGG ACC CAG TAC GGT TCA GCA CTT ATG CCC ACA CTG CCA GTG TGG CAG TTA ACC TTT GCA
 481▸Asn Gly Thr Gln Tyr Gly Ser Ala Leu Met Pro Thr Leu Pro Val Trp Gln Leu Thr Phe Ala

1501 AAC AAC TAC TCG TCA GCA CTT ATG GAG ATC GGT TTA AGT GTG GAC GGG TAT TAT GCA GGA ACA GGG GCC
 501▸Asn Asn Tyr Ser Ser Ala Leu Met Glu Ile Gly Leu Ser Val Asp Gly Tyr Tyr Ala Gly Thr Gly Ala

1561 TCT GGT TTC ATG GAG ATC GGT TTA AGT GTG GAC GGG TAT TAT GCA GGA ACA GGG GCC
 521▸Ser Gly Phe Met Glu Ile Gly Leu Ser Val Asp Gly Tyr Tyr Ala Gly Thr Gly Ala

1621 TCT ACC ACA CTC ATT GAC TTG ACT GAA CTC ATT GAC GTA CGC CCT GTG GGA CCC AGG CCG
 541▸Ser Thr Thr Leu Ile Asp Leu Thr Glu Leu Ile Asp Val Arg Pro Val Gly Pro Arg Pro

1681 TCC AAA AGC ACA CTG GGG GGA ACA GCC AAT GGC TTT TCT TAT GTC TGA ...
 561▸Ser Lys Ser Thr Leu Gly Gly Thr Ala Asn Gly Phe Ser Tyr Val ...
```

FIG. 12A-3

```
KpnI
GGTACCTTCATAATACAAGTTTGATTAAACTTAAGTTGTTCTAAAGTTCTTCCCTCCGAAGGTATAGAACAAAGTATTCTTC
TACATCCTTACTATTTATTGCAGCTTTAACAGCCTATCACGTATCCTATTTTTAGTATTGGTAGAATCGTTTTAGTTCTAAAG
TTAAATATTAGACATAATTGGCATATTGCTTATTCCTTGCATAGTTGAGTCTGTGTAGATCGTTTCAGTATATCACTGATTAATG
TACTACTGTTATGATGAAATATAGAATCGATATTGGCATTTAACTGTTTTGTTATACTAAGTCTAGATTTTAAATCTTCTAGTA
ATATGCTATTAATATAAAAGCTTCCACGTTTTGTATACATTTCTTTCCATATTAGTAGCTACTACTAAATGATTATCTTCTT
TCATATCTTGTAGATAAGATAGACTATCTTTATCTTTATTAGTAGAAAATACTTCTGGCCATACATCGTTAAATTTTTTGTTG
TTGTTAGATATAATATTAAATATCTAGAGGATCCTATTATTGTGGTAAAATGTTTATAGAGTAAAATGATCTGGCTATTAAAC
ATAGGCCAGTTACCATAGAATGCTGCTTCCCGTTACAGTGTTTACCATAACCATAGATCTGCCTGTATTGTTGATACATATAA
CAGCTGTAAATCCTAAAAATTCCTATCATAATTAATATTAGGTAATTCATTCCATGTGAAAGATAGACTAATTTTATAT
CCTTTACCTCCAAATAATTATTTACATCTCTTAAACAATCTATTTTAATATCATTAACTGGTATTTTATAATATCCAGAAAGT
TTGAAGGGGTTGATGGAATAAGTCTATTAACATCGTTAAGTAATTAGTTTGTAATAAATTATTAATATCATGAATCTTTATTATTATACCATAAG
TTAAATTTATATTTACTTTCTCATCATCTGACTTAGTTGTGTCTGAAAAATTAAAAGGTAATTCGTTG
AATGAAGCTGTATTTGCTGTATCATTTTTATCTAATTTGGAGATTTAGCAGTACTTACTTCATTAGAAGAAGAATCTGCCAGT
                                                                            HirdIII
TCCTGTCTATTACTGATATTTCGTTTCATTATTATTATGATTATTTTACTTTTTCAATTATATATACTCAAGCTT
```

FIG. 12B-1

HinfI
GAATCAAGCTTCATTTTTCGTAAGTAAGTATTTTATTTAATACTTTTTATTGTACTTATGTTAAATATAACTGATGATA

ACAAAATCCATTATGTATTATTTATAACTGTAATTCTTTAGCGTAGTTAGATGTCCAATCTCTCAAATACATCGGCTA

TCTTTTAGTGAGATTTGATCTATGCAGTTGAAACTTATGAACGCGTGATGATTAAAATGTGAACCGTCCAAATTGCAG

TCATTATATGAGCGTATCTATTATTCTACTATCATCATCTTTGAGTTATTAATATCATCTACTTTAGAATTGATAGGAAATA

TGAATACCTTTGTAGTAAATATCTATACTATCTACACCTAACTCATTAAGACTTTTGATAGTGGAGCTC
SacI

FIG. 12B-2

```
                             SEQUENCE LISTING (1) GENERAL INFORMATION:

(iii) NUMBER OF SEQUENCES: 47

(2) INFORMATION FOR SEQ ID NO:1:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:1:

TAATTAACTA GCTACCCGGG                                                     20

(2) INFORMATION FOR SEQ ID NO:2:

(i) SEQUENCE CHARACTERISTICS:
         (A) LENGTH: 28 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:2:

GTACATTAAT TGATCGATGG GCCCTTAA                                            28

(2) INFORMATION FOR SEQ ID NO:3:

(i) SEQUENCE CHARACTERISTICS:
         (A) LENGTH: 73 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:3:

AGCTTCCCGG GTAAGTAATA CGTCAAGGAG AAAACGAAAC GATCTGTAGT TAGCGGCCGC          60

CTAATTAACT AAT                                                            73

(2) INFORMATION FOR SEQ ID NO:4:

(i) SEQUENCE CHARACTERISTICS:
         (A) LENGTH: 69 base pairs
         (B) TYPE: nucleic acid
```

(C) STRANDEDNESS: single
            (D) TOPOLOGY: linear (ii) MOLECULE TYPE: cDNA (xi) SEQUENCE DESCRIPTION: SEQ ID NO:4:

AGGGCCCATT CATTATGCAG TTCCTCTTTT GCTTTGCTAG ACATCAATCG CCGGCGGATT    60

AATTGATTA                                                           69

(2) INFORMATION FOR SEQ ID NO:5:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:5:

TTAGTTAATT AGGCGGCCGC                                               20

(2) INFORMATION FOR SEQ ID NO:6:

(i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:6:

CGATTACTAT GAAGGATCCG TT                                            22

(2) INFORMATION FOR SEQ ID NO:7:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:7:

TAATGATACT TCCTAGGCAA                                               20

(2) INFORMATION FOR SEQ ID NO:8:

(i) SEQUENCE CHARACTERISTICS:
         (A) LENGTH: 41 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:8:

CGATTACTAG ATCTGAGCTC CCCGGGCTCG AGGGATCCGT T                       41

(2) INFORMATION FOR SEQ ID NO:9:

(i) SEQUENCE CHARACTERISTICS:
         (A) LENGTH: 39 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:9:

TAATGATCTA GACTCGAGGG GCCCGAGCTC CCTAGGCAA                       39

(2) INFORMATION FOR SEQ ID NO:10:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

GATCCGAATT CTAGCT                                                16

(2) INFORMATION FOR SEQ ID NO:11:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GCTTAAGATC GA                                                    12

(2) INFORMATION FOR SEQ ID NO:12:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

TATGAGTAAC TTAACTCTTT TGTTAATTAA AAGTATATTC AAAAAATAAG TTATATAAAT  60

AGATCTGAAT TCGTT                                                 75

(2) INFORMATION FOR SEQ ID NO:13:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

ACTCATTGAA TTGAGAAAAC AATTAATTTT CATATAAGTT TTTTATTCAA TATATTTATC  60

TAGACTTAAG CAA                                                   73

(2) INFORMATION FOR SEQ ID NO:14:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

AAAATGGGCG TGGATTGTTA ACTTTATATA ACTTATTTTT TGAATATAC    49

(2) INFORMATION FOR SEQ ID NO:15:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

ACACGAATGA TTTTCTAAAG TATTTGGAAA GTTTTATAGG TAGTTGATAG AACAAAATAC    60

ATAATTT    67

(2) INFORMATION FOR SEQ ID NO:16:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

TGTGCTTACT AAAAGATTTC ATAAACCTTT CAAAATATCC ATCAACTATC T    51

(2) INFORMATION FOR SEQ ID NO:17:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

TGTAAAAATA AATCACTTTT TATACTAAGA TCTCCCGGGC TGCAGC    46

(2) INFORMATION FOR SEQ ID NO:18:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

TGTTTTATGT ATTAAAACAT TTTTATTTAG TGAAAAATAT GATTCTAGAG GGCCCGACGT    60

CGCCGG    66

(2) INFORMATION FOR SEQ ID NO:19:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

TTTCTGTATA TTTGCACCAA TTTAGATCTT ACTCAAAATA TGTAACAATA                    50

(2) INFORMATION FOR SEQ ID NO:20:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

TGTCATTTAA CACTATACTC ATATTAATAA AATAATATT TATT                           44

(2) INFORMATION FOR SEQ ID NO:21:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

GATCCTGAGT ACTTTGTAAT ATAATGATAT ATATTTTCAC TTTATCTCAT TTGAGAATAA         60

AAAGATCTTA GG                                                             72

(2) INFORMATION FOR SEQ ID NO:22:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

GACTCATGAA ACATTATATT ACTATATATA AAAGTGAAAT AGAGTAAACT CTTATTTTTC         60

TAGAATCCTT AA                                                             72

(2) INFORMATION FOR SEQ ID NO:23:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

GATCCAGATC TCCCGGGAAA AAAATTATTT AACTTTTCAT TAATAGGGAT TTGACGTATG         60

TAGCGTACTA GG                                                             72

(2) INFORMATION FOR SEQ ID NO:24:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

GTCTAGAGGG CCCTTTTTTT AATAAATTGA AAAGTAATTA TCCCTAAACT GCATACTACG      60

CATGATCCTT AA      72

(2) INFORMATION FOR SEQ ID NO:25:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

GGGAGATCTC TCGAGCTGCA GGGCGCCGGA TCCTTTTTCT      40

(2) INFORMATION FOR SEQ ID NO:26:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

CCCTCTAGAG AGCTCGACGT CCCGCGGCCT AGGAAAAAGA      40

(2) INFORMATION FOR SEQ ID NO:27:

(i) SEQUENCE CHARACTERISTICS:
        (A) LENGTH: 3209 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

TGAATGTTAA ATGTTATACT TTGGATGAAG CTATAAATAT GCATTGGAAA AATAATCCAT      60

TTAAAGAAAG GATTCAAATA CTACAAAACC TAAGCGATAA TATGTTAACT AAGCTTATTC      120

TTAACGACGC TTTAAATATA CACAAATAAA CATAATTTTT GTATAACCTA ACAAATAACT      180

AAAACATAAA AATAATAAAA GGAAATGTAA TATCGTAATT ATTTTACTCA GGAATGGGGT      240

TAAATATTTA TATCACGTGT ATATCTATAC TGTTATCGTA TACTCTTTAC AATTACTATT      300

ACGAATATGC AAGAGATAAT AAGATTACGT ATTTAAGAGA ATCTTGTCAT GATAATTGGG      360

TACGACATAG TGATAAATGC TATTTCGCAT CGTTACATAA AGTCAGTTGG AAAGATGGAT      420

TTGACAGATG TAACTTAATA GGTGCAAAAA TGTTAAATAA CAGCATTCTA TCGGAAGATA      480

GGATACCAGT TATATTATAC AAAAATCACT GGTTGGATAA AACAGATTCT GCAATATTCG      540

TAAAAGATGA AGATTACTGC GAATTTGTAA ACTATGACAA TAAAAAGCCA TTTATCTCAA      600

CGACATCGTG TAATTCTTCC ATGTTTTATG TATGTGTTTC AGATATTATG AGATTACTAT      660

AAACTTTTTG TATACTTATA TTCCGTAAAC TATATTAATC ATGAAGAAAA TGAAAAAGTA      720

TAGAAGCTGT TCACGAGCGG TTGTTGAAAA CAACAAAATT ATACATTCAA GATGGCTTAC      780

ATATACGTCT GTGAGGCTAT CATGGATAAT GACAATGCAT CTCTAAATAG GTTTTTGGAC      840

AATGGATTCG ACCCTAACAC GGAATATGGT ACTCTACAAT CTCCTCTTGA AATGGCTGTA      900

-continued

```
ATGTTCAAGA ATACCGAGGC TATAAAAATC TTGATGAGGT ATGGAGCTAA ACCTGTAGTT      960

ACTGAATGCA CAACTTCTTG TCTGCATGAT GCGGTGTTGA GAGACGACTA CAAAATAGTG     1020

AAAGATCTGT TGAAGAATAA CTATGTAAAC AATGTTCTTT ACAGCGGAGG CTTTACTCCT     1080

TTGTGTTTGG CAGCTTACCT TAACAAAGTT AATTTGGTTA AACTTCTATT GGCTCATTCG     1140

GCGGATGTAG ATATTTCAAA CACGGATCGG TTAACTCCTC TACATATAGC CGTATCAAAT     1200

AAAAATTTAA CAATGGTTAA ACTTCTATTG AACAAAGGTG CTGATACTGA CTTGCTGGAT     1260

AACATGGGAC GTACTCCTTT AATGATCGCT GTACAATCTG GAAATATTGA AATATGTAGC     1320

ACACTACTTA AAAAAAATAA AATGTCCAGA ACTGGGAAAA ATTGATCTTG CCAGCTGTAA     1380

TTCATGGTAG AAAAGAAGTG CTCAGGCTAC TTTTCAACAA AGGAGCAGAT GTAAACTACA     1440

TCTTTGAAAG AAATGGAAAA TCATATACTG TTTTGGAATT GATTAAAGAA AGTTACTCTG     1500

AGACACAAAA GAGGTAGCTG AAGTGGTACT CTCAAAATGC AGAACGATGA CTGCGAAGCA     1560

AGAAGTAGAG AAATAACACT TTATGACTTT CTTAGTTGTA GAAAAGATAG AGATATAATG     1620

ATGGTCATAA ATAACTCTGA TATTGCAAGT AAATGCAATA ATAAGTTAGA TTTATTTAAA     1680

AGGATAGTTA AAAATAGAAA AAAAGAGTTA ATTTGTAGGG TTAAAATAAT ACATAAGATC     1740

TTAAAATTTA TAAATACGCA TAATAATAAA AATAGATTAT ACTTATTACC TTCAGAGATA     1800

AAATTTAAGA TATTTACTTA TTTAACTTAT AAAGATCTAA AATGCATAAT TTCTAAATAA     1860

TGAAAAAAAA GTACATCATG AGCAACGCGT TAGTATATTT TACAATGGAG ATTAACGCTC     1920

TATACCGTTC TATGTTTATT GATTCAGATG ATGTTTTAGA AAAGAAAGTT ATTGAATATG     1980

AAAACTTTAA TGAAGATGAA GATGACGACG ATGATTATTG TTGTAAATCT GTTTTAGATG     2040

AAGAAGATGA CGCGCTAAAG TATACTATGG TTACAAAGTA TAAGTCTATA CTACTAATGG     2100

CGACTTGTGC AAGAAGGTAT AGTATAGTGA AAATGTTGTT AGATTATGAT TATGAAAAAC     2160

CAAATAAATC AGATCCATAT CTAAAGGTAT CTCCTTTGCA CATAATTTCA TCTATTCCTA     2220

GTTTAGAATA CTTTTCATTA TATTTGTTTA CAGCTGAAGA CGAAAAAAAT ATATCGATAA     2280

TAGAAGATTA TGTTAACTCT GCTAATAAGA TGAAATTGAA TGAGTCTGTG ATAATAGCTA     2340

TAATCAGAGA AGTTCTAAAA GGAAATAAAA ATCTAACTGA TCAGGATATA AAAACATTGG     2400

CTGATGAAAT CAACAAGGAG GAACTGAATA TAGCTAAACT ATTGTTAGAT AGAGGGGCCA     2460

AAGTAAATTA CAAGGATGTT TACGGTTCTT CAGCTCTCCA TAGAGCTGCT ATTGGTAGGA     2520

AACAGGATAT GATAAAGCTG TTAATCGATC ATGGAGCTGA TGTAAACTCT TTAACTATTG     2580

CTAAAGATAA TCTTATTAAA AAAAATAAT ATCACGTTTA GTAATATTAA AATATATTAA     2640

TAACTCTATT ACTAATAACT CCAGTGGATA TGAACATAAT ACGAAGTTTA TACATTCTCA     2700

TCAAAATCTT ATTGACATCA AGTTAGATTG TGAAAATGAG ATTATGAAAT TAAGGAATAC     2760

AAAAATAGGA TGTAAGAACT TACTAGAATG TTTTATCAAT AATGATATGA ATACAGTATC     2820

TAGGGCTATA AACAATGAAA CGATTAAAAA TTATAAAAAT CATTTCCCTA TATATAATAC     2880

GCTCATAGAA AAATTCATTT CTGAAAGTAT ACTAAGACAC GAATTATTGG ATGGAGTTAT     2940

AAATTCTTTT CAAGGATTCA ATAATAAATT GCCTTACGAG ATTCAGTACA TTATACTGGA     3000

GAATCTTAAT AACCATGAAC TAAAAAAAAT TTTAGATAAT ATACATTAAA AAGGTAAATA     3060

GATCATCTGT TATTATAAGC AAAGATGCTT GTTGCCAATA ATATACAACA GGTATTTGTT     3120

TTTATTTTTA ACTACATATT TGATGTTCAT TCTCTTTATA TAGTATACAC AGAAAATTCA     3180

TAATCCACTT AGAATTTCTA GTTATCTAG                                      3209
```

(2) INFORMATION FOR SEQ ID NO:28:

(i) SEQUENCE CHARACTERISTICS:
           (A) LENGTH: 29 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO:28:

GCTTCCCGGG AATTCTAGCT AGCTAGTTT                                    29

(2) INFORMATION FOR SEQ ID NO:29:

(i) SEQUENCE CHARACTERISTICS:
           (A) LENGTH: 46 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO:29:

ACTCTCAAAA GCTTCCCGGG AATTCTAGCT AGCTAGTTTT TATAAA                 46

(2) INFORMATION FOR SEQ ID NO:30:

(i) SEQUENCE CHARACTERISTICS:
           (A) LENGTH: 50 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO:30:

GATCTTTATA AAAACTAGCT AGCTAGAATT CCCGGGAAGC TTTTGAGAGT             50

(2) INFORMATION FOR SEQ ID NO:31:

(i) SEQUENCE CHARACTERISTICS:
           (A) LENGTH: 71 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO:31:

CTGAAATTAT TTCATTATCG CGATATCCGT TAAGTTTGTA TCGTAATGGT TCCTCAGGCT  60

CTCCTGTTTG T                                                      71

(2) INFORMATION FOR SEQ ID NO:32:

(i) SEQUENCE CHARACTERISTICS:
           (A) LENGTH: 48 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO:32:

CATTACGATA CAAACTTAAC GGATATCGCG ATAATGAAAT AATTTCAG               48

(2) INFORMATION FOR SEQ ID NO:33:

(i) SEQUENCE CHARACTERISTICS:
           (A) LENGTH: 73 base pairs

```
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:33:

ACCCCTTCTG GTTTTTCCGT TGTGTTTTGG GAAATTCCCT ATTTACACGA TCCCAGACAA        60

GCTTAGATCT CAG                                                          73

(2) INFORMATION FOR SEQ ID NO:34:

(i) SEQUENCE CHARACTERISTICS:
       (A) LENGTH: 51 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:34:

CTGAGATCTA AGCTTGTCTG GGATCGTGTA AATAGGGAAT TTCCCAAAAC A                 51

(2) INFORMATION FOR SEQ ID NO:35:

(i) SEQUENCE CHARACTERISTICS:
       (A) LENGTH: 45 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:35:

CAACGGAAAA ACCAGAAGGG GTACAAACAG GAGAGCCTGA GGAAC                        45

(2) INFORMATION FOR SEQ ID NO:36:

(i) SEQUENCE CHARACTERISTICS:
       (A) LENGTH: 11 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:36:

GGATCCCCGG G                                                            11

(2) INFORMATION FOR SEQ ID NO:37:

(i) SEQUENCE CHARACTERISTICS:
       (A) LENGTH: 1740 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:37:

ATGGAGGGCA AAGCCCGTGC AGCGCCGCAA GGCGAAGCAG CGGGCACTGC CACCACAGCA        60

TCAGTTCCTG GAACTACGAC TGATGGCATG GATCCTGGCG TTGTGGCCAC TACCAGCGTG       120

ATCACTGCAG AAAATTCATC CGCATCGATT GCAACAGCAG GGATTGGCGG ACCACCCCAA       180

CAGGTAGACC AACAAGAGAC ATGGAGAACA AATTTTTATT ACAATGATGT TTTCACTTGG       240

TCAGTCGCGG ACGCCCCTGG CAGCATACTT TACACTGTCC AACATTCTCC ACAGAACAAC       300
```

```
CCATTCACAG CCGTGCTGAG CCAGATGTAC GCTGGCTGGG CTGGTGGCAT GCAGTTTCGC    360

TTCATAGTTG CCGGGTCAGG TGTGTTTGGT GGGCGATTGG TCGCGGCTGT GATACCACCA    420

GGCATCGAAA TTGGACCAGG GTTGGAGGTC AGGCAATTTC CTCATGTTGT CATCGACGCC    480

CGTTCACTCG AACCTGTTAC CATCACCATG CCAGACTTGC GTCCCAACAT GTACCATCCA    540

ACTGGTGACC CTGGTCTTGT ACCCACATTA GTCCTCAGTG TTTACAACAA CCTCATCAAC    600

CCGTTTGGTG GGTCCACCAG CGCAATCCAG GTGACAGTGG AAACAAGGCC AAGTGAAGAC    660

TTTGAGTTCG TGATGATTCG AGCCCCCTCC AGTAAGACTG TTGACTCAAT TTCACCCGCA    720

GGCCTCCTCA CGACCCCAGT CCTCACTGGG GTTGGTAATG ACAACAGGTG GAACGGCCAA    780

ATAGTGGGAC TGCAACCAGT ACCTGGAGGG TTTTCTACGT GCAACAGGCA TTGGAACTTG    840

AATGGCAGCA CATATGGCTG GTCAAGCCCT CGGTTTGCCG ACATTGACCA TCGAAGAGGC    900

AGTGCAAGTT ACTCTGGGAA CAACGCAACT AACGTGCTTC AGTTTTGGTA TGCCAATGCT    960

GGGTCTGCAA TCGACAACCC CATCTCCCAG GTTGCACCAG ACGGCTTTCC TGACATGTCG   1020

TTCGTGCCCT TAACGGCCC TGGCATTCCA GCCGCGGGGT GGGTCGGATT TGGTGCAATC   1080

TGGAACAGTA ACAGCGGTGC CCCCAACGTT ACGACTGTGC AGGCCTATGA GTTAGGTTTT   1140

GCCACTGGGG CACCAGGCAA CCTCCAGCCC ACCACCAACA CTTCAGGTGC ACAGACTGTC   1200

GCCAAGTCCA TTTATGCCGT GGTGACTGGC ACAGCCCAAA ACCCAGCCGG ATTGTTTGTG   1260

ATGGCCTCGG GCGTTATCTC CACCCCAAAT GCCAACGCCA TCACATACAC GCCCCAACCA   1320

GACAGAATTG TAACCACACC CGGCACTCCT GCCGCTGCAC CTGTGGGTAA GAACACACCC   1380

ATCATGTTCG CGTCTGTCGT TAGGCGCACC GGTGACGTCA ACGCCACAGC TGGGTCAGCT   1440

AACGGGACCC AGTACGGTAC AGGCTCCCAA CCACTGCCAG TGACAATTGG ACTATCGCTC   1500

AACAACTACT CGTCAGCACT TATGCCCGGA CAGTTTTTCG TTTGGCAGTT AACCTTTGCA   1560

TCTGGTTTCA TGGAGATCGG TTTAAGTGTG GACGGGTATT TTTATGCAGG AACAGGGGCC   1620

TCTACCACAC TCATTGACTT GACTGAACTC ATTGACGTAC GCCCTGTGGG ACCCAGGCCG   1680

TCCAAAAGCA CACTCGTGTT CAACCTGGGG GGAACAGCCA ATGGCTTTTC TTATGTCTGA   1740

(2) INFORMATION FOR SEQ ID NO:38:

(i) SEQUENCE CHARACTERISTICS:
        (A) LENGTH: 1168 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

GGTACCTTCA TAAATACAAG TTTGATTAAA CTTAAGTTGT TCTAAAGTTC TTTCCTCCGA     60

AGGTATAGAA CAAAGTATTT CTTCTACATC CTTACTATTT ATTGCAGCTT TTAACAGCCT    120

ATCACGTATC CTATTTTTAG TATTGGTAGA ATCGTTTTAG TTCTAAAGTT AAAATATTAG    180

ACATAATTGG CATATTGCTT ATTCCTTGCA TAGTTGAGTC TGTAGATCGT TTCAGTATAT    240

CACTGATTAA TGTACTACTG TTATGATGAA ATATAGAATC GATATTGGCA TTTAACTGTT    300

TTGTTATACT AAGTCTAGAT TTTAAATCTT CTAGTAATAT GCTATTTAAT ATAAAAGCTT    360

CCACGTTTTT GTATACATTT CTTTCCATAT TAGTAGCTAC TACTAAATGA TTATCTTCTT    420

TCATATCTTG TAGATAAGAT AGACTATCTT TATCTTTATT AGTAGAAAAT ACTTCTGGCC    480

ATACATCGTT AAATTTTTTT GTTGTTGTTA GATATAATAT TAAATATCTA GAGGATCCTA    540

TTATTTGTGG TAAAATGTTT ATAGAGTAAA ATGATCTGGC TATTAAACAT AGGCCAGTTA    600
```

```
CCATAGAATG CTGCTTCCCG TTACAGTGTT TTACCATAAC CATAGATCTG CCTGTATTGT      660

TGATACATAT AACAGCTGTA AATCCTAAAA AATTCCTATC ATAATTATTA ATATTAGGTA      720

ATTCATTTCC ATGTGAAAGA TAGACTAATT TTATATCCTT TACCTCCAAA TAATTATTTA      780

CATCTCTTAA ACAATCTATT TTAATATCAT TAACTGGTAT TTTATAATAT CCAGAAAGGT     840

TTGAAGGGGT TGATGGAATA AGTCTATTAA CATCGTTAAG TAAATTATTA ATATCATGAA     900

TCTTTATTAT ATTATACCCA TAAGTTAAAT TTATATTTAC TTTCTCATCA TCTGACTTAG     960

TTAGTTTGTA ATAAGGTGTG TCTGAAAAAA TTAAAAGGTA ATTCGTTGAA TGAAGCTGTA    1020

TTTGCTGTAT CATTTTTATC TAATTTTGGA GATTTAGCAG TACTTACTTC ATTAGAAGAA   1080

GAATCTGCCA GTTCCTGTCT ATTACTGATA TTTCGTTTCA TTATTATATG ATTTATTTTT  1140

ACTTTTTCAA TTATATATAC TCAAGCTT                                        1168

(2) INFORMATION FOR SEQ ID NO:39:

(i) SEQUENCE CHARACTERISTICS:
        (A) LENGTH: 392 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:39:

GAATCAAGCT TCATTTTTTC GTAAGTAAGT ATTTTTATTT AATACTTTTT ATTGTACTTA       60

TGTTAAATAT AACTGATGAT AACAAAATCC ATTATGTATT ATTTATAACT GTAATTTCTT      120

TAGCGTAGTT AGATGTCCAA TCTCTCTCAA ATACATCGGC TATCTTTTTA GTGAGATTTT      180

GATCTATGCA GTTGAAACTT ATGAACGCGT GATGATTAAA ATGTGAACCG TCCAAATTTG      240

CAGTCATTAT ATGAGCGTAT CTATTATCTA CTATCATCAT CTTTGAGTTA TTAATATCAT     300

CTACTTTAGA ATTGATAGGA AATATGAATA CCTTTGTAGT AATATCTATA CTATCTACAC     360

CTAACTCATT AAGACTTTTG ATAGTGGAGC TC                                    392

(2) INFORMATION FOR SEQ ID NO:40:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:40:

CTGGAATTCT ATCGCGATAT CCGTTAAGTT TGTATCGTAA TGGAGGGCAA AGCCCGT            57

(2) INFORMATION FOR SEQ ID NO:41:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:41:

GTAAGCTTAT CAGACATAAG AAAAGCC                                            27

(2) INFORMATION FOR SEQ ID NO:42:
```

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:42:

TGGCAGTTAA CCTTTGCATC TGGTTTCATG GAGATCGGTT TAAGTGTGGA CGGGTACTTC    60

TATGCA    66

(2) INFORMATION FOR SEQ ID NO:43:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:43:

TATAAGCTTT CAGACATAAG AAAAGCC    27

(2) INFORMATION FOR SEQ ID NO:44:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:44:

TCATTCGAAT TCTATCGCGA TATCCGTTAA GTTTGTATCG TAATG    45

(2) INFORMATION FOR SEQ ID NO:45:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:45:

ATTGTAATAG AAGTTTGTTC T    21

(2) INFORMATION FOR SEQ ID NO:46:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:46:

AGAACAAACT TCTATTACAA T    21

(2) INFORMATION FOR SEQ ID NO:47:

(i) SEQUENCE CHARACTERISTICS:
        (A) LENGTH: 21 base pairs

-continued

```
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:47:

GCGAAACTGC ATGCCACCAG C                                            21
```

RECOMBINANT POXVIRUS-CALICIVIRUS RABBIT HEMORRHAGIC DISEASE VIRUS (RHDV) COMPOSITIONS AND USES

COMPOSITIONS AND USES RELATED APPLICATIONS

This application is a continuation-in-part of application Ser. No. 08/105,483, filed Aug. 13, 1993, now U.S. Pat. No. 5,494,807, which in turn is a continuation of application Ser. No. 07/847,951, filed Mar. 6, 1992, now abandoned, which in turn is a continuation-in-part of application Ser. No. 07/713,967, filed Jun. 11, 1991, now abandoned, which in turn is a continuation-in-part of application Ser. No. 07/666,056, filed Mar. 7, 1991; now abandoned, and application Ser. No. 08/036,217, filed Mar. 24, 1993, was a continuation of application Ser. No. 07/666,056 and issued Nov. 15, 1994 as U.S. Pat. No. 5,364,773. Each of the aforementioned and above-referenced applications and patent are hereby incorporated herein by reference.

FIELD OF THE INVENTION

The present invention relates to a modified poxvirus and to methods of making and using the same; for instance, a vaccinia virus or avipox (e.g. canarypox or fowlpox), e.g., modified recombinant poxvirus-calicivirus, e.g., rabbit hemorrhagic disease virus (RHDV), such as an attenuated recombinant, especially a NYVAC or ALVAC RHDV recombinant. More in particular, the invention relates to improved vectors for the insertion and expression of foreign genes for use as safe immunization vehicles to elicit an immune response against calicivirus, such as RHDV. Thus, the invention relates to a recombinant poxvirus, which virus expresses gene products of calicivirus, e.g., RHDV, and to immunogenic compositions which induce an immunological response against calicivirus, e.g., RHDV infections when administered to a host, or in vitro as well as to the products of expression of the poxvirus which by themselves are useful for eliciting an immune response e.g., raising antibodies, which antibodies are useful against calicivirus, e.g., RHDV infection, in either seropositive or seronegative individuals, or which expression products or antibodies elicited thereby, isolated from an animal, human or cell culture as the case may be, are useful for preparing a diagnostic kit, test or assay for the detection of the virus, or of infected cells, or, of the expression of the antigens or products in other systems. The isolated expression products are especially useful in kits, tests or assays for detection of antibodies in a system, host, serum or sample, or for generation of antibodies.

Several publications are referenced in this application. Full citation to these references is found at the end of the specification immediately preceding the claims or where the publication is mentioned; and each of these publications is hereby incorporated herein by reference.

BACKGROUND OF THE INVENTION

Vaccinia virus and more recently other poxviruses have been used for the insertion and expression of foreign genes. The basic technique of inserting foreign genes into live infectious poxvirus involves recombination between pox DNA sequences flanking a foreign genetic element in a donor plasmid and homologous sequences present in the rescuing poxvirus (Piccini et al., 1987).

Specifically, the recombinant poxviruses are constructed in two steps known in the art and analogous to the methods for creating synthetic recombinants of poxviruses such as the vaccinia virus and avipox virus described in U.S. Pat. Nos. 4,769,330, 4,772,848, 4,603,112, 5,100,587, and 5,179,993, the disclosures of which are incorporated herein by reference.

First, the DNA gene sequence to be inserted into the virus, particularly an open reading frame from a non-pox source, is placed into an E. coli plasmid construct into which DNA homologous to a section of DNA of the poxvirus has been inserted. Separately, the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA containing a nonessential locus. The resulting plasmid construct is then amplified by growth within E. coli bacteria (Clewell, 1972) and isolated (Clewell et al., 1969; Maniatis et al., 1982).

Second, the isolated plasmid containing the DNA gene sequence to be inserted is transfected into a cell culture, e.g. chick embryo fibroblasts, along with the poxvirus. Recombination between homologous pox DNA in the plasmid and the viral genome respectively gives a poxvirus modified by the presence, in a nonessential region of its genome, of foreign DNA sequences. The term "foreign" DNA designates exogenous DNA, particularly DNA from a non-pox source, that codes for gene products not ordinarily produced by the genome into which the exogenous DNA is placed.

Genetic recombination is in general the exchange of homologous sections of DNA between two strands of DNA. In certain viruses RNA may replace DNA. Homologous sections of nucleic acid are sections of nucleic acid (DNA or RNA) which have the same sequence of nucleotide bases.

Genetic recombination may take place naturally during the replication or manufacture of new viral genomes within the infected host cell. Thus, genetic recombination between viral genes may occur during the viral replication cycle that takes place in a host cell which is co-infected with two or more different viruses or other genetic constructs. A section of DNA from a first genome is used interchangeably in constructing the section of the genome of a second co-infecting virus in which the DNA is homologous with that of the first viral genome.

However, recombination can also take place between sections of DNA in different genomes that are not perfectly homologous. If one such section is from a first genome homologous with a section of another genome except for the presence within the first section of, for example, a genetic marker or a gene coding for an antigenic determinant inserted into a portion of the homologous DNA, recombination can still take place and the products of that recombination are then detectable by the presence of that genetic marker or gene in the recombinant viral genome. Additional strategies have recently been reported for generating recombinant vaccinia virus.

Successful expression of the inserted DNA genetic sequence by the modified infectious virus requires two conditions. First, the insertion must be into a nonessential region of the virus in order that the modified virus remain viable. The second condition for expression of inserted DNA is the presence of a promoter in the proper relationship to the inserted DNA. The promoter must be placed so that it is located upstream from the DNA sequence to be expressed.

Vaccinia virus has been used successfully to immunize against smallpox, culminating in the worldwide eradication of smallpox in 1980. In the course of its history, many strains of vaccinia have arisen. These different strains demonstrate varying immunogenicity and are implicated to varying degrees with potential complications, the most serious of which are post-vaccinial encephalitis and generalized vaccinia (Behbehani, 1983).

With the eradication of smallpox, a new role for vaccinia became important, that of a genetically engineered vector for the expression of foreign genes. Genes encoding a vast number of heterologous antigens have been expressed in vaccinia, often resulting in protective immunity against challenge by the corresponding pathogen (reviewed in Tartaglia et al., 1990a).

The genetic background of the vaccinia vector has been shown to affect the protective efficacy of the expressed foreign immunogen. For example, expression of Epstein Barr Virus (EBV) gp340 in the Wyeth vaccine strain of vaccinia virus did not protect cottontop tamarins against EBV virus induced lymphoma, while expression of the same gene in the WR laboratory strain of vaccinia virus was protective (Morgan et al., 1988).

A fine balance between the efficacy and the safety of a vaccinia virus-based recombinant vaccine candidate is extremely important. The recombinant virus must present the immunogen(s) in a manner that elicits a protective immune response in the vaccinated animal but lacks any significant pathogenic properties. Therefore attenuation of the vector strain would be a highly desirable advance over the current state of technology.

A number of vaccinia genes have been identified which are non-essential for growth of the virus in tissue culture and whose deletion or inactivation reduces virulence in a variety of animal systems.

The gene encoding the vaccinia virus thymidine kinase (TK) has been mapped (Hruby et al., 1982) and sequenced (Hruby et al., 1983; Weir et al., 1983). Inactivation or complete deletion of the thymidine kinase gene does not prevent growth of vaccinia virus in a wide variety of cells in tissue culture. TK- vaccinia virus is also capable of replication in vivo at the site of inoculation in a variety of hosts by a variety of routes.

It has been shown for herpes simplex virus type 2 that intravaginal inoculation of guinea pigs with TK⁻ virus resulted in significantly lower virus titers in the spinal cord than did inoculation with TK⁺ virus (Stanberry et al., 1985). It has been demonstrated that herpesvirus encoded TK activity in vitro was not important for virus growth in actively metabolizing cells, but was required for virus growth in quiescent cells (Jamieson et al., 1974).

Attenuation of TK⁻ vaccinia has been shown in mice inoculated by the intracerebral and intraperitoneal routes (Buller et al., 1985). Attenuation was observed both for the WR neurovirulent laboratory strain and for the Wyeth vaccine strain. In mice inoculated by the intradermal route, TK⁻ recombinant vaccinia generated equivalent anti-vaccinia neutralizing antibodies as compared with the parental TK⁺ vaccinia virus, indicating that in this test system the loss of TK function does not significantly decrease immunogenicity of the vaccinia virus vector. Following intranasal inoculation of mice with TK⁻ and TK⁺ recombinant vaccinia virus (WR strain), significantly less dissemination of virus to other locations, including the brain, has been found (Taylor et al., 1991a).

Another enzyme involved with nucleotide metabolism is ribonucleotide reductase. Loss of virally encoded ribonucleotide reductase activity in herpes simplex virus (HSV) by deletion of the gene encoding the large subunit was shown to have no effect on viral growth and DNA synthesis in dividing cells in vitro, but severely compromised the ability of the virus to grow on serum starved cells (Goldstein et al., 1988). Using a mouse model for acute HSV infection of the eye and reactivatable latent infection in the trigeminal ganglia, reduced virulence was demonstrated for HSV deleted of the large subunit of ribonucleotide reductase, compared to the virulence exhibited by wild type HSV (Jacobson et al., 1989).

Both the small (Slabaugh et al., 1988) and large (Schmidtt et al., 1988) subunits of ribonucleotide reductase have been identified in vaccinia virus. Insertional inactivation of the large subunit of ribonucleotide reductase in the WR strain of vaccinia virus leads to attenuation of the virus as measured by intracranial inoculation of mice (Child et al., 1990).

The vaccinia virus hemagglutinin gene (HA) has been mapped and sequenced (Shida, 1986). The HA gene of vaccinia virus is nonessential for growth in tissue culture (Ichihashi et al., 1971). Inactivation of the HA gene of vaccinia virus results in reduced neurovirulence in rabbits inoculated by the intracranial route and smaller lesions in rabbits at the site of intradermal inoculation (Shida et al., 1988). The HA locus was used for the insertion of foreign genes in the WR strain (Shida et al., 1987), derivatives of the Lister strain (Shida et al., 1988) and the Copenhagen strain (Guo et al., 1989) of vaccinia virus. Recombinant HA⁻ vaccinia virus expressing foreign genes have been shown to be immunogenic (Guo et al., 1989; Itamura et al., 1990; Shida et al., 1988; Shida et al., 1987) and protective against challenge by the relevant pathogen (Guo et al., 1989; Shida et al., 1987).

Cowpox virus (Brighton red strain) produces red (hemorrhagic) pocks on the chorioallantoic membrane of chicken eggs. Spontaneous deletions within the cowpox genome generate mutants which produce white pocks (Pickup et al., 1984). The hemorrhagic function (u) maps to a 38 kDa protein encoded by an early gene (Pickup et al., 1986). This gene, which has homology to serine protease inhibitors, has been shown to inhibit the host inflammatory response to cowpox virus (Palumbo et al., 1989) and is an inhibitor of blood coagulation.

The u gene is present in WR strain of vaccinia virus (Kotwal et al., 1989b). Mice inoculated with a WR vaccinia virus recombinant in which the u region has been inactivated by insertion of a foreign gene produce higher antibody levels to the foreign gene product compared to mice inoculated with a similar recombinant vaccinia virus in which the u gene is intact (Zhou et al., 1990). The u region is present in a defective nonfunctional form in Copenhagen strain of vaccinia virus (open reading frames B13 and B14 by the terminology reported in Goebel et al., 1990a,b).

Cowpox virus is localized in infected cells in cytoplasmic A type inclusion bodies (ATI) (Kato et al., 1959). The function of ATI is thought to be the protection of cowpox virus virions during dissemination from animal to animal (Bergoin et al., 1971). The ATI region of the cowpox genome encodes a 160 kDa protein which forms the matrix of the ATI bodies (Funahashi et al., 1988; Patel et al., 1987). Vaccinia virus, though containing a homologous region in its genome, generally does not produce ATI. In WR strain of vaccinia, the ATI region of the genome is translated as a 94 kDa protein (Patel et al., 1988). In Copenhagen strain of vaccinia virus, most of the DNA sequences corresponding to the ATI region are deleted, with the remaining 3' end of the region fused with sequences upstream from the ATI region to form open reading frame (ORF) A26L (Goebel et al., 1990a,b).

A variety of spontaneous (Altenburger et al., 1989; Drillien et al., 1981; Lai et al., 1989; Moss et al., 1981; Paez et al., 1985; Panicali et al., 1981) and engineered (Perkus et al., 1991; Perkus et al., 1989; Perkus et al., 1986) deletions have been reported near the left end of the vaccinia virus genome. A WR strain of vaccinia virus with a 10 kb spontaneous deletion (Moss et al., 1981; Panicali et al., 1981) was shown to be attenuated by intracranial inoculation in mice (Buller et al., 1985). This deletion was later shown to include 17 potential ORFs (Kotwal et al., 1988b). Specific genes within the deleted region include the virokine N1L and a 35 kDa protein (C3L, by the terminology reported in Goebel et al., 1990a,b). Insertional inactivation of N1L reduces virulence by intracranial inoculation for both normal and nude mice (Kotwal et al., 1989a). The 35 kDa protein is secreted like N1L into the medium of vaccinia virus infected cells. The protein contains homology to the family of complement control proteins, particularly the complement 4B binding protein (C4bp) (Kotwal et al., 1988a). Like the cellular C4bp, the vaccinia 35 kDa protein binds the fourth component of complement and inhibits the classical complement cascade (Kotwal et al., 1990). Thus the vaccinia 35 kDa protein appears to be involved in aiding the virus in evading host defense mechanisms.

The left end of the vaccinia genome includes two genes which have been identified as host range genes, K1L (Gillard et al., 1986) and C7L (Perkus et al., 1990). Deletion of both of these genes reduces the ability of vaccinia virus to grow on a variety of human cell lines (Perkus et al., 1990).

Two additional vaccine vector systems involve the use of naturally host-restricted poxviruses, avipox viruses. Both fowlpoxvirus (FPV) and canarypoxvirus (CPV) have been engineered to express foreign gene products. Fowlpox virus (FPV) is the prototypic virus of the Avipox genus of the Poxvirus family. The virus causes an economically important disease of poultry which has been well controlled since the 1920's by the use of live attenuated vaccines. Replication of the avipox viruses is limited to avian species (Matthews, 1982) and there are no reports in the literature of avipoxvirus causing a productive infection in any non-avian species including man. This host restriction provides an inherent safety barrier to transmission of the virus to other species and makes use of avipoxvirus based vaccine vectors in veterinary and human applications an attractive proposition.

FPV has been used advantageously as a vector expressing antigens from poultry pathogens. The hemagglutinin protein of a virulent avian influenza virus was expressed in an FPV recombinant (Taylor et al., 1988a). After inoculation of the recombinant into chickens and turkeys, an immune response was induced which was protective against either a homologous or a heterologous virulent influenza virus challenge (Taylor et al., 1988a). FPV recombinants expressing the surface glycoproteins of Newcastle Disease Virus have also been developed (Taylor et al., 1990; Edbauer et al., 1990).

Despite the host-restriction for replication of FPV and CPV to avian systems, recombinants derived from these viruses were found to express extrinsic proteins in cells of nonavian origin. Further, such recombinant viruses were shown to elicit immunological responses directed towards the foreign gene product and where appropriate were shown to afford protection from challenge against the corresponding pathogen (Tartaglia et al., 1993a,b; Taylor et al., 1992; 1991b; 1988b).

Caliciviruses have been isolated from porcine (Vesicular exanthema of swine virus—VESV), pinniped (San Miguel sea lion virus—SMSV), feline (Feline calicivirus—FCV), rabbit (Rabbit hemorrhagic disease virus—RHDV), hare (European brown hare virus—EBHV) and human (Norwalk or Hepatitis E virus—HEV) species. They share a common distinctive morphology and are unique among mammalian viruses in containing only one major polypeptide, molecular weight around 60 kDa (Burroughs and Brown 1974). Their genome consist in a positive-stranded RNA molecule of approximately 8 kilobases, the coding sequences for the capsid precursor protein being located within the 3'third of the genomic RNAs. All members of this family are remarkably restricted to their natural host range in which they are responsible of severe diseases (Studdert 1978).

Considering the severity of the diseases induced, the understanding of the basis of a protective immunity against caliciviruses infection in their target species represents an important aim for both veterinary and human medicines. Toward this goal, the development of a relevant and accessible animal model system is required.

The rabbit hemorrhagic disease virus (RHDV) which is responsible for a sudden and acute disease in rabbits (Morisse et al. 1990) provides a unique opportunity to address the mechanisms of immunity against a calicivirus infection in its target species. However, since the virus does not propagate efficiently in tissue culture, its molecular and biochemical analysis have been delayed until the recent cloning and nucleotide sequencing of its genome (Meyers et al. 1991). Contrary to what has been described for other caliciviruses [i.e. FCV (Carter et al. 1992) and HEV (Tam et al. 1991)], the amino terminal sequence analysis of the capsid protein strongly suggested that the RHDV capsid protein is translated from a 2.4 kb subgenomic RNA species and not from the 8 kb genomic RNA (Boga et al. 1992, Parra et al. 1993).

The expression of relevant RHDV proteins using an appropriate recombinant vector is required to access detailed biochemical RHDV analysis and to unravel the immune mechanisms involved in the protection against this calicivirus. As it would also enable the replacement of organ-derived inactivated vaccines (Yu et al. 1991, von Haralambiev et al. 1991, Smid et al. 1991, Villares 1991, David et al. 1991), the development of vaccine candidates utilizing molecular biological methodologies would provide a major safety as well as industrial breakthrough.

The use of live vectors, particularly poxviruses based vectors, expressing immunologically relevant antigens from infectious agents as potential vaccines is encouraged by numerous studies (for a review Cox et al. 1992).

It can thus be appreciated that provision of a calicivirus, e.g., RHDV, recombinant poxvirus, and of compositions and products therefrom, particularly NYVAC or ALVAC based calicivirus, e.g., RHDV, recombinants and compositions and products therefrom, especially such recombinants containing coding for any or all calicivirus capsid protein (i.e., capsid gene), e.g., RHDV capsid gene, and compositions and products therefrom would be a highly desirable advance over the current state of technology.

OBJECTS AND SUMMARY OF THE INVENTION

It is therefore an object of this invention to provide modified recombinant viruses, which viruses have enhanced safety, and to provide a method of making such recombinant viruses.

It is an additional object of this invention to provide a recombinant poxvirus antigenic, vaccine or immunological composition having an increased level of safety compared to known recombinant poxvirus vaccines.

It is a further object of this invention to provide a modified vector for expressing a gene product in a host, wherein the vector is modified so that it has attenuated virulence in the host.

It is another object of this invention to provide a method for expressing a gene product in a cell cultured in vitro using a modified recombinant virus or modified vector having an increased level of safety.

These and other objects and advantages of the present invention will become more readily apparent after consideration of the following.

In one aspect, the present invention relates to a modified recombinant virus having inactivated virus-encoded genetic functions so that the recombinant virus has attenuated virulence and enhanced safety. The functions can be nonessential, or associated with virulence. The virus is advantageously a poxvirus, particularly a vaccinia virus or an avipox virus, such as fowlpox virus and canarypox virus. The modified recombinant virus can include, within a nonessential region of the virus genome, a heterologous DNA sequence which encodes an antigen or epitope derived from calicivirus, e.g., RHDV, such as the capsid gene of a calicivirus, e.g., RHDV capsid gene.

In another aspect, the present invention relates to an antigenic, immunological or vaccine composition or a therapeutic composition for inducing an antigenic or immunological response in a host animal or human inoculated with the composition, said vaccine including a carrier and a modified recombinant virus having inactivated nonessential virus-encoded genetic functions so that the recombinant virus has attenuated virulence and enhanced safety. The virus used in the composition according to the present invention is advantageously a poxvirus, particularly a vaccinia virus or an avipox virus, such as fowlpox virus and canarypox virus. The modified recombinant virus can include, within a non-essential region of the virus genome, a heterologous DNA sequence which encodes an antigenic protein, e.g., derived from calicivirus, e.g., RHDV, such as the capsid gene of a calicivirus, e.g., RHDV capsid gene.

In yet another aspect, the present invention relates to an immunogenic composition containing a modified recombinant virus having inactivated nonessential virus-encoded genetic functions so that the recombinant virus has attenuated virulence and enhanced safety. The modified recombinant virus includes, within a non-essential region of the virus genome, a heterologous DNA sequence which encodes an antigenic protein (e.g., derived from calicivirus, e.g., RHDV, such as the capsid gene of a calicivirus, e.g., RHDV capsid gene) wherein the composition, when administered to a host, is capable of inducing an immunological response specific to the antigen.

In a further aspect, the present invention relates to a method for expressing a gene product in a cell in vitro by introducing into the cell a modified recombinant virus having attenuated virulence and enhanced safety. The modified recombinant virus can include, within a nonessential region of the virus genome, a heterologous DNA sequence which encodes an antigenic protein, e.g. derived from calicivirus, e.g., RHDV, such as the capsid gene of a calicivirus, e.g., RHDV capsid gene. The product can then be administered to animals or humans to stimulate an immune response. The antibodies raised can be useful for the prevention or treatment of calicivirus, e.g., RHDV, and, the antibodies or the isolated in vitro expression products can be used in diagnostic kits, assays or tests to determine the presence or absence in a sample such as sera of calicivirus, e.g., RHDV or antigens therefrom or antibodies thereto (and therefore the absence or presence of the virus or of the products, or of an immune response to the virus or antigens).

In a still further aspect, the present invention relates to a modified recombinant virus having nonessential virus-encoded genetic functions inactivated therein so that the virus has attenuated virulence, and wherein the modified recombinant virus further contains DNA from a heterologous source in a nonessential region of the virus genome. The DNA can code for a calicivirus protein, e.g., a RHDV protein, such as a calicivirus, e.g., RHDV, capsid gene. In particular, the genetic functions are inactivated by deleting an open reading frame encoding a virulence factor or by utilizing naturally host restricted viruses. The virus used according to the present invention is advantageously a poxvirus, particularly a vaccinia virus or an avipox virus, such as fowlpox virus and canarypox virus. Advantageously, the open reading frame is selected from the group consisting of J2R, B13R+B14R, A26L, A56R, C7L–K1L, and I4L (by the terminology reported in Goebel et al., 1990a,b); and, the combination thereof. In this respect, the open reading frame comprises a thymidine kinase gene, a hemorrhagic region, an A type inclusion body region, a hemagglutinin gene, a host range gene region or a large subunit, ribonucleotide reductase; or, the combination thereof. A suitable modified Copenhagen strain of vaccinia virus is identified as NYVAC (Tartaglia et al., 1992), or a vaccinia virus from which has been deleted J2R, B13R+B14R, A26L, A56R, C7L–K11 and I4L or a thymidine kinase gene, a hemorrhagic region, an A type inclusion body region, a hemagglutinin gene, a host range region, and a large subunit, ribonucleotide reductase (See also U.S. Pat. No. 5,364,773). Alternatively, a suitable poxvirus is an ALVAC or, a canarypox virus (Rentschler vaccine strain) which was attenuated, for instance, through more than 200 serial passages on chick embryo fibroblasts, a master seed therefrom was subjected to four successive plaque purifications under agar from which a plaque clone was amplified through five additional passages.

The invention in yet a further aspect relates to the product of expression of the inventive recombinant poxvirus and uses therefor, such as to form antigenic, immunological or vaccine compositions for treatment, prevention, diagnosis or testing. The recombinants are also useful in generating DNA for probes or PCR primers.

These and other embodiments are disclosed or are obvious from and encompassed by the follow detailed description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 8 shows the DNA sequence (SEQ ID NO:27) of a canarypox PvuII fragment containing the C5 ORF.

FIGS. 11A to 11D show graphs of rabies neutralizing antibody titers (RFFIT, IU/ml), booster effect of HDC and vCP65 ($10^{5.5}$ TCID$_{50}$) in volunteers previously immunized with either the same or the alternate vaccine (vaccines given at days 0, 28 and 180, antibody titers measured at days 0, 7, 28, 35, 56, 173, 187 and 208);

FIG. 12A show the nucleotide sequence and deduced amino acid sequence of the RHDV (Saône et Loire strain) capsid gene (SEQ ID NO:37) (Numbering in the upper and lower case left-hand margin pertains to the nucleic acid and amino acid sequences, respectively; the two vaccinia early transcription termination signals are underlined);

FIG. 12B shows the nucleotide sequence of the canarypox C6 locus flanking arms in the donor plasmid pLF14 (SEQ ID NOS.38,39) (The 1,162 bp KpnI/HindIII and the 386 bp HinfI/SacI sequences correspond respectively to the right and left flanking arms of pLF14);

DETAILED DESCRIPTION OF THE INVENTION

Figure 1:
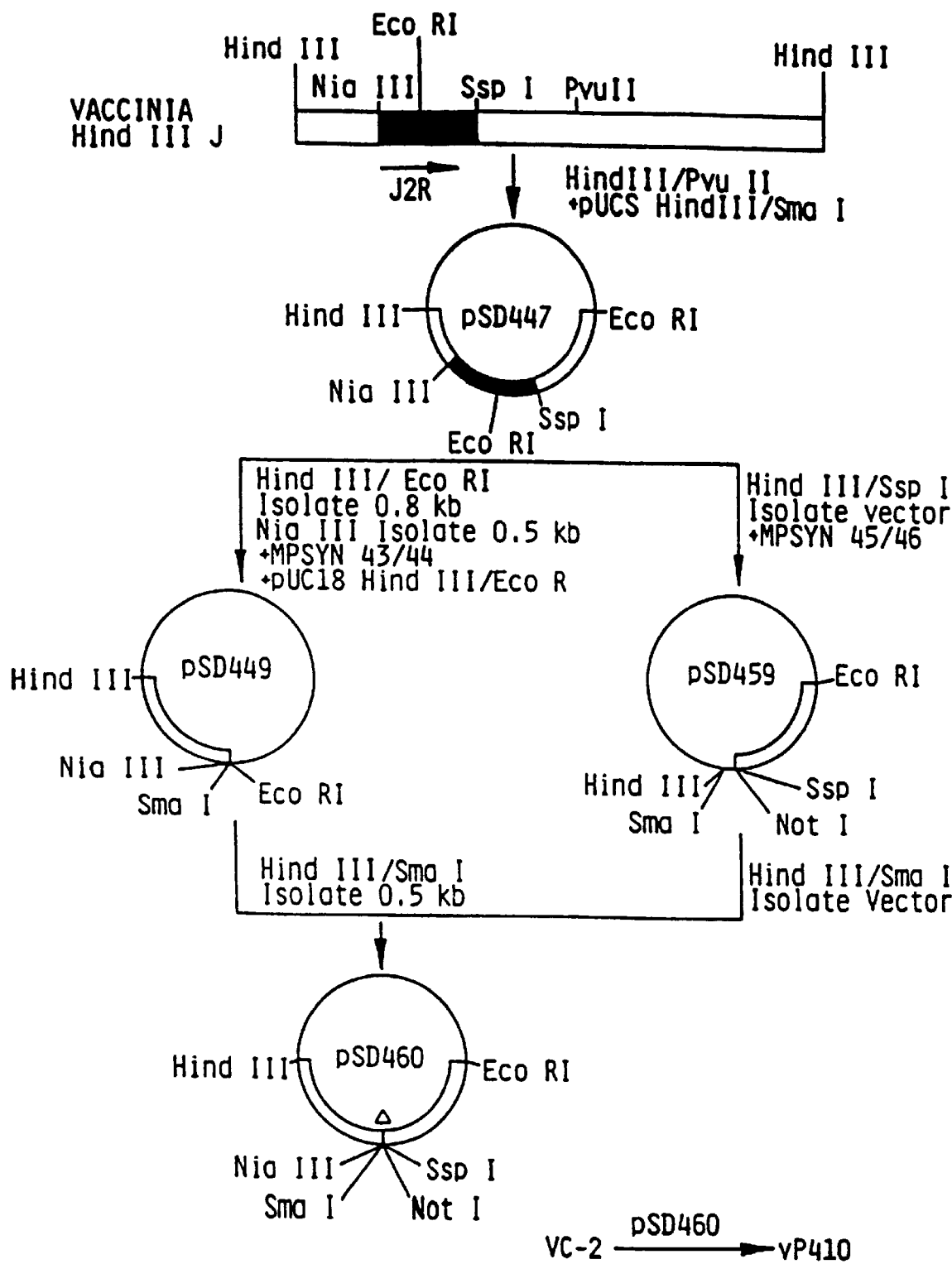
FIG. 1 schematically shows a method for the construction of plasmid pSD460 for deletion of thymidine kinase gene and generation of recombinant vaccinia virus vP410.

To develop a new vaccinia vaccine strain, NYVAC (vP866), the Copenhagen vaccine strain of vaccinia virus was modified by the deletion of six nonessential regions of the genome encoding known or potential virulence factors. The sequential deletions are detailed below (See U.S. Pat. No. 5,364,773, incorporated herein by reference). All designations of vaccinia restriction fragments, open reading frames and nucleotide positions are based on the terminology reported in Goebel et al., 1990a,b.

The deletion loci were also engineered as recipient loci for the insertion of foreign genes.

The regions deleted in NYVAC are listed below. Also listed are the abbreviations and open reading frame designations for the deleted regions (Goebel et al., 1990a,b) and the designation of the vaccinia recombinant (vP) containing all deletions through the deletion specified:

(1) thymidine kinase gene (TK; J2R) vP410;
(2) hemorrhagic region (u; B13R+B14R) vP553;
(3) A type inclusion body region (ATI; A26L) vP618;
(4) hemagglutinin gene (HA; A56R) vP723;
(5) host range gene region (C7L–K1L) vP804; and
(6) large subunit, ribonucleotide reductase (I4L) vP866 (NYVAC).

NYVAC is a genetically engineered vaccinia virus strain that was generated by the specific deletion of eighteen open reading frames encoding gene products associated with virulence and host range. NYVAC is highly attenuated by a number of criteria including i) decreased virulence after intracerebral inoculation in newborn mice, ii) inocuity in genetically ($n^+/nu^+$) or chemically (cyclophosphamide) immunocompromised mice, iii) failure to cause disseminated infection in immunocompromised mice, iv) lack of significant induration and ulceration on rabbit skin, v) rapid clearance from the site of inoculation, and vi) greatly reduced replication competency on a number of tissue culture cell lines including those of human origin. Nevertheless, NYVAC based vectors induce excellent responses to extrinsic immunogens and provided protective immunity.

TROVAC refers to an attenuated fowlpox that was a plaque-cloned isolate derived from the FP-1 vaccine strain of fowlpoxvirus which is licensed for vaccination of 1 day old chicks. ALVAC is an attenuated canarypox virus-based vector that was a plaque-cloned derivative of the licensed canarypox vaccine, Kanapox (Tartaglia et al., 1992). ALVAC has some general properties which are the same as some general properties of Kanapox. ALVAC-based recombinant viruses expressing extrinsic immunogens have also been demonstrated efficacious as vaccine vectors (Tartaglia et al., 1993 a,b). This avipox vector is restricted to avian species for productive replication. On human cell cultures, canarypox virus replication is aborted early in the viral replication cycle prior to viral DNA synthesis. Nevertheless, when engineered to express extrinsic immunogens, authentic expression and processing is observed in vitro in mammalian cells and inoculation into numerous mammalian species induces antibody and cellular immune responses to the extrinsic immunogen and provides protection against challenge with the cognate pathogen (Taylor et al., 1992; Taylor et al., 1991). Recent Phase I clinical trials in both Europe and the United States of a canarypox/rabies glycoprotein recombinant (ALVAC-RG) demonstrated that the experimental vaccine was well tolerated and induced protective levels of rabiesvirus neutralizing antibody titers (Cadoz et al., 1992; Fries et al., 1992). Additionally, peripheral blood mononuclear cells (PBMCs) derived from the ALVAC-RG vaccinates demonstrated significant levels of lymphocyte proliferation when stimulated with purified rabies virus (Fries et al., 1992).

NYVAC, ALVAC and TROVAC have also been recognized as unique among all poxviruses in that the National Institutes of Health ("NIH") (U.S. Public Health Service), Recombinant DNA Advisory Committee, which issues guidelines for the physical containment of genetic material such as viruses and vectors, i.e., guidelines for safety procedures for the use of such viruses and vectors which are based upon the pathogenicity of the particular virus or vector, granted a reduction in physical containment level: from BSL2 to BSL1. No other poxvirus has a BSL1 physical containment level. Even the Copenhagen strain of vaccinia virus—the common smallpox vaccine—has a higher physical containment level; namely, BSL2. Accordingly, the art has recognized that NYVAC, ALVAC and TROVAC have a lower pathogenicity than any other poxvirus.

ALVAC, TROVAC and NYVAC were deposited under the terms of the Budapest Treaty with the American Type Culture Collection (ATCC), 12301 Parklawn Drive, Rockville, Md., 20852, USA: NYVAC under ATCC accession number VR-2559 on Mar. 6, 1997; TROVAC under ATCC accession number VR-2553 on Feb. 6, 1997 and, ALVAC under ATCC accession number VR-2547 on Nov. 14, 1996.

NYVAC, as discussed above, is derived from the Copenhagen vaccine strain by the precise deletion of 18 open reading frames associated with virulence and host range. The highly attenuated phenotype of NYVAC does not significantly diminish its immunizing potential as a vector in both experimental and target species (Tartaglia et al. 1992, Konishi et al. 1992). NYVAC-based recombinants expressing rabies virus, Japanese encephalitis virus and malaria antigens are currently undergoing human clinical evaluation. A further extension of using highly attenuated poxviruses as vaccine vectors, as discussed above, is to take advantage of poxviruses with naturally occurring restricted host ranges, such as avipoxviruses. Despite the inability of ALVAC to productively replicate in non-avian species, ALVAC has been shown to elicit protective immune responses in non-avian species against several viral pathogens (Taylor et al. 1991, Taylor et al. 1992, Tartaglia et al. 1993). Since this vector does not replicate in such species, disseminated infection within the vaccinee or spread to contacts or to the general environment should be eliminated. Recent phase I clinical trials demonstrated that the experimental vaccines based on this vector are well tolerated and elicit immune responses towards extrinsic immunogens (Cadoz et al. 1992; See also discussion above).

Clearly based on the attenuation profiles of the NYVAC, ALVAC, and TROVAC vectors and their demonstrated ability to elicit both humoral and cellular immunological responses to extrinsic immunogens (Tartaglia et al., 1993a,b; Taylor et al., 1992; Konishi et al., 1992) such recombinant viruses offer a distinct advantage over previously described vaccinia-based recombinant viruses.

This invention involves protection against rabbit hemorrhagic disease and calicivirus in general; and, comprehends NYVAC- and an ALVAC-based calicivirus, e.g, RHDV, capsid protein expressing recombinant viruses which confer protective immunity in rabbits against RHDV challenge exposure, and to uses of expression products from the viruses and to antibodies therefrom.

Described below, in the Examples especially, is the cloning and sequence analysis of the calicivirus, particularly RHDV, capsid gene (Saône et Loire strain), the derivation of both NYVAC (vaccinia virus) and ALVAC (canary pox virus) recombinant viruses expressing the capsid gene product and the demonstration of protection conferred by these recombinants upon experimental challenge.

Since genetic variations have been reported for other members of the calicivirus family (Huang et al. 1992; Neill, 1992; Seal et al. 1993), the nucleotide sequence analysis of the capsid gene of a French RHDV isolate (Saône et Loire strain) was performed to determine the extent to which this isolate may differ from previously published RHDV stain (Meyers et al. 1991). The capsid gene reveals a 1.740 bp long ORF with very high nucleotide homology (97.3% identity) with the previously published RHDV German stain (Meyers et al. 1991). Due to most differences occurring in the variable position of the codons, the corresponding amino acid sequence is virtually identical (99.1% identity) to the previously reported sequence. Similar high levels of homology in the capsid gene have been recently reported between three geographic HEV isolates (Huang et al. 1992). However, since the first two-third of the French RHDV genome, which for other caliciviruses has been shown to contain hypervariable regions, has not yet been analyzed. The exact relationship between this French isolate and previously described isolates remains to be further investigated. Nevertheless, the nucleotide sequence derived from the highly conserved RHDV capsid gene is useful in developing polymerase chain reaction (PCR)-based tests or for primers to confirm viral infections.

To derive the canarypox (ALVAC) based recombinant virus (vCP309) and the NYVAC based recombinant virus (vP1249), which both express the RHDV capsid gene, is was assumed that the ATG in position #5305 (Meyers et al. 1991) is used as a native translation initiation codon. This assumption has recently been proven correct by an amino acid analysis of purified RHDV capsid protein which indicates that the chosen ATG is indeed the initiation codon used by the virus to express its capsid protein (Parra et al. 1993). The recognition of the vCP309 and vP1249 expressed polypeptides by two independent conformation dependent RHDV MAbs, by immunoprecipitation and by FACS analysis, strongly demonstrates that vCP309 and vP1249 are expressing a native RHDV capsid protein. As demonstrated recently for baculovirus expressed recombinant RHDV capsid protein (Laurent et al. 1994), without necessarily wishing to be bound by any one particular theory, it is believed that the recombinant polypeptide assembles into virus-like particles.

Rabbits vaccinated with vCP309 or vP1249 survive a strong lethal RHDV challenge which kills all control unvaccinated animals (See Table below). These results clearly indicate that the expression of the RHDV capsid protein is sufficient to confer protection against RHDV challenge exposure. In agreement with two recent reports describing protection of rabbits against RHDV challenge utilizing either a baculovirus (Laurent et al. 1994) or an E. coli (Boga et al. 1994) expressed recombinant RHDV capsid protein preparation, this invention presents a recombinant capsid-based vaccine against RHDV and shows that this strategy is useful to protect against calicivirus infections in general. The recent demonstration that the two MAbs (3H6 and 1H8), used to characterize vCP309 and vP1249, cross react with EBHV extracts (Wirblich et al. 1994) shows that vCP309 and vP1249 provide cross protection against an EBHV challenge.

As it is currently not possible to propagate RHDV in tissue culture, recombinant DNA approaches to develop a RHDV vaccine candidate provides a means for replacing the current conventional inactivated RHDV vaccine preparations which have been derived from infected rabbit livers (Yu et al. 1991, von Haralambiev et al. 1991, Smid et al. 1991, Villares 1991, David et al. 1991), and thus constitutes a major safety as well as an industrial breakthrough. Since the Norwalk virus, a calicivirus responsible for hepatitis E in humans, also cannot be propagated in any cell culture (Kapikian and Chanock, 1990), these results have direct implications for the derivation of a hepatitis E vaccine. Indeed, the RHDV expressing recombinants may cross react against hepatitis E (thus, the poxvirus-RHDV recombinants are useful in humans).

Furthermore, the results herein illustrate the utility of the ALVAC and NYVAC vector systems to elicit protective immune responses in target species. Significantly, since these vectors are characterized by either a replication restricted to avian species (ALVAC) or a highly attenuated phenotype (NYVAC), it virtually eliminates potential vaccine-induced and vaccine-associated complications.

Recently, two reports have described protection of rabbits against RHDV challenge utilizing either a baculovirus (Laurent et al. 1994) or an *E. Coli* (Boga et al. 1994) expressed recombinant RHDV capsid protein preparation. Both reports suggest an association between the rabbit humoral response and protection. This invention differs significantly from the two aforementioned subunit based approaches. Since vCP309 and vP1249 are live attenuated recombinant viruses which lead to the de novo intracellular expression of the immunogen, a stronger stimulation of cell-mediated immune response may be elicited. The herein results are in agreement with this statement since they fail to illustrate any clear association between serological titers and protective immunity.

The recombinant canarypox vCP309 and NYVAC vP1249 herein described are also instrumental in the analysis of the relative importance of humoral and cell-mediated immune responses in protection against RHDV infection and calicivirus infections in general.

The administration procedure for recombinant virus or expression product thereof, compositions of the invention such as immunological, antigenic or vaccine compositions or therapeutic compositions can be via a parenteral route (intradermal, intramuscular or subcutaneous). Such an administration enables a systemic immune response.

More generally, the inventive antigenic, immunological or vaccine compositions or therapeutic compositions (compositions containing the poxvirus recombinants of the invention) can be prepared in accordance with standard techniques well known to those skilled in the veterinary or pharmaceutical art. Such compositions can be administered in dosages and by techniques well known to those skilled in the veterinary or medical arts taking into consideration such factors as the age, sex, weight, and condition of the particular animal or patient, and the route of administration. The compositions can be administered alone, or can be co-administered or sequentially administered with compositions of the invention or with other immunological, antigenic or vaccine or therapeutic compositions in animals or patients. Such other compositions can include purified antigens from calicivirus (e.g., RHDV) or from the expression of such antigens by a recombinant poxvirus or other vector system or, such other compositions can include a recombinant poxvirus which expresses other calicivirus (e.g., RHDV) antigens or biological response modifiers again taking into consideration such factors as the age, sex, weight, and condition of the particular patient, and, the route of administration.

Examples of compositions of the invention include liquid preparations for orifice, e.g., oral, nasal, anal, vaginal, etc., administration such as suspensions, syrups or elixirs; and, preparations for parenteral, subcutaneous, intradermal, intramuscular or intravenous administration (e.g., injectable administration) such as sterile suspensions or emulsions. In such compositions the recombinant poxvirus may be in admixture with a suitable carrier, diluent, or excipient such as sterile water, physiological saline, glucose or the like.

Further, the products of expression of the inventive recombinant poxviruses can be used directly to stimulate an immune response in individuals or in animals. Thus, the expression products can be used in compositions of the invention instead or in addition to the inventive recombinant poxvirus in the aforementioned compositions.

Additionally, the inventive recombinant poxvirus and the expression products therefrom stimulate an immune or antibody response in humans and animals and therefore those products are antigens. From those antibodies or antigens, by techniques well-known in the art, monoclonal antibodies can be prepared and, those monoclonal antibodies or the antigens, can be employed in well known antibody binding assays, diagnostic kits or tests to determine the presence or absence of particular calicivirus, e.g., RHDV, antigen(s) and therefore the presence or absence of the virus or expression of the antigen(s) (in calicivirus, e.g., RHDV, or other systems), or to determine whether an immune response to the virus or antigen(s) has simply been stimulated. Those monoclonal antibodies or the antigens can also be employed in immunoadsorption chromatography to recover or isolate calicivirus, e.g., RHDV or expression products of the inventive recombinant poxvirus.

More in particular, the inventive recombinants and compositions have numerous utilities, including:

(i) inducing an immunological response (e.g., use as or as part of a vaccine regimen); and (ii) a means for generating calicivirus, e.g., RHDV, protein in vitro without the risk of virus infection.

The products of expression of the inventive recombinant poxvirus can be used directly to stimulate an immune response in individuals or in animals. Thus, the expression products can be used in compositions of the invention instead of or in addition to the inventive recombinant poxvirus.

Additionally, the inventive recombinant poxvirus and the expression products therefrom stimulate an immune or antibody response in humans and animals. From those antibodies, by techniques well-known in the art, monoclonal antibodies can be prepared and, those monoclonal antibodies or the expression products of the inventive poxvirus and composition can be employed in well known antibody binding assays, diagnostic kits or tests to determine the presence or absence of particular calicivirus, e.g., RHDV antigen(s) or antibody(ies) and therefore the presence or absence of the virus, or to determine whether an immune response to the virus or antigen(s) has simply been stimulated. Those monoclonal antibodies can also be employed in immunoadsorption chromatography to recover, isolate or detect calicivirus, e.g., RHDV or expression products of the inventive recombinant poxvirus. Methods for producing monoclonal antibodies and for uses of monoclonal antibodies, and, of uses and methods for calicivirus, e.g., RHDV antigens—the expression products of the inventive poxvirus and composition—are well known to those of ordinary skill in the art. They can be used in diagnostic methods, kits, tests or assays, as well as to recover materials by immunoadsorption chromatography or by immunoprecipitation.

Monoclonal antibodies are immunoglobulins produced by hybridoma cells. A monoclonal antibody reacts with a single antigenic determinant and provides greater specificity than a conventional, serum-derived antibody. Furthermore, screening a large number of monoclonal antibodies makes it possible to select an individual antibody with desired specificity, avidity and isotype. Hybridoma cell lines provide a constant, inexpensive source of chemically identical antibodies and preparations of such antibodies can be easily standardized. Methods for producing monoclonal antibodies are well known to those of ordinary skill in the art, e.g., Koprowski, H. et al., U.S. Pat. No. 4,196,265, issued Apr. 1, 1989, incorporated herein by reference.

Uses of monoclonal antibodies are known. One such use is in diagnostic methods, e.g., David, G. and Greene, H. U.S. Pat. No. 4,376,110, issued Mar. 8, 1983; incorporated herein by reference. Monoclonal antibodies have also been used to recover materials by immunoadsorption chromatography, e.g., Milstein, C. 1980, Scientific American 243:66, 70, incorporated herein by reference.

Furthermore, the inventive recombinant poxvirus or DNA therefrom can be used to probe for calicivirus, e.g., RHDV or, to generate PCR primers for duplication or detection of calicivirus, e.g., RHDV DNA.

Other utilities also exist for embodiments of the invention.

A better understanding of the present invention and of its many advantages will be had from the following examples, given by way of illustration.

EXAMPLES

DNA Cloning and Synthesis. Plasmids were constructed, screened and grown by standard procedures (Maniatis et al., 1982; Perkus et al., 1985; Piccini et al., 1987). Restriction endonucleases were obtained from Bethesda Research Laboratories, Gaithersburg, Md., New England Biolabs, Beverly, Mass.; and Boehringer Mannheim Biochemicals, Indianapolis, Ind.. Klenow fragment of *E. coli* polymerase was obtained from Boehringer Mannheim Biochemicals. BAL-31 exonuclease and phage T4 DNA ligase were obtained from New England Biolabs. The reagents were used as specified by the various suppliers.

Synthetic oligodeoxyribonucleotides were prepared on a Biosearch 8750 or Applied Biosystems 380B DNA synthesizer as previously described (Perkus et al., 1989). DNA sequencing was performed by the dideoxy-chain termination method (Sanger et al., 1977) using Sequenase (Tabor et al., 1987) as previously described (Guo et al., 1989). DNA amplification by polymerase chain reaction (PCR) for sequence verification (Engelke et al., 1988) was performed using custom synthesized oligonucleotide primers and GeneAmp DNA amplification Reagent Kit (Perkin Elmer Cetus, Norwalk, Conn.) in an automated Perkin Elmer Cetus DNA Thermal Cycler. Excess DNA sequences were deleted from plasmids by restriction endonuclease digestion followed by limited digestion by BAL-31 exonuclease and mutagenesis (Mandecki, 1986) using synthetic oligonucleotides.

Cells, Virus, and Transfection. The origins and conditions of cultivation of the Copenhagen strain of vaccinia virus and NYVAC has been previously described (Guo et al., 1989; Tartaglia et al., 1992). Generation of recombinant virus by recombination, in situ hybridization of nitrocellulose filters and screening for B-galactosidase activity are as previously described (Panicali et al., 1982; Piccini et al., 1987; Perkus et al., 1989).

The parental canarypox virus (Rentschler strain) is a vaccinal strain for canaries. The vaccine strain was obtained from a wild type isolate and attenuated through more than 200 serial passages on chick embryo fibroblasts. A master viral seed was subjected to four successive plaque purifications under agar and one plaque clone was amplified through five additional passages after which the stock virus was used as the parental virus in in vitro recombination tests. The plaque purified canarypox isolate is designated ALVAC.

The strain of fowlpox virus (FPV) designated FP-1 has been described previously (Taylor et al., 1988a). It is an attenuated vaccine strain useful in vaccination of day old chickens. The parental virus strain Duvette was obtained in France as a fowlpox scab from a chicken. The virus was attenuated by approximately 50 serial passages in chicken embryonated eggs followed by 25 passages on chicken embryo fibroblast cells. The virus was subjected to four successive plaque purifications. One plaque isolate was further amplified in primary CEF cells and a stock virus, designated as TROVAC, established.

NYVAC, ALVAC and TROVAC viral vectors and their derivatives were propagated as described previously (Piccini et al., 1987; Taylor et al., 1988a,b). Vero cells and chick embryo fibroblasts (CEF) were propagated as described previously (Taylor et al., 1988a,b).

As to NYVAC and especially Examples 1 to 6, reference is made to U.S. Pat. No. 5,364,773, incorporated herein by reference.

EXAMPLE 1

CONSTRUCTION OF PLASMID pSD460 FOR DELETION OF THYMIDINE KINASE GENE (J2R)

Referring now to FIG. 1, plasmid pSD406 contains vaccinia HindIII J (pos. 83359–88377) cloned into pUC8. pSD406 was cut with HinDIII and PvuII, and the 1.7 kb fragment from the left side of HindIII J cloned into pUC8 cut with HindIII/SmaI, forming pSD447. pSD447 contains the entire gene for J2R (pos. 83855–84385). The initiation codon is contained within an NlaIII site and the termination codon is contained within an SspI site. Direction of transcription is indicated by an arrow in FIG. 1.

To obtain a left flanking arm, a 0.8 kb HindIII/EcoRI fragment was isolated from pSD447, then digested with NlaIII and a 0.5 kb HindIII/NlaIII fragment isolated. Annealed synthetic oligonucleotides MPSYN43/MPSYN44 (SEQ ID NO:1/SEQ ID NO:2)

```
                                         SmaI
MPSYN43  5'      TAATTAACTAGCTACCCGGG         3'

MPSYN44  3'  GTACATTAATTGATCGATGGGCCCTTAA    5'
             NlaIII                     EcoRI
``` were ligated with the 0.5 kb HindIII/NlaIII fragment into pUC18 vector plasmid cut with HindIII/EcoRI, generating plasmid pSD449.

To obtain a restriction fragment containing a vaccinia right flanking arm and pUC vector sequences, pSD447 was cut with SspI (partial) within vaccinia sequences and HindIII at the pUC/vaccinia junction, and a 2.9 kb vector fragment isolated. This vector fragment was ligated with annealed synthetic oligonucleotides MPSYN45/MPSYN46 (SEQ ID NO:3/SEQ ID NO:4)

```
             HindIII  SmaI
MPSYN45  5'  AGCTTCCCGGGTAAGTAATACGTCAAGGAGAAAACGAA

MPSYN46  3'          AGGGCCCATTCATTATGCAGTTCCTCTTTTGCTT

NotI             SspI
             ACGATCTGTAGTTAGCGGCCGCCTAATTAACTAAT   3'  MPSYN45

TGCTAGACATCAATCGCCGGCGGATTAATTGATTA   5'  MPSYN46
``` generating pSD459.

To combine the left and right flanking arms into one plasmid, a 0.5 kb HindIII/SmaI fragment was isolated from pSD449 and ligated with pSD459 vector plasmid cut with HindIII/SmaI, generating plasmid pSD460. pSD460 was used as donor plasmid for recombination with wild type parental vaccinia virus Copenhagen strain VC-2. $^{32}$P labelled probe was synthesized by primer extension using MPSYN45 (SEQ ID NO:3) as template and the complementary 20mer oligonucleotide MPSYN47 (SEQ ID NO:5) (5' TTAGTTAATTAGGCGGCCGC 3') as primer. Recombinant virus vP410 was identified by plaque hybridization.

EXAMPLE 2

CONSTRUCTION OF PLASMID pSD486 FOR DELETION OF HEMORRHAGIC REGION (B13R+B14R)

Figure 2:
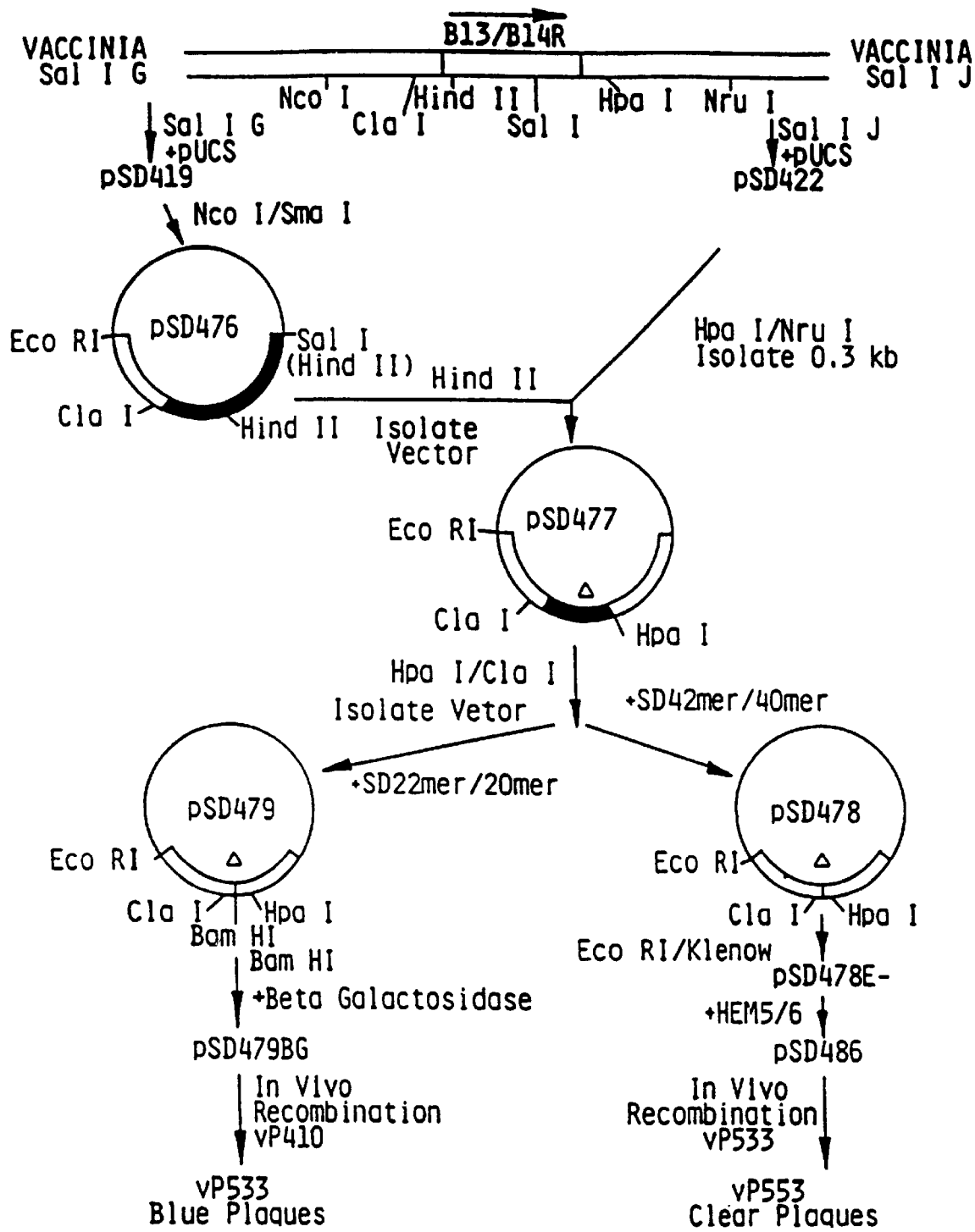
FIG. 2 schematically shows a method for the construction of plasmid pSD486 for deletion of hemorrhagic region and generation of recombinant vaccinia virus vP553.

Referring now to FIG. 2, plasmid pSD419 contains vaccinia SalI G (pos. 160,744–173,351) cloned into pUC8. pSD422 contains the contiguous vaccinia SalI fragment to the right, SalI J (pos. 173,351–182,746) cloned into pUC8.

To construct a plasmid deleted for the hemorrhagic region, u, B13R–B14R (pos. 172,549–173,552), pSD419 was used as the source for the left flanking arm and pSD422 was used as the source of the right flanking arm. The direction of transcription for the u region is indicated by an arrow in FIG. 2.

To remove unwanted sequences from pSD419, sequences to the left of the NcoI site (pos. 172,253) were removed by digestion of pSD419 with NciI/SmaI followed by blunt ending with Klenow fragment of E. coli polymerase and ligation generating plasmid pSD476. A vaccinia right flanking arm was obtained by digestion of pSD422 with HpaI at the termination codon of B14R and by digestion with NruI 0.3 kb to the right. This 0.3 kb fragment was isolated and ligated with a 3.4 kb HincII vector fragment isolated from pSD476, generating plasmid pSD477. The location of the partial deletion of the vaccinia u region in pSD477 is indicated by a triangle. The remaining B13R coding sequences in pSD477 were removed by digestion with ClaI/HpaI, and the resulting vector fragment was ligated with annealed synthetic oligonucleotides SD22mer/SD20mer (SEQ ID NO:6/SEQ ID NO:7)

```
                     ClaI          BamHI HpaI
         SD22mer  5' CGATTACTATGAAGGATCCGTT   3'

SD20mer  3'    TAATGATACTTCCTAGGCAA  5'
``` generating pSD479. pSD479 contains an initiation codon (underlined) followed by a BamHI site. To place E. coli Beta-galactosidase in the B13–B14 (u) deletion locus under the control of the u promoter, a 3.2 kb BamHI fragment containing the Beta-galactosidase gene (Shapira et al., 1983) was inserted into the BamHI site of pSD479, generating pSD479BG. pSD479BG was used as donor plasmid for recombination with vaccinia virus vP410. Recombinant vaccinia virus vP533 was isolated as a blue plaque in the presence of chromogenic substrate X-gal. In vP533 the B13R–B14R region is deleted and is replaced by Beta-galactosidase.

To remove Beta-galactosidase sequences from vP533, plasmid pSD486, a derivative of pSD477 containing a polylinker region but no initiation codon at the U deletion junction, was utilized. First the ClaI/HpaI vector fragment from pSD477 referred to above was ligated with annealed synthetic oligonucleotides SD42mer/SD40mer (SEQ ID NO:8/SEQ ID NO:9)

```
                 ClaI         SacI         XhoI        HpaI
SD42mer  5' CGATTACTAGATCTGAGCTCCCCGGGCTCGAGGGATCCGTT    3'

SD40mer  3'    TAATGATCTAGACTCGAGGGGCCCGAGCTCCCTAGGCAA   5'
                 BglII        SmaI        BamHI
``` generating plasmid pSD478. Next the EcoRI site at the pUC/vaccinia junction was destroyed by digestion of pSD478 with EcoRI followed by blunt ending with Klenow fragment of E. coli polymerase and ligation, generating plasmid pSD478E$^-$. pSD478E$^-$ was digested with BamHI and HpaI and ligated with annealed synthetic oligonucleotides HEM5/HEM6 (SEQ ID NO:10/SEQ ID NO:11)

```
                   BamHI EcoRI    HpaI
         HEM5  5'  GATCCGAATTCTAGCT   3'

HEM6  3'      GCTTAAGATCGA   5'
``` generating plasmid pSD486. pSD486 was used as donor plasmid for recombination with recombinant vaccinia virus vP533, generating vP553, which was isolated as a clear plaque in the presence of X-gal.

EXAMPLE 3

CONSTRUCTION OF PLASMID pMP494Δ FOR DELETION OF ATI REGION (A26L)

Figure 3:
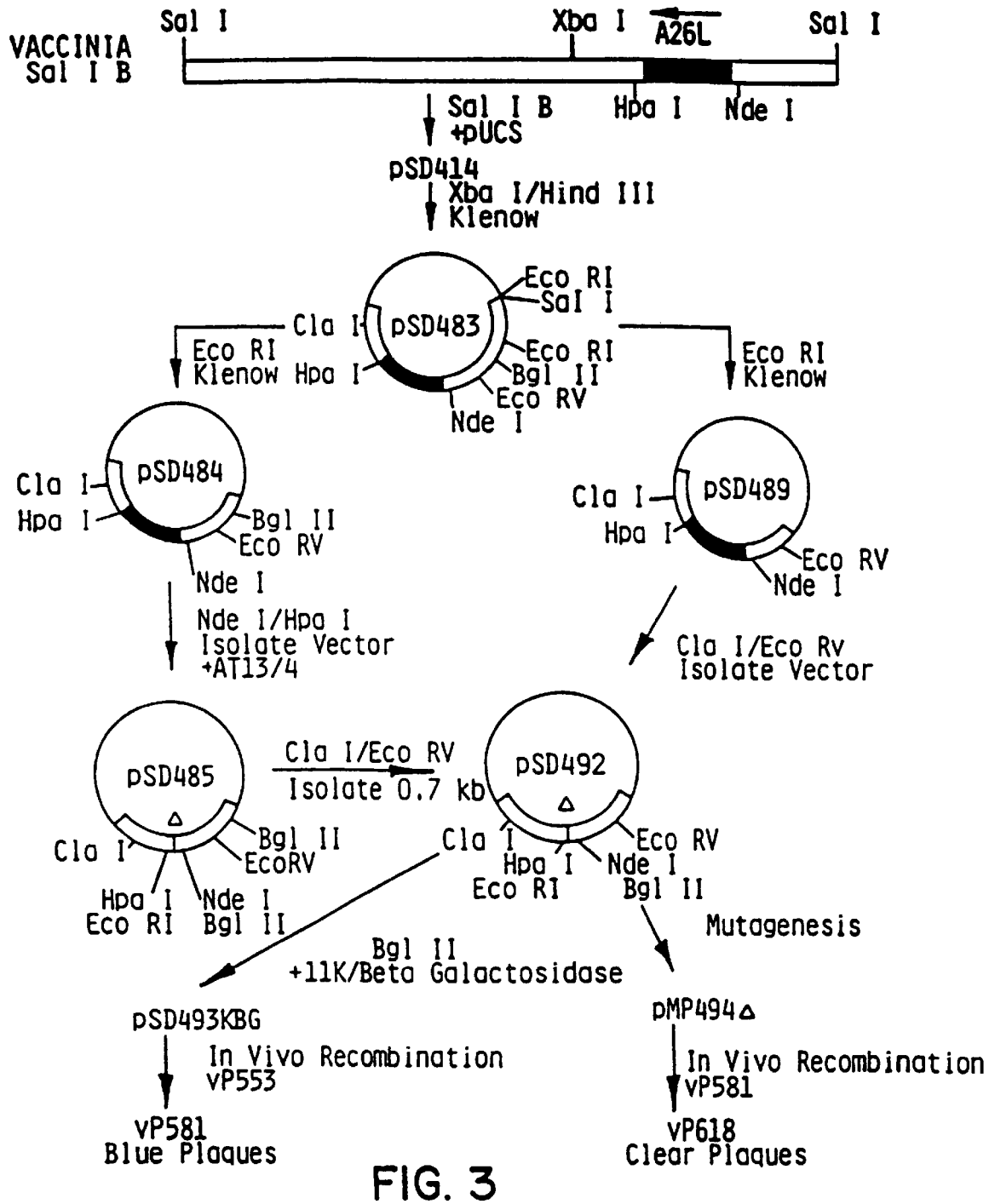
FIG. 3 schematically shows a method for the construction of plasmid pMP494Δ for deletion of ATI region and generation of recombinant vaccinia virus vP618.

Referring now to FIG. 3, pSD414 contains SalI B cloned into pUC8. To remove unwanted DNA sequences to the left of the A26L region, pSD414 was cut with XbaI within vaccinia sequences (pos. 137,079) and with HindIII at the pUC/vaccinia junction, then blunt ended with Klenow fragment of E. coli polymerase and ligated, resulting in plasmid pSD483. To remove unwanted vaccinia DNA sequences to the right of the A26L region, pSD483 was cut with EcoRI (pos. 140,665 and at the pUC/vaccinia junction) and ligated, forming plasmid pSD484. To remove the A26L coding region, pSD484 was cut with NdeI (partial) slightly upstream from the A26L ORF (pos. 139,004) and with HpaI (pos. 137,889) slightly downstream from the A26L ORF. The 5.2 kb vector fragment was isolated and ligated with annealed synthetic oligonucleotides ATI3/ATI4 (SEQ ID NO:12/SEQ ID NO:13)

```
          NdeI
ATI3   5' TATGAGTAACTTAACTCTTTTGTTAATTAAAAGTATATTCAAAAAATAAGT

ATI4   3'    ACTCATTGAATTGAGAAAACAATTAATTTTCATATAAGTTTTTTATTCA

BglII EcoRI HpaI
       TATATAAATAGATCTGAATTCGTT  3' ATI3

ATATATTTATCTAGACTTAAGCAA  5' ATI4
``` reconstructing the region upstream from A26L and replacing the A26L ORF with a short polylinker region containing the restriction sites BglII, EcoRI and HpaI, as indicated above. The resulting plasmid was designated pSD485. Since the BglII and EcoRI sites in the polylinker region of pSD485 are not unique, unwanted BglII and EcoRI sites were removed from plasmid pSD483 (described above) by digestion with BglII (pos. 140,136) and with EcoRI at the pUC/vaccinia junction, followed by blunt ending with Klenow fragment of E. coli polymerase and ligation. The resulting plasmid was designated pSD489. The 1.8 kb ClaI (pos. 137,198)/EcoRV (pos. 139,048) fragment from pSD489 containing the A26L ORF was replaced with the corresponding 0.7 kb polylinker-containing ClaI/EcoRV fragment from pSD485, generating pSD492. The BglII and EcoRI sites in the polylinker region of pSD492 are unique.

A 3.3 kb BglII cassette containing the E. coli Beta-galactosidase gene (Shapira et al., 1983) under the control of the vaccinia 11 kDa promoter (Bertholet et al., 1985; Perkus et al., 1990) was inserted into the BglII site of pSD492, forming pSD493KBG. Plasmid pSD493KBG was used in recombination with rescuing virus vP553. Recombinant vaccinia virus, vP581, containing Beta-galactosidase in the A26L deletion region, was isolated as a blue plaque in the presence of X-gal.

To generate a plasmid for the removal of Beta-galactosidase sequences from vaccinia recombinant virus vP581, the polylinker region of plasmid pSD492 was deleted by mutagenesis (Mandecki, 1986) using synthetic oligonucleotide MPSYN177 (SEQ ID NO:14) (5' AAAATGGGCGTGGATTGTTAACTTTATATAA-CTTATTTTTTGAATATAC 3'). In the resulting plasmid, pMP494Δ, vaccinia DNA encompassing positions [137,889–138,937], including the entire A26L ORF is deleted. Recombination between the pMP494Δ and the Beta-galactosidase containing vaccinia recombinant, vP581, resulted in vaccinia deletion mutant vP618, which was isolated as a clear plaque in the presence of X-gal.

EXAMPLE 4

CONSTRUCTION OF PLASMID pSD467 FOR DELETION OF HEMAGGLUTININ GENE (A56R)

Figure 4:
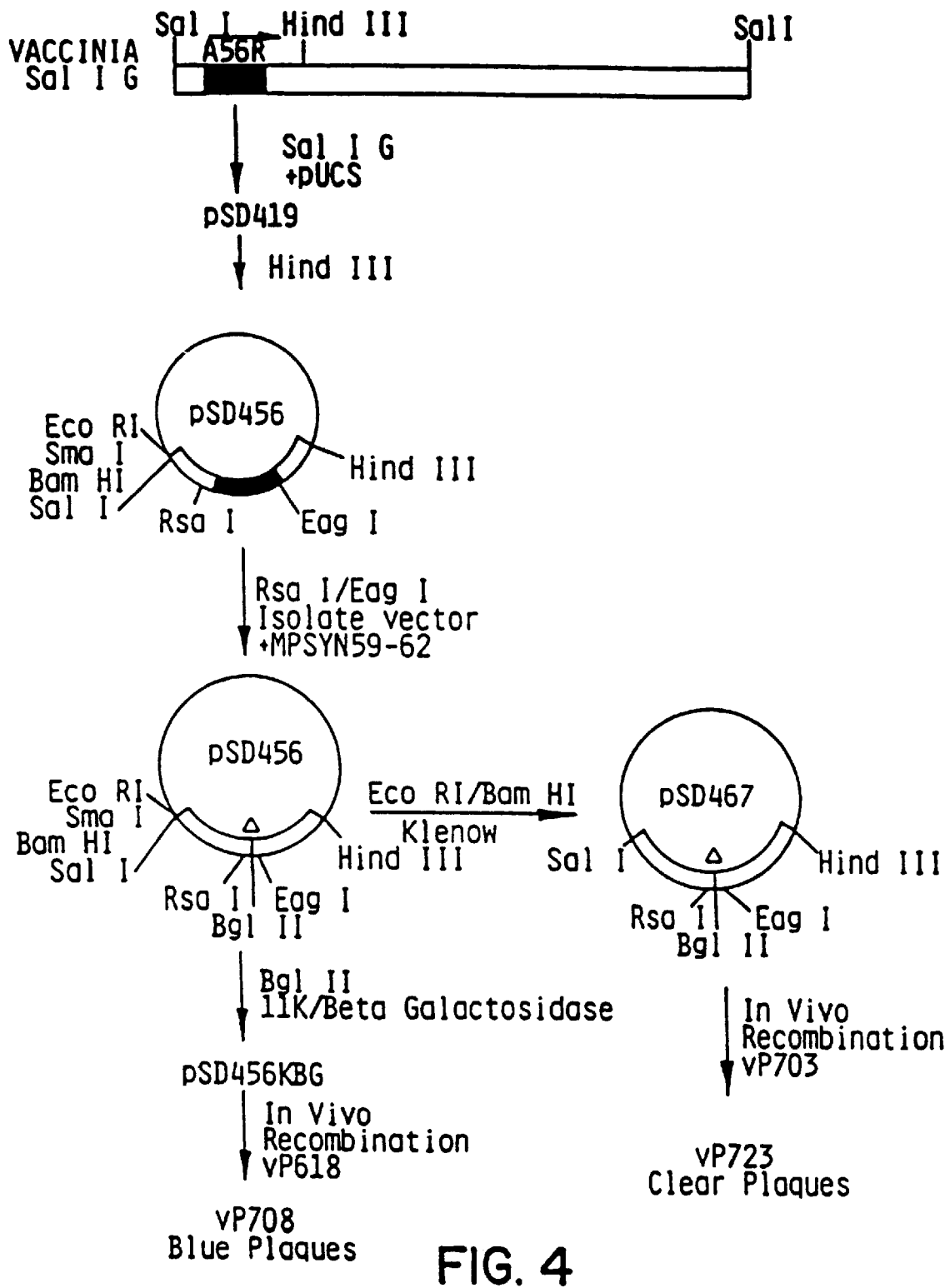
FIG. 4 schematically shows a method for the construction of plasmid pSD467 for deletion of hemagglutinin gene and generation of recombinant vaccinia virus vP723.

Referring now to FIG. 4, vaccinia SalI G restriction fragment (pos. 160,744–173,351) crosses the HindIII A/B junction (pos. 162,539). pSD419 contains vaccinia SalI G cloned into pUC8. The direction of transcription for the hemagglutinin (HA) gene is indicated by an arrow in FIG. 4. Vaccinia sequences derived from HindIII B were removed by digestion of pSD419 with HindIII within vaccinia sequences and at the pUC/vaccinia junction followed by ligation. The resulting plasmid, pSD456, contains the HA gene, A56R, flanked by 0.4 kb of vaccinia sequences to the left and 0.4 kb of vaccinia sequences to the right. A56R coding sequences were removed by cutting pSD456 with RsaI (partial; pos. 161,090) upstream from A56R coding sequences, and with EagI (pos. 162,054) near the end of the gene. The 3.6 kb RsaI/EagI vector fragment from pSD456 was isolated and ligated with annealed synthetic oligonucleotides MPSYN59 (SEQ ID NO:15), MPSYN62 (SEQ ID NO:16), MPSYN60 (SEQ ID NO:17), and MPSYN61 (SEQ ID NO:18)

```
             RsaI
MPSYN59  5'  ACACGAATGATTTTCTAAAGTATTTGGAAAGTTTTATAGGT-

MPSYN62  3'  TGTGCTTACTAAAAGATTTCATAAACCTTTCAAAATATCCA-

MPSYN59      AGTTGATAGAACAAAATACATAATTT 3'

MPSYN62      TCAACTATCT 5'

MPSYN60  5'                     TGTAAAAATAAATCACTTTTTATA-

MPSYN61  3'  TGTTTTATGTATTAAAACATTTTTATTTAGTGAAAAATAT-

BglII SmaI PstI EagI
MPSYN60      CTAAGATCTCCCGGGCTGCAGC           3'

MPSYN61      GATTCTAGAGGGCCCGACGTCGCCGG 5'
``` reconstructing the DNA sequences upstream from the A56R ORF and replacing the A56R ORF with a polylinker region as indicated above. The resulting plasmid is pSD466. The vaccinia deletion in pSD466 encompasses positions [161,185–162,053]. The site of the deletion in pSD466 is indicated by a triangle in FIG. 4.

A 3.2 kb BglII/BamHI (partial) cassette containing the E. coli Beta-galactosidase gene (Shapira et al., 1983) under the control of the vaccinia 11 kDa promoter (Bertholet et al., 1985; Guo et al., 1989) was inserted into the BglII site of pSD466, forming pSD466KBG. Plasmid pSD466KBG was used in recombination with rescuing virus vP618. Recombinant vaccinia virus, vP708, containing Beta-galactosidase in the A56R deletion, was isolated as a blue plaque in the presence of X-gal.

Beta-galactosidase sequences were deleted from vP708 using donor plasmid pSD467. pSD467 is identical to pSD466, except that EcoRI, SmaI and BamHI sites were removed from the pUC/vaccinia junction by digestion of pSD466 with EcoRI/BamHI followed by blunt ending with Klenow fragment of E. coli polymerase and ligation. Recombination between vP708 and pSD467 resulted in recombinant vaccinia deletion mutant, vP723, which was isolated as a clear plaque in the presence of X-gal.

EXAMPLE 5

CONSTRUCTION OF PLASMID pMPCSK1Δ FOR DELETION OF OPEN READING FRAMES [C7L–K1L]

Figure 5:
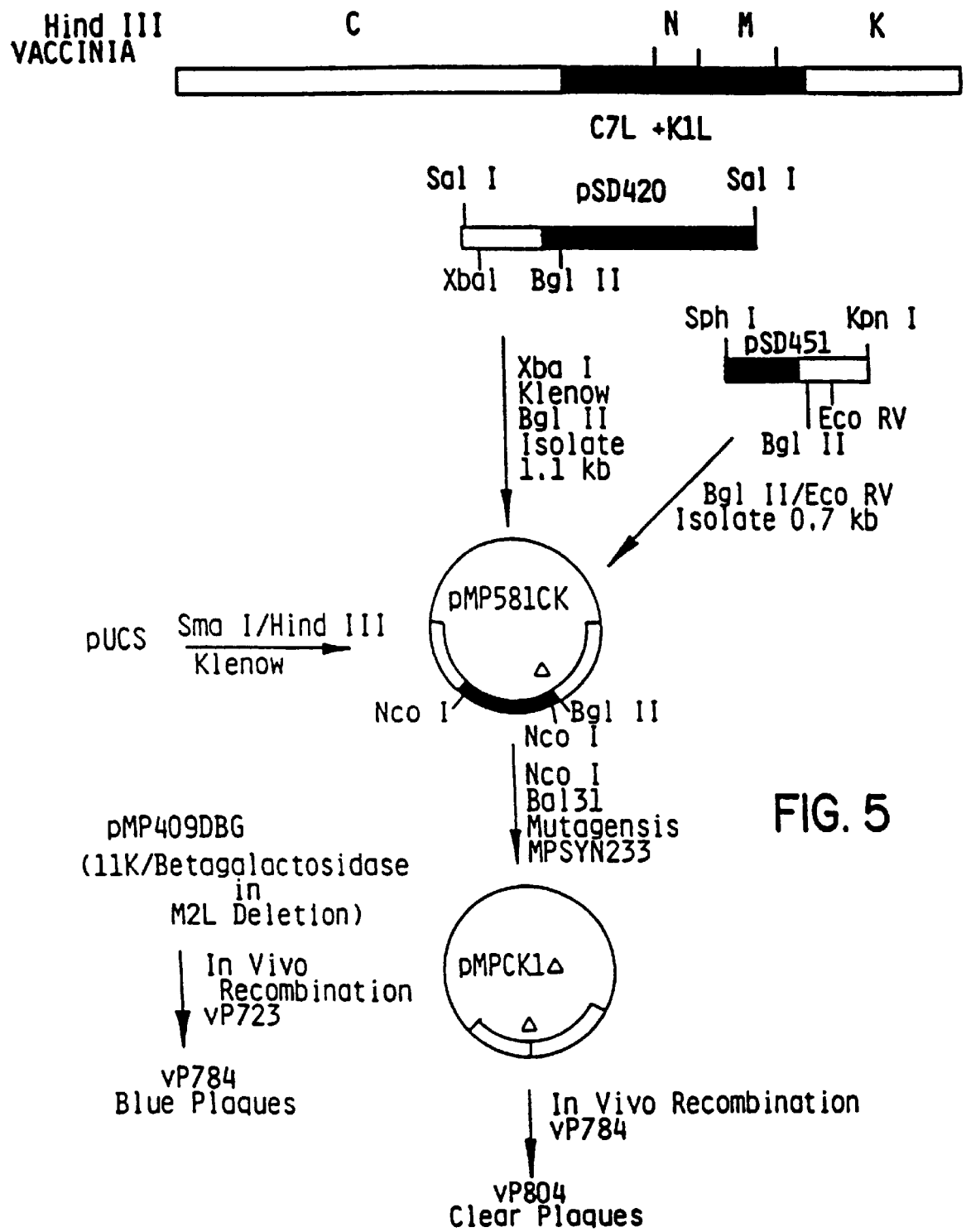
FIG. 5 schematically shows a method for the construction of plasmid pMPCK1Δ for deletion of gene cluster [C7L–K1L] and generation of recombinant vaccinia virus vP804.

Referring now to FIG. 5, the following vaccinia clones were utilized in the construction of pMPCSK1Δ. pSD420 is SalI H cloned into pUC8. pSD435 is KpnI F cloned into pUC18. pSD435 was cut with SphI and religated, forming pSD451. In pSD451, DNA sequences to the left of the SphI site (pos. 27,416) in HindIII M are removed (Perkus et al., 1990). pSD409 is HindIII M cloned into pUC8.

To provide a substrate for the deletion of the [C7L–K1L] gene cluster from vaccinia, E. coli Beta-galactosidase was first inserted into the vaccinia M2L deletion locus (Guo et al., 1990) as follows. To eliminate the BglII site in pSD409, the plasmid was cut with BglII in vaccinia sequences (pos. 28,212) and with BamHI at the pUC/vaccinia junction, then ligated to form plasmid pMP409B. pMP409B was cut at the unique SphI site (pos. 27,416). M2L coding sequences were removed by mutagenesis (Guo et al., 1990; Mandecki, 1986) using synthetic oligonucleotide

```
                                              BglII
MPSYN82 (SEQ ID NO:19) 5' TTTCTGTATATTTGCACCAATTTAGATCTT-

ACTCAAAATATGTAACAATA 3'
```

The resulting plasmid, pMP409D, contains a unique BglII site inserted into the M2L deletion locus as indicated above. A 3.2 kb BamHI (partial)/BglII cassette containing the E. coli Beta-galactosidase gene (Shapira et al., 1983) under the control of the 11 kDa promoter (Bertholet et al., 1985) was inserted into pMP409D cut with BglII. The resulting plasmid, pMP409DBG (Guo et al., 1990), was used as donor plasmid for recombination with rescuing vaccinia virus vP723. Recombinant vaccinia virus, vP784, containing Beta-galactosidase inserted into the M2L deletion locus, was isolated as a blue plaque in the presence of X-gal.

A plasmid deleted for vaccinia genes [C7L–K1L] was assembled in pUC8 cut with SmaI, HindIII and blunt ended with Klenow fragment of E. coli polymerase. The left flanking arm consisting of vaccinia HindIII C sequences was obtained by digestion of pSD420 with XbaI (pos. 18,628) followed by blunt ending with Klenow fragment of E. coli polymerase and digestion with BglII (pos. 19,706). The right flanking arm consisting of vaccinia HindIII K sequences was obtained by digestion of pSD451 with BglII (pos. 29,062) and EcoRV (pos. 29,778). The resulting plasmid, pMP581CK is deleted for vaccinia sequences between the BglII site (pos. 19,706) in HindIII C and the BglII site (pos. 29,062) in HindIII K. The site of the deletion of vaccinia sequences in plasmid pMP581CK is indicated by a triangle in FIG. 5.

To remove excess DNA at the vaccinia deletion junction, plasmid pMP581CK, was cut at the NcoI sites within vaccinia sequences (pos. 18,811; 19,655), treated with Bal-31 exonuclease and subjected to mutagenesis (Mandecki, 1986) using synthetic oligonucleotide MPSYN233 (SEQ ID NO:20) 5'-TGTCATTTAACACTATACTCATATTAAT-AAAAATAATATTTATT-3'. The resulting plasmid, pMPCSK1Δ, is deleted for vaccinia sequences positions 18,805–29,108, encompassing 12 vaccinia open reading frames [C7L–K1L]. Recombination between pMPCSK1Δ and the Beta-galactosidase containing vaccinia recombinant, vP784, resulted in vaccinia deletion mutant, vP804, which was isolated as a clear plaque in the presence of X-gal.

EXAMPLE 6

CONSTRUCTION OF PLASMID pSD548 FOR DELETION OF LARGE SUBUNIT, RIBONUCLEOTIDE REDUCTASE (I4L)

Figure 6:
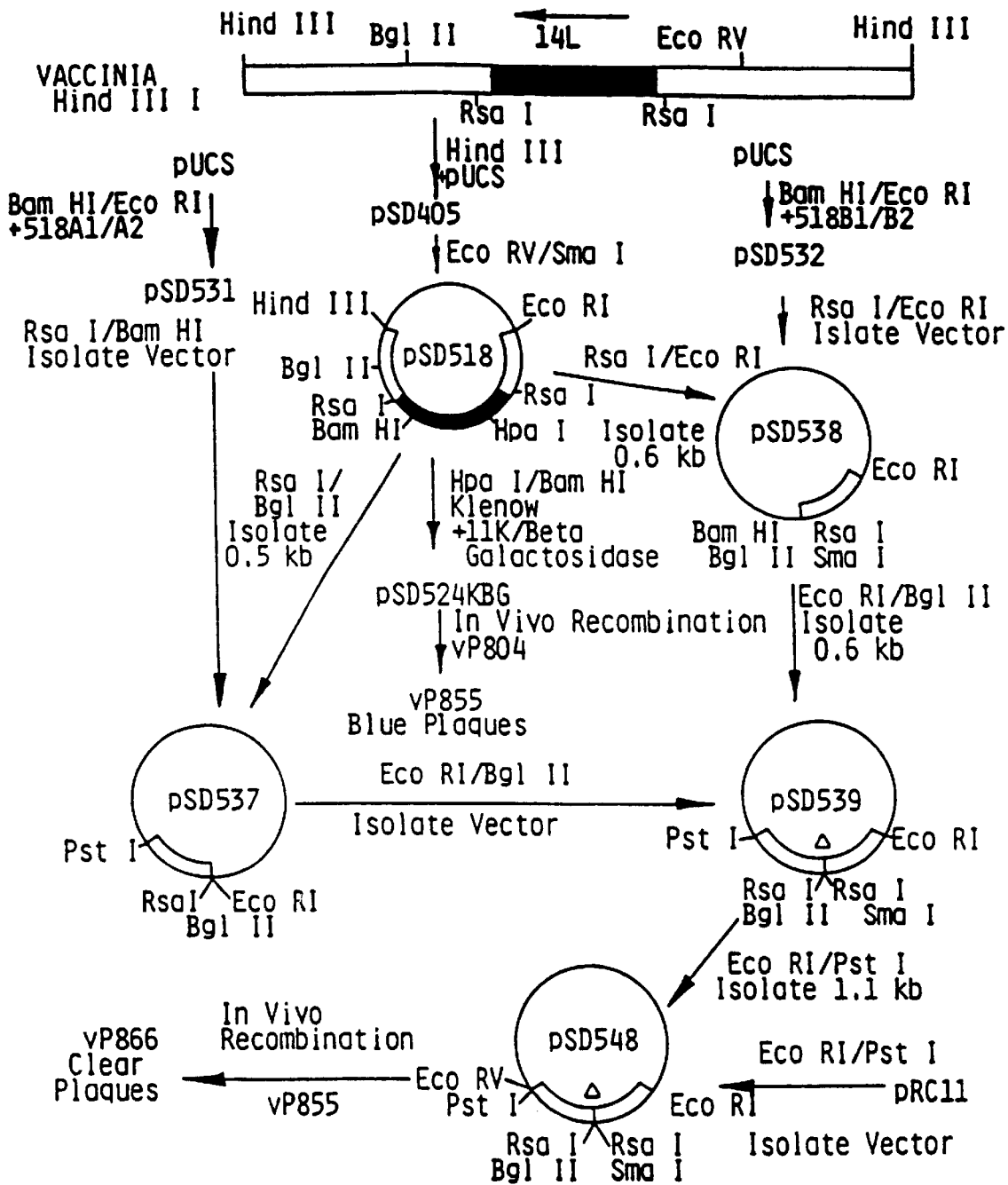
FIG. 6 schematically shows a method for the construction of plasmid pSD548 for deletion of large subunit, ribonucleotide reductase and generation of recombinant vaccinia virus vP866 (NYVAC)

Referring now to FIG. 6, plasmid pSD405 contains vaccinia HindIII I (pos. 63,875–70,367) cloned in pUC8. pSD405 was digested with EcoRV within vaccinia sequences (pos. 67,933) and with SmaI at the pUC/vaccinia junction, and ligated, forming plasmid pSD518. pSD518 was used as the source of all the vaccinia restriction fragments used in the construction of pSDS48.

The vaccinia I4L gene extends from position 67,371–65,059. Direction of transcription for I4L is indicated by an arrow in FIG. 6. To obtain a vector plasmid fragment deleted for a portion of the I4L coding sequences, pSD518 was digested with BamHI (pos. 65,381) and HpaI (pos. 67,001) and blunt ended using Klenow fragment of E. coli polymerase. This 4.8 kb vector fragment was ligated with a 3.2 kb SmaI cassette containing the E. coli Beta-galactosidase gene (Shapira et al., 1983) under the control of the vaccinia 11 kDa promoter (Bertholet et al., 1985; Perkus et al., 1990), resulting in plasmid pSD524KBG. pSD524KBG was used as donor plasmid for recombination with vaccinia virus vP804. Recombinant vaccinia virus, vP855, containing Beta-galactosidase in a partial deletion of the I4L gene, was isolated as a blue plaque in the presence of X-gal.

To delete Beta-galactosidase and the remainder of the I4L ORF from vP855, deletion plasmid pSD548 was constructed. The left and right vaccinia flanking arms were assembled separately in pUC8 as detailed below and presented schematically in FIG. 6.

To construct a vector plasmid to accept the left vaccinia flanking arm, pUC8 was cut with BamHI/EcoRI and ligated with annealed synthetic oligonucleotides 518A1/518A2 (SEQ ID NO:21/SEQ ID NO:22)

```
                BamHI    RsaI
    518A1   5'  GATCCTGAGTACTTTGTAATATAATGATATATATTTTCACTTTATCTCAT

518A2   3'          GACTCATGAAACATTATATTACTATATATAAAAGTGAAATAGAGTA

BglII    EcoRI
                TTGAGAATAAAAAGATCTTAGG         3'   518A1

AACTCTTATTTTTCTAGAATCCTTAA  5'     518A2
``` forming plasmid pSD531. pSD531 was cut with RsaI (partial) and BamHI and a 2.7 kb vector fragment isolated. pSD518 was cut with BglII (pos. 64,459)/ RsaI (pos. 64,994) and a 0.5 kb fragment isolated. The two fragments were ligated together, forming pSD537, which contains the complete vaccinia flanking arm left of the I4L coding sequences.

To construct a vector plasmid to accept the right vaccinia flanking arm, pUC8 was cut with BamHI/EcoRI and ligated with annealed synthetic oligonucleotides 518B1/518B2 (SEQ ID NO:23/SEQ ID NO:24)

```
                BamHI BglII SmaI
    518B1   5'  GATCCAGATCTCCCGGGAAAAAAATTATTTAACTTTTCATTAATAG-

518B2   3'         GTCTAGAGGGCCCTTTTTTTAATAAATTGAAAAGTAATTATC-

RsaI     EcoRI
          GGATTTGACGTATGTAGCGTACTAGG         3'   518B1

CCTAAACTGCATACTACGCATGATCCTTAA  5'      518B2
``` forming plasmid pSD532. pSD532 was cut with RsaI (partial)/EcoRI and a 2.7 kb vector fragment isolated. pSD518 was cut with RsaI within vaccinia sequences (pos. 67,436) and EcoRI at the vaccinia/pUC junction, and a 0.6 kb fragment isolated. The two fragments were ligated together, forming pSD538, which contains the complete vaccinia flanking arm to the right of I4L coding sequences.

The right vaccinia flanking arm was isolated as a 0.6 kb EcoRI/BglII fragment from pSD538 and ligated into pSD537 vector plasmid cut with EcoRI/BglII. In the resulting plasmid, pSD539, the I4L ORF (pos. 65,047–67,386) is replaced by a polylinker region, which is flanked by 0.6 kb vaccinia DNA to the left and 0.6 kb vaccinia DNA to the right, all in a pUC background. The site of deletion within vaccinia sequences is indicated by a triangle in FIG. 6. To avoid possible recombination of Beta-galactosidase sequences in the pUC-derived portion of pSD539 with Beta-galactosidase sequences in recombinant vaccinia virus vP855, the vaccinia I4L deletion cassette was moved from pSD539 into pRC11, a pUC derivative from which all Beta-galactosidase sequences have been removed and replaced with a polylinker region (Colinas et al., 1990). pSD539 was cut with EcoRI/PstI and the 1.2 kb fragment isolated. This fragment was ligated into pRC11 cut with EcoRI/PstI (2.35 kb), forming pSD548. Recombination between pSD548 and the Beta-galactosidase containing vaccinia recombinant, vP855, resulted in vaccinia deletion mutant vP866, which was isolated as a clear plaque in the presence of X-gal.

DNA from recombinant vaccinia virus vP866 was analyzed by restriction digests followed by electrophoresis on an agarose gel. The restriction patterns were as expected. Polymerase chain reactions (PCR) (Engelke et al., 1988) using vP866 as template and primers flanking the six deletion loci detailed above produced DNA fragments of the expected sizes. Sequence analysis of the PCR generated fragments around the areas of the deletion junctions confirmed that the junctions were as expected. Recombinant vaccinia virus vP866, containing the six engineered deletions as described above, was designated vaccinia vaccine strain "NYVAC."

EXAMPLE 7

INSERTION OF A RABIES GLYCOPROTEIN G GENE INTO NYVAC

The gene encoding rabies glycoprotein G under the control of the vaccinia H6 promoter (Taylor et al., 1988a,b) was inserted into TK deletion plasmid pSD513. pSD513 is identical to plasmid pSD460 (FIG. 1) except for the presence of a polylinker region.

Figure 7:
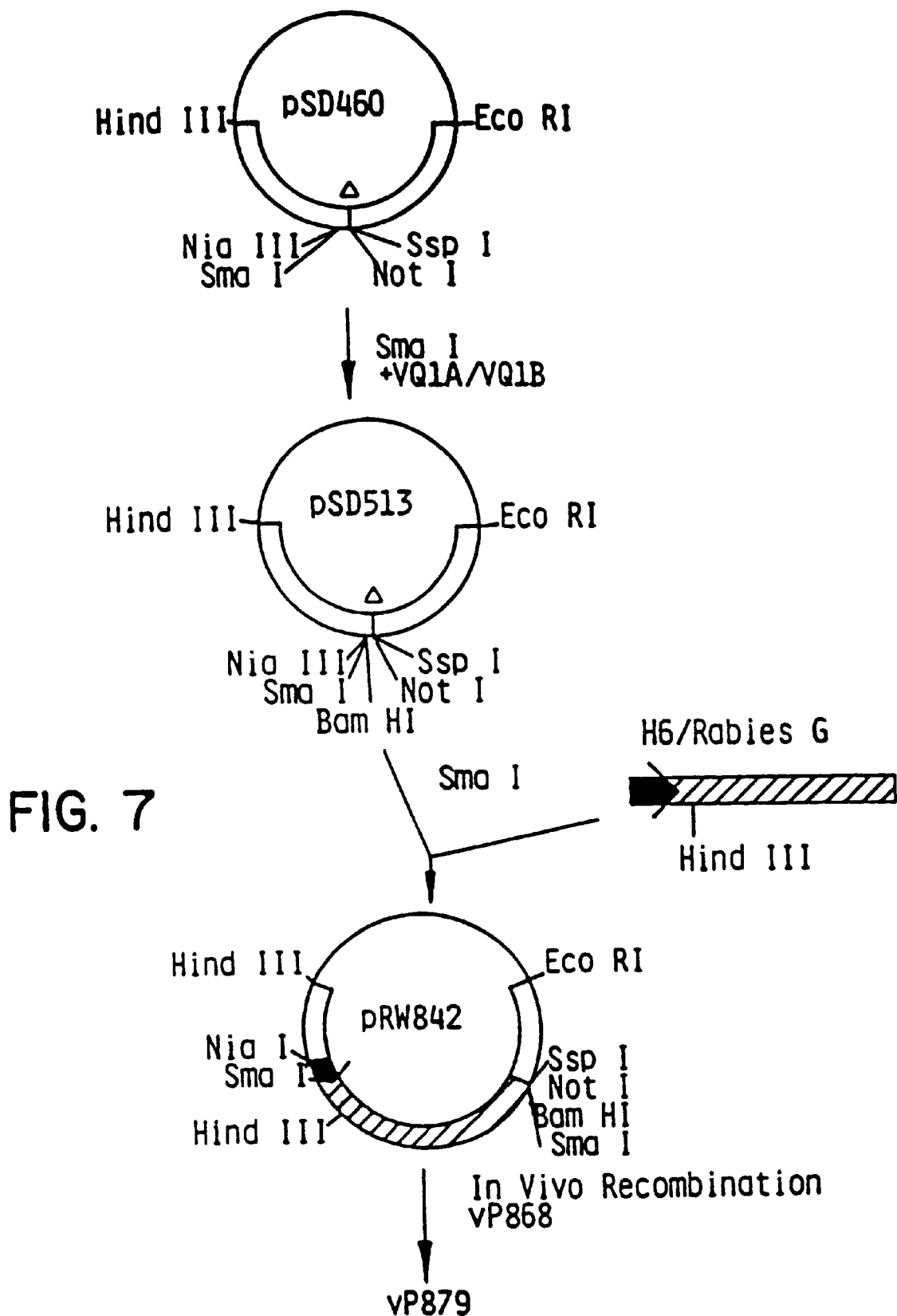
FIG. 7 schematically shows a method for the construction of plasmid pRW842 for insertion of rabies glycoprotein G gene into the TK deletion locus and generation of recombinant vaccinia virus vP879.

Referring now to FIG. 7, the polylinker region was inserted by cutting pSD460 with SmaI and ligating the plasmid vector with annealed synthetic oligonucleotides VQ1A/VQ1B (SEQ ID NO:25/SEQ ID NO:26)

```
             SmaI  BglII  XhoI   PstI   NarI   BamHI
   VQ1A  5'  GGGAGATCTCTCGAGCTGCAGGGCGCCGGATCCTTTTTCT        3'

VQ1B  3'      CCCTCTAGAGAGCTCGACGTCCCGCGGCCTAGGAAAAAGA     5'
``` to form vector plasmid pSD513. pSD513 was cut with SmaI and ligated with a SmaI ended 1.8 kb cassette containing the gene encoding the rabies glycoprotein G gene under the control of the vaccinia H6 promoter (Taylor et al., 1988a,b). The resulting plasmid was designated pRW842. pRW842 was used as donor plasmid for recombination with NYVAC rescuing virus (vP866). Recombinant vaccinia virus vP879 was identified by plaque hybridization using $^{32}$P-labelled DNA probe to rabies glycoprotein G coding sequences.

The modified recombinant viruses of the present invention provide advantages as recombinant vaccine vectors. The attenuated virulence of the vector advantageously reduces the opportunity for the possibility of a runaway infection due to vaccination in the vaccinated individual and also diminishes transmission from vaccinated to unvaccinated individuals or contamination of the environment.

The modified recombinant viruses are also advantageously used in a method for expressing a gene product in a cell cultured in vitro by introducing into the cell the modified recombinant virus having foreign DNA which codes for and expresses gene products in the cell.

EXAMPLE 8

CONSTRUCTION OF ALVAC RECOMBINANTS EXPRESSING RABIES VIRUS GLYCOPROTEIN G

This example describes the development of ALVAC, a canarypox virus vector and, of a canarypox-rabies recombinant designated as ALVAC-RG (vCP65) and its safety and efficacy.

Cells and Viruses. The parental canarypox virus (Rentschler strain) is a vaccinal strain for canaries. The vaccine strain was obtained from a wild type isolate and attenuated through more than 200 serial passages on chick embryo fibroblasts. A master viral seed was subjected to four successive plaque purifications under agar and one plaque clone was amplified through five additional passages after which the stock virus was used as the parental virus in in vitro recombination tests. The plaque purified canarypox isolate is designated ALVAC.

Construction of a Canarypox Insertion Vector. An 880 bp canarypox PvuII fragment was cloned between the PvuII sites of pUC9 to form pRW764.5. The sequence of this fragment is shown in FIG. 8 (SEQ ID NO:27) between positions 1372 and 2251. The limits of an open reading frame designated as C5 were defined.

It was determined that the open reading frame was initiated at position 166 within the fragment and terminated at position 487. The C5 deletion was made without interruption of open reading frames. Bases from position 167 through position 455 were replaced with the sequence (SEQ ID NO:28) GCTTCCCGGGAATTCTAGCTAGCTAGTTT. This replacement sequence contains HindIII, SmaI and EcoRI insertion sites followed by translation stops and a transcription termination signal recognized by vaccinia virus RNA polymerase (Yuen et al., 1987). Deletion of the C5 ORF was performed as described below. Plasmid pRW764.5 was partially cut with RsaI and the linear product was isolated. The RsaI linear fragment was recut with BglII and the pRW764.5 fragment now with a RsaI to BglII deletion from position 156 to position 462 was isolated and used as a vector for the following synthetic oligonucleotides:

RW145 (SEQ ID NO:29):
ACTCTCAAAAGCTTCCCGGGAAT-
TCTAGCTAGCTAGTTTTTATAAA

RW146 (SEQ ID NO:30):
GATCTTTATAAAAACTAGCTAGCTA-
GAATTCCCGGGAAGCTTTTGAGAGT

Oligonucleotides RW145 and RW146 were annealed and inserted into the pRW 764.5 RsaI and BglII vector described above. The resulting plasmid is designated pRW831.

Construction of Insertion Vector Containing the Rabies G Gene. Construction of pRW838 is illustrated below. Oligonucleotides A through E, which overlap the translation initiation codon of the H6 promoter with the ATG of rabies G, were cloned into pUC9 as pRW737. Oligonucleotides A through E contain the H6 promoter, starting at NruI, through the HindIII site of rabies G followed by BglII. Sequences of oligonucleotides A through E ((SEQ ID NO:31)–(SEQ ID NO:35)) are:

A (SEQ ID NO:31): CTGAAATTATTTCATTATCGCGATATCCGTTAA

GTTTGTATCGTAATGGTTCCTCAGGCTCTCCTGTTTGT

B (SEQ ID NO:32): CATTACGATACAAACTTAACGGATATCGCGATAA

TGAAATAATTTCAG

C (SEQ ID NO:33): ACCCCTTCTGGTTTTTCCGTTGTGTTTTGGGAAA

TTCCCTATTTACACGATCCCAGACAAGCTTAGATCTCAG

D (SEQ ID NO:34): CTGAGATCTAAGCTTGTCTGGGATCGTGTAAATA

GGGAATTTCCCAAAACA

E (SEQ ID NO:35): CAACGGAAAAACCAGAAGGGGTACAAACAGGAGA

GCCTGAGGAAC

The diagram of annealed oligonucleotides A through E is as follows:

```
                    A                              C
----------------------------|----------------------------
        ----------------|--------------------|----------------
                    B               E               D
```

Oligonucleotides A through E were kinased, annealed (95° C. for 5 minutes, then cooled to room temperature), and inserted between the PvuII sites of pUC9. The resulting plasmid, pRW737, was cut with HindIII and BglII and used as a vector for the 1.6 kbp HindIII-BglII fragment of ptg155PRO (Kieny et al., 1984) generating pRW739. The ptg155PRO HindIII site is 86 bp downstream of the rabies G translation initiation codon. BglII is downstream of the rabies G translation stop codon in ptg155PRO. pRW739 was partially cut with NruI, completely cut with BglII, and a 1.7 kbp NruI-BglII fragment, containing the 3' end of the H6 promoter previously described (Taylor et al., 1988a,b; Guo et al., 1989; Perkus et al., 1989) through the entire rabies G gene, was inserted between the NruI and BamHI sites of pRW824. The resulting plasmid is designated pRW832. Insertion into pRW824 added the H6 promoter 5' of NruI.

The pRW824 sequence of BamHI followed by SmaI is (SEQ ID NO:36): GGATCCCCGGG. pRW824 is a plasmid that contains a nonpertinent gene linked precisely to the vaccinia virus H6 promoter. Digestion with NruI and BamHI completely excised this nonpertinent gene. The 1.8 kbp pRW832 SmaI fragment, containing H6 promoted rabies G, was inserted into the SmaI of pRW831, to form plasmid pRW838.

Development of ALVAC-RG. Plasmid pRW838 was transfected into ALVAC infected primary CEF cells by using the calcium phosphate precipitation method previously described (Panicali et al., 1982; Piccini et al., 1987). Positive plaques were selected on the basis of hybridization to a specific rabies G probe and subjected to 6 sequential rounds of plaque purification until a pure population was achieved. One representative plaque was then amplified and the resulting ALVAC recombinant was designated ALVAC-RG (vCP65) (see also FIGS. 9A and 9B). The correct insertion of the rabies G gene into the ALVAC genome without subsequent mutation was confirmed by sequence analysis.

Immunofluorescence. During the final stages of assembly of mature rabies virus particles, the glycoprotein component is transported from the golgi apparatus to the plasma membrane where it accumulates with the carboxy terminus extending into the cytoplasm and the bulk of the protein on the external surface of the cell membrane. In order to confirm that the rabies glycoprotein expressed in ALVAC-RG was correctly presented, immunofluorescence was performed on primary CEF cells infected with ALVAC or ALVAC-RG. Immunofluorescence was performed as previously described (Taylor et al., 1990) using a rabies G monoclonal antibody. Strong surface fluorescence was detected on CEF cells infected with ALVAC-RG but not with the parental ALVAC.

Immunoprecipitation. Preformed monolayers of primary CEF, Vero (a line of African Green monkey kidney cells ATCC # CCL81) and MRC-5 cells (a fibroblast-like cell line derived from normal human fetal lung tissue ATCC # CCL171) were inoculated at 10 pfu per cell with parental virus ALVAC and recombinant virus ALVAC-RG in the presence of radiolabelled $^{35}$S-methionine and treated as previously described (Taylor et al., 1990). Immunoprecipitation reactions were performed using a rabies G specific monoclonal antibody. Efficient expression of a rabies specific glycoprotein with a molecular weight of approximately 67 kDa was detected with the recombinant ALVAC-RG. No rabies specific products were detected in uninfected cells or cells infected with the parental ALVAC virus.

Sequential Passaging Experiment. In studies with ALVAC virus in a range of non-avian species no proliferative infection or overt disease was observed (Taylor et al., 1991b). However, in order to establish that neither the parental nor recombinant virus could be adapted to grow in non-avian cells, a sequential passaging experiment was performed.

The two viruses, ALVAC and ALVAC-RG, were inoculated in 10 sequential blind passages in three cell substrates:

(1) Primary chick embryo fibroblast (CEF) cells produced from 11 day old white leghorn embryos;
(2) Vero cells—a continuous line of African Green monkey kidney cells (ATCC # CCL81); and
(3) MRC-5 cells—a diploid cell line derived from human fetal lung tissue (ATCC # CCL171).

The initial inoculation was performed at an m.o.i. of 0.1 pfu per cell using three 60 mm dishes of each cell substrate containing $2\times10^6$ cells per dish. One dish was inoculated in the presence of 40 µg/ml of Cytosine arabinoside (Ara C), an inhibitor of DNA replication. After an absorption period of 1 hour at 37° C., the inoculum was removed and the monolayer washed to remove unabsorbed virus. At this time the medium was replaced with 5 ml of EMEM+2% NBCS on two dishes (samples t0 and t7) and 5 ml of EMEM+2% NBCS containing 40 µg/ml Ara C on the third (sample t7A). Sample t0 was frozen at −70° C. to provide an indication of the residual input virus. Samples t7 and t7A were incubated at 37° C. for 7 days, after which time the contents were harvested and the cells disrupted by indirect sonication.

One ml of sample t7 of each cell substrate was inoculated undiluted onto three dishes of the same cell substrate (to provide samples t0, t7 and t7A) and onto one dish of primary CEF cells. Samples t0, t7 and t7A were treated as for passage one. The additional inoculation on CEF cells was included to provide an amplification step for more sensitive detection of virus which might be present in the non-avian cells.

This procedure was repeated for 10 (CEF and MRC-5) or 8 (Vero) sequential blind passages. Samples were then frozen and thawed three times and assayed by titration on primary CEF monolayers.

Virus yield in each sample was then determined by plaque titration on CEF monolayers under agarose. Summarized results of the experiment are shown in Tables 1 and 2.

The results indicate that both the parental ALVAC and the recombinant ALVAC-RG are capable of sustained replication on CEF monolayers with no loss of titer. In Vero cells, levels of virus fell below the level of detection after 2 passages for ALVAC and 1 passage for ALVAC-RG. In MRC-5 cells, a similar result was evident, and no virus was detected after 1 passage. Although the results for only four passages are shown in Tables 1 and 2 the series was continued for 8 (Vero) and 10 (MRC-5) passages with no detectable adaptation of either virus to growth in the non-avian cells.

In passage 1 relatively high levels of virus were present in the t7 sample in MRC-5 and Vero cells. However this level of virus was equivalent to that seen in the t0 sample and the t7A sample incubated in the presence of Cytosine arabinoside in which no viral replication can occur. This demonstrated that the levels of virus seen at 7 days in non-avian cells represented residual virus and not newly replicated virus.

In order to make the assay more sensitive, a portion of the 7 day harvest from each cell substrate was inoculated onto a permissive CEF monolayer and harvested at cytopathic effect (CPE) or at 7 days if no CPE was evident. The results of this experiment are shown in Table 3. Even after amplification through a permissive cell substrate, virus was only detected in MRC-5 and Vero cells for two additional passages. These results indicated that under the conditions used, there was no adaptation of either virus to growth in Vero or MRC-5 cells.

Inoculation of Macaques. Four HIV seropositive macaques were initially inoculated with ALVAC-RG as described in Table 4. After 100 days these animals were re-inoculated to determine a booster effect, and an additional seven animals were inoculated with a range of doses. Blood was drawn at appropriate intervals and sera analyzed, after heat inactivation at 56° C. for 30 minutes, for the presence of anti-rabies antibody using the Rapid Fluorescent Focus Inhibition Assay (Smith et al., 1973).

Inoculation of Chimpanzees. Two adult male chimpanzees (50 to 65 kg weight range) were inoculated intramuscularly or subcutaneously with $1\times10^7$ pfu of vCP65. Animals were monitored for reactions and bled at regular intervals for analysis for the presence of anti-rabies antibody with the RFFI test (Smith et al., 1973). Animals were re-inoculated with an equivalent dose 13 weeks after the initial inoculation.

Inoculation of Mice. Groups of mice were inoculated with 50 to 100 μl of a range of dilutions of different batches of vCP65. Mice were inoculated in the footpad. On day 14, mice were challenged by intracranial inoculation of from 15 to 43 mouse $LD_{50}$ of the virulent CVS strain of rabies virus. Survival of mice was monitored and a protective dose 50% ($PD_{50}$) calculated at 28 days post-inoculation.

Inoculation of Dogs and Cats. Ten beagle dogs, 5 months old, and 10 cats, 4 months old, were inoculated subcutaneously with either 6.7 or 7.7 $\log_{10}$ $TCID_{50}$ of ALVAC-RG. Four dogs and four cats were not inoculated. Animals were bled at 14 and 28 days post-inoculation and anti-rabies antibody assessed in an RFFI test. The animals receiving 6.7 $\log_{10}$ $TCID_{50}$ of ALVAC-RG were challenged at 29 days post-vaccination with 3.7 $\log_{10}$ mouse $LD_{50}$ (dogs) or 4.3 $\log_{10}$ mouse $LD_{50}$ (cats) of the NYGS rabies virus challenge strain.

Inoculation of Squirrel Monkeys. Three groups of four squirrel monkeys (*Saimiri sciureus*) were inoculated with one of three viruses (a) ALVAC, the parental canarypox virus, (b) ALVAC-RG, the recombinant expressing the rabies G glycoprotein or (c) vCP37, a canarypox recombinant expressing the envelope glycoprotein of feline leukemia virus. Inoculations were performed under ketamine anaesthesia. Each animal received at the same time: (1) 20 μl instilled on the surface of the right eye without scarification; (2) 100 μl as several droplets in the mouth; (3) 100 μl in each of two intradermal injection sites in the shaven skin of the external face of the right arm; and (4) 100 μl in the anterior muscle of the right thigh.

Four monkeys were inoculated with each virus, two with a total of 5.0 $\log_{10}$ pfu and two with a total of 7.0 $\log_{10}$ pfu. Animals were bled at regular intervals and sera analyzed for the presence of antirabies antibody using an RFFI test (Smith et al., 1973). Animals were monitored daily for reactions to vaccination. Six months after the initial inoculation the four monkeys receiving ALVAC-RG, two monkeys initially receiving vCP37, and two monkeys initially receiving ALVAC, as well as one naive monkey were inoculated with 6.5 $\log_{10}$ pfu of ALVAC-RG subcutaneously. Sera were monitored for the presence of rabies neutralizing antibody in an RFFI test (Smith et al., 1973).

Inoculation of Human Cell Lines with ALVAC-RG. In order to determine whether efficient expression of a foreign gene could be obtained in non-avian cells in which the virus does not productively replicate, five cell types, one avian and four non-avian, were analyzed for virus yield, expression of the foreign rabies G gene and viral specific DNA accumulation. The cells inoculated were:

(a) Vero, African Green monkey kidney cells, ATCC # CCL81;

(b) MRC-5, human embryonic lung, ATCC # CCL 171;

(c) WISH human amnion, ATCC # CCL 25;

(d) Detroit-532, human foreskin, Downs's syndrome, ATCC # CCL 54; and (e) Primary CEF cells.

Chicken embryo fibroblast cells produced from 11 day old white leghorn embryos were included as a positive control. All inoculations were performed on preformed monolayers of $2\times10^6$ cells as discussed below.

A. Methods for DNA analysis.

Three dishes of each cell line were inoculated at 5 pfu/cell of the virus under test, allowing one extra dish of each cell line un-inoculated. One dish was incubated in the presence of 40 μg/ml of cytosine arabinoside (Ara C). After an adsorption period of 60 minutes at 37° C., the inoculum was removed and the monolayer washed twice to remove unadsorbed virus. Medium (with or without Ara C) was then replaced. Cells from one dish (without Ara C) were harvested as a time zero sample. The remaining dishes were incubated at 37° C. for 72 hours, at which time the cells were harvested and used to analyze DNA accumulation. Each sample of $2\times10^6$ cells was resuspended in 0.5 ml phosphate buffered saline (PBS) containing 40 mM EDTA and incubated for 5 minutes at 37° C. An equal volume of 1.5% agarose prewarmed at 42° C. and containing 120 mM EDTA was added to the cell suspension and gently mixed. The suspension was transferred to an agarose plug mold and allowed to harden for at least 15 min. The agarose plugs were then removed and incubated for 12–16 hours at 50° C. in a volume of lysis buffer (1% sarkosyl, 100 μg/ml proteinase K, 10 mM Tris HCl pH 7.5, 200 mM EDTA) that completely covers the plug. The lysis buffer was then replaced with 5.0 ml sterile 0.5×TBE (44.5 mM Tris-borate, 44.5 mM boric acid, 0.5 mM EDTA) and equilibrated at 4° C. for 6 hours with 3 changes of TBE buffer. The viral DNA within the plug was fractionated from cellular RNA and DNA using a pulse field electrophoresis system. Electrophoresis was performed for 20 hours at 180 V with a ramp of 50–90 sec at 15° C. in 0.5×TBE. The DNA was run with lambda DNA molecular weight standards. After electrophoresis the viral DNA band was visualized by staining with ethidium bromide. The DNA was then transferred to a nitrocellulose membrane and probed with a radiolabelled probe prepared from purified ALVAC genomic DNA.

B. Estimation of virus yield.

Dishes were inoculated exactly as described above, with the exception that input multiplicity was 0.1 pfu/cell. At 72 hours post infection, cells were lysed by three successive cycles of freezing and thawing. Virus yield was assessed by plaque titration on CEF monolayers.

C. Analysis of expression of Rabies G gene.

Dishes were inoculated with recombinant or parental virus at a multiplicity of 10 pfu/cell, allowing an additional dish-as an uninfected virus control. After a one hour absorption period, the medium was removed and replaced with methionine free medium. After a 30 minute period, this medium was replaced with methionine-free medium containing 25 uCi/ml of $^{35}S$-Methionine. Infected cells were labelled overnight (approximately 16 hours), then lysed by the addition of buffer A lysis buffer. Immunoprecipitation was performed as previously described (Taylor et al., 1990) using a rabies G specific monoclonal antibody.

Results: Estimation of Viral Yield. The results of titration for yield at 72 hours after inoculation at 0.1 pfu per cell are shown in Table 5. The results indicate that while a productive infection can be attained in the avian cells, no increase in virus yield can be detected by this method in the four non-avian cell systems.

Analysis of Viral DNA Accumulation. In order to determine whether the block to productive viral replication in the non-avian cells occurred before or after DNA replication, DNA from the cell lysates was fractionated by electrophoresis, transferred to nitrocellulose and probed for the presence of viral specific DNA. DNA from uninfected CEF cells, ALVAC-RG infected CEF cells at time zero, ALVAC-RG infected CEF cells at 72 hours post-infection and ALVAC-RG infected CEF cells at 72 hours post-infection in the presence of 40 μg/ml of cytosine arabinoside all showed some background activity, probably due to contaminating CEF cellular DNA in the radiolabelled ALVAC DNA probe preparation. However, ALVAC-RG infected CEF cells at 72 hours post-infection exhibited a strong band in the region of approximately 350 kbp representing ALVAC-specific viral DNA accumulation. No such band is detectable when the culture is incubated in the presence of the DNA synthesis inhibitor, cytosine arabinoside. Equivalent samples produced in Vero cells showed a very faint band at approximately 350 kbp in the ALVAC-RG infected Vero cells at time zero. This level represented residual virus. The intensity of the band was amplified at 72 hours post-infection indicating that some level of viral specific DNA replication had occurred in Vero cells which had not resulted in an increase in viral progeny. Equivalent samples produced in MRC-5 cells indicated that no viral specific DNA accumulation was detected under these conditions in this cell line. This experiment was then extended to include additional human cell lines, specifically WISH and Detroit-532 cells. ALVAC infected CEF cells served as a positive control. No viral specific DNA accumulation was detected in either WISH or Detroit cells inoculated with ALVAC-RG. It should be noted that the limits of detection of this method have not been fully ascertained and viral DNA accumulation may be occurring, but at a level below the sensitivity of the method. Other experiments in which viral DNA replication was measured by $^3$H-thymidine incorporation support the results obtained with Vero and MRC-5 cells.

Analysis of Rabies Gene Expression. To determine if any viral gene expression, particularly that of the inserted foreign gene, was occurring in the human cell lines even in the absence of viral DNA replication, immunoprecipitation experiments were performed on $^{35}$S-methionine labelled lysates of avian and non-avian cells infected with ALVAC and ALVAC-RG. The results of immunoprecipitation using a rabies G specific monoclonal antibody illustrated specific immunoprecipitation of a 67 kDa glycoprotein in CEF, Vero and MRC-5, WISH and Detroit cells infected with ALVAC-RG. No such specific rabies gene products were detected in any of the uninfected and parentally infected cell lysates.

The results of this experiment indicated that in the human cell lines analyzed, although the ALVAC-RG recombinant was able to initiate an infection and express a foreign gene product under the transcriptional control of the H6 early/late vaccinia virus promoter, the replication did not proceed through DNA replication, nor was there any detectable viral progeny produced. In the Vero cells, although some level of ALVAC-RG specific DNA accumulation was observed, no viral progeny was detected by these methods. These results would indicate that in the human cell lines analyzed the block to viral replication occurs prior to the onset of DNA replication, while in Vero cells, the block occurs following the onset of viral DNA replication.

In order to determine whether the rabies glycoprotein expressed in ALVAC-RG was immunogenic, a number of animal species were tested by inoculation of the recombinant. The efficacy of current rabies vaccines is evaluated in a mouse model system. A similar test was therefore performed using ALVAC-RG. Nine different preparations of virus (including one vaccine batch (J) produced after 10 serial tissue culture passages of the seed virus) with infectious titers ranging from 6.7 to 8.4 $\log_{10}$ TCID$_{50}$ per ml were serially diluted and 50 to 100 μl of dilutions inoculated into the footpad of four to six week old mice. Mice were challenged 14 days later by the intracranial route with 300 μl of the CVS strain of rabies virus containing from 15 to 43 mouse LD$_{50}$ as determined by lethality titration in a control group of mice. Potency, expressed as the PD$_{50}$ (Protective dose 50%), was calculated at 14 days post-challenge. The results of the experiment are shown in Table 6. The results indicated that ALVAC-RG was consistently able to protect mice against rabies virus challenge with a PD$_{50}$ value ranging from 3.33 to 4.56 with a mean value of 3.73 (STD 0.48). As an extension of this study, male mice were inoculated intracranially with 50 μl of virus containing 6.0 $\log_{10}$ TCID$_{50}$ of ALVAC-RG or with an equivalent volume of an uninfected cell suspension. Mice were sacrificed on days 1, 3 and 6 post-inoculation and their brains removed, fixed and sectioned. Histopathological examination showed no evidence for neurovirulence of ALVAC-RG in mice.

In order to evaluate the safety and efficacy of ALVAC-RG for dogs and cats, a group of 14, 5 month old beagles and 14, 4 month old cats were analyzed. Four animals in each species were not vaccinated. Five animals received 6.7 $\log_{10}$ TCID$_{50}$ subcutaneously and five animals received 7.7 $\log_{10}$ TCID$_{50}$ by the same route. Animals were bled for analysis for anti-rabies antibody. Animals receiving no inoculation or 6.7 $\log_{10}$ TCID$_{50}$ of ALVAC-RG were challenged at 29 days post-vaccination with 3.7 $\log_{10}$ mouse LD$_{50}$ (dogs, in the temporal muscle) or 4.3 $\log_{10}$ mouse LD$_{50}$ (cats, in the neck) of the NYGS rabies virus challenge strain. The results of the experiment are shown in Table 7.

No adverse reactions to inoculation were seen in either cats or dogs with either dose of inoculum virus. Four of 5 dogs immunized with 6.7 $\log_{10}$ TCID$_{50}$ had antibody titers on day 14 post-vaccination and all dogs had titers at 29 days. All dogs were protected from a challenge which killed three out of four controls. In cats, three of five cats receiving 6.7 $\log_{10}$ TCID$_{50}$ had specific antibody titers on day 14 and all cats were positive on day 29 although the mean antibody titer was low at 2.9 IU. Three of five cats survived a challenge which killed all controls. All cats immunized with 7.7 $\log_{10}$ TCID$_{50}$ had antibody titers on day 14 and at day 29 the Geometric Mean Titer was calculated as 8.1 International Units.

The immune response of squirrel monkeys (*Saimiri sciureus*) to inoculation with ALVAC, ALVAC-RG and an unrelated canarypox virus recombinant was examined. Groups of monkeys were inoculated as described above and sera analyzed for the presence of rabies specific antibody. Apart from minor typical skin reactions to inoculation by the intradermal route, no adverse reactivity was seen in any of the monkeys. Small amounts of residual virus were isolated from skin lesions after intradermal inoculation on days two and four post-inoculation only. All specimens were negative on day seven and later. There was no local reaction to intra-muscular injection. All four monkeys inoculated with ALVAC-RG developed anti-rabies serum neutralizing antibodies as measured in an RFFI test. Approximately six months after the initial inoculation all monkeys and one additional naive monkey were re-inoculated by the subcutaneous route on the external face of the left thigh with 6.5 $\log_{10}$ TCID$_{50}$ of ALVAC-RG. Sera were analyzed for the presence of anti-rabies antibody. The results are shown in Table 8.

Four of the five monkeys naive to rabies developed a serological response by seven days post-inoculation with ALVAC-RG. All five monkeys had detectable antibody by 11 days post-inoculation. of the four monkeys with previous exposure to the rabies glycoprotein, all showed a significant increase in serum neutralization titer between days 3 and 7 post-vaccination. The results indicate that vaccination of squirrel monkeys with ALVAC-RG does not produce adverse side-effects and a primary neutralizing antibody response can be induced. An anamnestic response is also induced on re-vaccination. Prior exposure to ALVAC or to a canarypox recombinant expressing an unrelated foreign gene does not interfere with induction of an anti-rabies immune response upon re-vaccination.

The immunological response of HIV-2 seropositive macaques to inoculation with ALVAC-RG was assessed. Animals were inoculated as described above and the presence of anti-rabies serum neutralizing antibody assessed in an RFFI test. The results, shown in Table 9, indicated that HIV-2 positive animals inoculated by the subcutaneous route developed anti-rabies antibody by 11 days after one inoculation. An anamnestic response was detected after a booster inoculation given approximately three months after the first inoculation. No response was detected in animals receiving the recombinant by the oral route. In addition, a series of six animals were inoculated with decreasing doses of ALVAC-RG given by either the intra-muscular or subcutaneous routes. Five of the six animals inoculated responded by 14 days post-vaccination with no significant difference in antibody titer.

Two chimpanzees with prior exposure to HIV were inoculated with 7.0 $\log_{10}$ pfu of ALVAC-RG by the subcutaneous or intra-muscular route. At 3 months post-inoculations both animals were re-vaccinated in an identical fashion. The results are shown in Table 10.

No adverse reactivity to inoculation was noted by either intramuscular or subcutaneous routes. Both chimpanzees responded to primary inoculation by 14 days and a strongly rising response was detected following re-vaccination.

TABLE 1

Sequential Passage of ALVAC in Avian and non-Avian Cells.

|  | CEF | Vero | MRC-5 |
|---|---|---|---|
| Pass 1 Sample |  |  |  |
| t0[a] | 2.4 | 3.0 | 2.6 |
| t7[b] | 7.0 | 1.4 | 0.4 |
| t7A[c] | 1.2 | 1.2 | 0.4 |
| Pass 2 Sample |  |  |  |
| t0 | 5.0 | 0.4 | N.D.[d] |
| t7 | 7.3 | 0.4 | N.D. |
| t7A | 3.9 | N.D. | N.D. |
| Pass 3 Sample |  |  |  |
| t0 | 5.4 | 0.4 | N.D. |
| t7 | 7.4 | N.D. | N.D. |
| t7A | 3.8 | N.D. | N.D. |
| Pass 4 Sample |  |  |  |
| t0 | 5.2 | N.D. | N.D. |
| t7 | 7.1 | N.D. | N.D. |
| t7A | 3.9 | N.D. | N.D. |

[a]This sample was harvested at zero time and represents the residual input virus. The titer is expressed as $\log_{10}$pfu per ml.
[b]This sample was harvested at 7 days post-infection.
[c]This sample was inoculated in the presence of 40 μg/ml of Cytosine arabinoside and harvested at 7 days post infection.
[d]Not detectable

TABLE 2

Sequential Passage of ALVAC-RG in Avian and non-Avian Cells

|  | CEF | Vero | MRC-5 |
|---|---|---|---|
| Pass 1 Sample |  |  |  |
| t0[a] | 3.0 | 2.9 | 2.9 |
| t7[b] | 7.1 | 1.0 | 1.4 |
| t7A[c] | 1.8 | 1.4 | 1.2 |
| Pass 2 Sample |  |  |  |
| t0 | 5.1 | 0.4 | 0.4 |
| t7 | 7.1 | N.D.[d] | N.D. |
| t7A | 3.8 | N.D. | N.D. |
| Pass 3 Sample |  |  |  |
| t0 | 5.1 | 0.4 | N.D. |
| t7 | 7.2 | N.D. | N.D. |
| t7A | 3.6 | N.D. | N.D. |
| Pass 4 Sample |  |  |  |
| t0 | 5.1 | N.D. | N.D. |
| t7 | 7.0 | N.D. | N.D. |
| t7A | 4.0 | N.D. | N.D. |

[a]This sample was harvested at zero time and represents the residual input virus. The titer is expressed as $\log_{10}$pfu per ml.
[b]This sample was harvested at 7 days post-infection.
[c]This sample was inoculated in the presence of 40 μg/ml of Cytosine arabinoside and harvested at 7 days post-infection.
[d]Not detectable.

TABLE 3

Amplification of residual virus by passage in CEF cells

|  | CEF | Vero | MRC-5 |
|---|---|---|---|
| a) ALVAC Pass |  |  |  |
| 2[a] | 7.0[b] | 6.0 | 5.2 |
| 3 | 7.5 | 4.1 | 4.9 |
| 4 | 7.5 | N.D.[c] | N.D. |
| 5 | 7.1 | N.D. | N.D. |
| b) ALVAC-RG Pass |  |  |  |
| 2[a] | 7.2 | 5.5 | 5.5 |
| 3 | 7.2 | 5.0 | 5.1 |
| 4 | 7.2 | N.D. | N.D. |
| 5 | 7.2 | N.D. | N.D. |

[a]Pass 2 represents the amplification in CEF cells of the 7 day sample from Pass 1.
[b]Titer expressed as $\log_{10}$ pfu per ml
[c]Not Detectable

TABLE 4

Schedule of inoculation of rhesus macaques with ALVAC-RG (vCP65)

| Animal | Inoculation |  |
|---|---|---|
| 176L | Primary: | $1 \times 10^8$ pfu of vCP65 orally in TANG |
|  | Secondary: | $1 \times 10^7$ pfu of vCP65 plus $1 \times 10^7$ pfu of vCP82[a] by SC route |

TABLE 4-continued

Schedule of inoculation of rhesus macaques with ALVAC-RG (vCP65)

| Animal | | Inoculation |
|---|---|---|
| 185 L | Primary: | $1 \times 10^8$ pfu of vCP65 orally in Tang |
| | Secondary: | $1 \times 10^7$ pfu of vCP65 plus $1 \times 10^7$ pfu of vCP82 by SC route |
| 177 L | Primary: | $5 \times 10^7$ pfu SC of vCP65 by SC route |
| | Secondary: | $1 \times 10^7$ pfu of vCP65 plus $1 \times 10^7$ pfu of vCP82 by SC route |
| 186L | Primary: | $5 \times 10^7$ pfu of vCP65 by SC route |
| | Secondary: | $1 \times 10^7$ pfu of vCP65 plus $1 \times 10^7$ pfu of vCP82 by SC route |
| 178L | Primary: | $1 \times 10^7$ pfu of vCP65 by SC route |
| 182L | Primary: | $1 \times 10^7$ pfu of vCP65 by IM route |
| 179L | Primary: | $1 \times 10^6$ pfu of vCP65 by SC route |
| 183L | Primary: | $1 \times 10^6$ pfu of vCP65 by IM route |
| 180L | Primary: | $1 \times 10^6$ pfu of vCP65 by SC route |
| 184L | Primary: | $1 \times 10^5$ pfu of vCP65 by IM route |
| 187L | Primary | $1 \times 10^7$ pfu of vCP65 orally |

[a]vCP82 is a canarypox virus recombinant expressing the measles virus fusion and hemagglutinin genes.

TABLE 5

Analysis of yield in avian and non-avian cells inoculated with ALVAC-RG

| Sample Time Cell Type | t0 | t72 | t72A[b] |
|---|---|---|---|
| Expt 1 | | | |
| CEF | 3.3[a] | 7.4 | 1.7 |
| Vero | 3.0 | 1.4 | 1.7 |
| MRC-5 | 3.4 | 2.0 | 1.7 |
| Expt 2 | | | |
| CEF | 2.9 | 7.5 | <1.7 |
| WISH | 3.3 | 2.2 | 2.0 |
| Detroit-532 | 2.8 | 1.7 | <1.7 |

[a]Titer expressed as $\log_{10}$ pfu per ml
[b]Culture incubated in the presence of 40 μg/ml of Cytosine arabinoside

TABLE 6

Potency of ALVAC-RG as tested in mice

| Test | Challenge Dose[a] | $PD_{50}$[b] |
|---|---|---|
| Initial seed | 43 | 4.56 |
| Primary seed | 23 | 3.34 |
| Vaccine Batch H | 23 | 4.52 |
| Vaccine Batch I | 23 | 3.33 |
| Vaccine Batch K | 15 | 3.64 |
| Vaccine Batch L | 15 | 4.03 |
| Vaccine Batch M | 15 | 3.32 |
| Vaccine Batch N | 15 | 3.39 |
| Vaccine Batch J | 23 | 3.42 |

[a]Expressed as mouse $LD_{50}$
[b]Expressed as $\log_{10}$ $TCID_{50}$

TABLE 7

Efficacy of ALVAC-RG in dogs and cats

| | Dogs | | Cats | |
|---|---|---|---|---|
| Dose | Antibody[a] | Survival[b] | Antibody | Survival |
| 6.7 | 11.9 | 5/5 | 2.9 | 3/5 |
| 7.7 | 10.1 | N.T. | 8.1 | N.T. |

[a]Antibody at day 29 post inoculation expressed as the geometric mean titer in International Units.
[b]Expressed as a ratio of survivors over animals challenged

TABLE 8

Anti-rabies serological response of Squirrel monkeys inoculated with canarypox recombinants

| Monkey # | Previous Exposure | Rabies serum-neutralizing antibody[a] | | | | | | |
|---|---|---|---|---|---|---|---|---|
| | | -196[b] | 0 | 3 | 7 | 11 | 21 | 28 |
| 22 | ALVAC[c] | NT[g] | <1.2 | <1.2 | <1.2 | 2.1 | 2.3 | 2.2 |
| 51 | ALVAC[c] | NT | <1.2 | <1.2 | 1.7 | 2.2 | 2.2 | 2.2 |
| 39 | vCP37[d] | NT | <1.2 | <1.2 | 1.7 | 2.1 | 2.2 | N.T.[g] |
| 55 | vCP37[d] | NT | <1.2 | <1.2 | 1.7 | 2.2 | 2.1 | N.T. |
| 37 | ALVAC-RG[e] | 2.2 | <1.2 | <1.2 | 3.2 | 3.5 | 3.5 | 3.2 |
| 53 | ALVAC-RG[e] | 2.2 | <1.2 | <1.2 | 3.6 | 3.6 | 3.6 | 3.4 |
| 38 | ALVAC-RG[f] | 2.7 | <1.7 | <1.7 | 3.2 | 3.8 | 3.6 | N.T. |
| 54 | ALVAC-RG[f] | 3.2 | <1.7 | <1.5 | 3.6 | 4.2 | 4.0 | 3.6 |
| 57 | None | NT | <1.2 | <1.2 | 1.7 | 2.7 | 2.7 | 2.3 |

[a]As determined by RFFI test on days indicated and expressed in International Units
[b]Day-196 represents serum from day 28 after primary vaccination
[c]Animals received 5.0 $\log_{10}$ $TCID_{50}$ of ALVAC
[d]Animals received 5.0 $\log_{10}$ $TCID_{50}$ of vCP37
[e]Animals received 5.0 $\log_{10}$ $TCID_{50}$ of ALVAC-RG
[f]Animals received 7.0 $\log_{10}$ $TCID_{50}$ of ALVAC-RG
[g]Not tested.

TABLE 9

Inoculation of rhesus macaques with ALVAC-RG[a]

| | Route of Primary Inoculation | | | | | | | | | |
|---|---|---|---|---|---|---|---|---|---|---|
| Days post- | or/Tang | | SC | SC | SC | IM | SC | IM | SC | IM | OR |
| Inoculation | 176L[b] | 185L | 177L | 186L | 178L | 182L | 179L | 183L | 180L | 184L | 187L[b] |
| −84 | − | − | − | | | | | | | | |
| −9 | − | − | − | − | − | − | | | | | |
| 3 | − | − | − | − | | | | | | | |
| 6 | − | − | ± | ± | | | | | | | |
| 11 | − | − | 16[d] | 128 | | | | | | | |
| 19 | − | − | 32 | 128 | − | − | | | | | |
| 35 | − | − | 32 | 512 | | | | | | | |
| 59 | − | − | 64 | 256 | | | | | | | |
| 75 | − | − | 64 | 128 | − | − | | | | | |
| 99[c] | − | − | 64 | 256 | − | − | − | − | − | − | |
| 2 | − | − | 32 | 256 | − | − | − | − | − | − | |
| 6 | − | − | 512 | 512 | − | − | − | − | − | − | |
| 15 | 16 | 16 | 512 | 512 | 64 | 32 | 64 | 128 | 32 | − | − |
| 29 | 16 | 32 | 256 | 256 | 64 | 64 | 32 | 128 | 32 | − | − |
| 55 | | 32 | | | | 32 | | 32 | 16 | − | |
| 57 | 16 | | 128 | 128 | 16 | | 16 | | | | − |

[a]See Table 9 for schedule of inoculations.
[b]Animals 176L and 185L received 8.0 log$_{10}$ pfu by the oral route in 5 ml Tang. Animal 187L received 7.0 log$_{10}$ pfu by oral route not in Tang.
[c]Day of re-vaccination for animals 176L, 185L, 177L and 186L by S.C. route, and primary vaccination for animals 178L, 182L, 179L, 183L, 180L, 184L and 187L.
[d]Titers expressed as reciprocal of last dilution showing inhibition of fluorescence in an RFFI test.

TABLE 10

Inoculation of chimpanzees with ALVAC-RG

| Weeks post-Inoculation | Animal 431 I.M. | Animal 457 S.C. |
|---|---|---|
| 0 | <8[a] | <8 |
| 1 | <8 | <8 |
| 2 | 8 | 32 |
| 4 | 16 | 32 |
| 8 | 16 | 32 |
| 12[b]/0 | 16 | 8 |
| 13/1 | 128 | 128 |
| 15/3 | 256 | 512 |
| 20/8 | 64 | 128 |
| 26/12 | 32 | 128 |

[a]Titer expressed as reciprocal of last dilution showing inhibition of fluorescence in an RFFI test
[b]Day of re-inoculation

EXAMPLE 9

IMMUNIZATION OF HUMANS USING CANARYPOX EXPRESSING RABIES GLYCOPROTEIN (ALVAC-RG: vCP65)

Figure 9A:
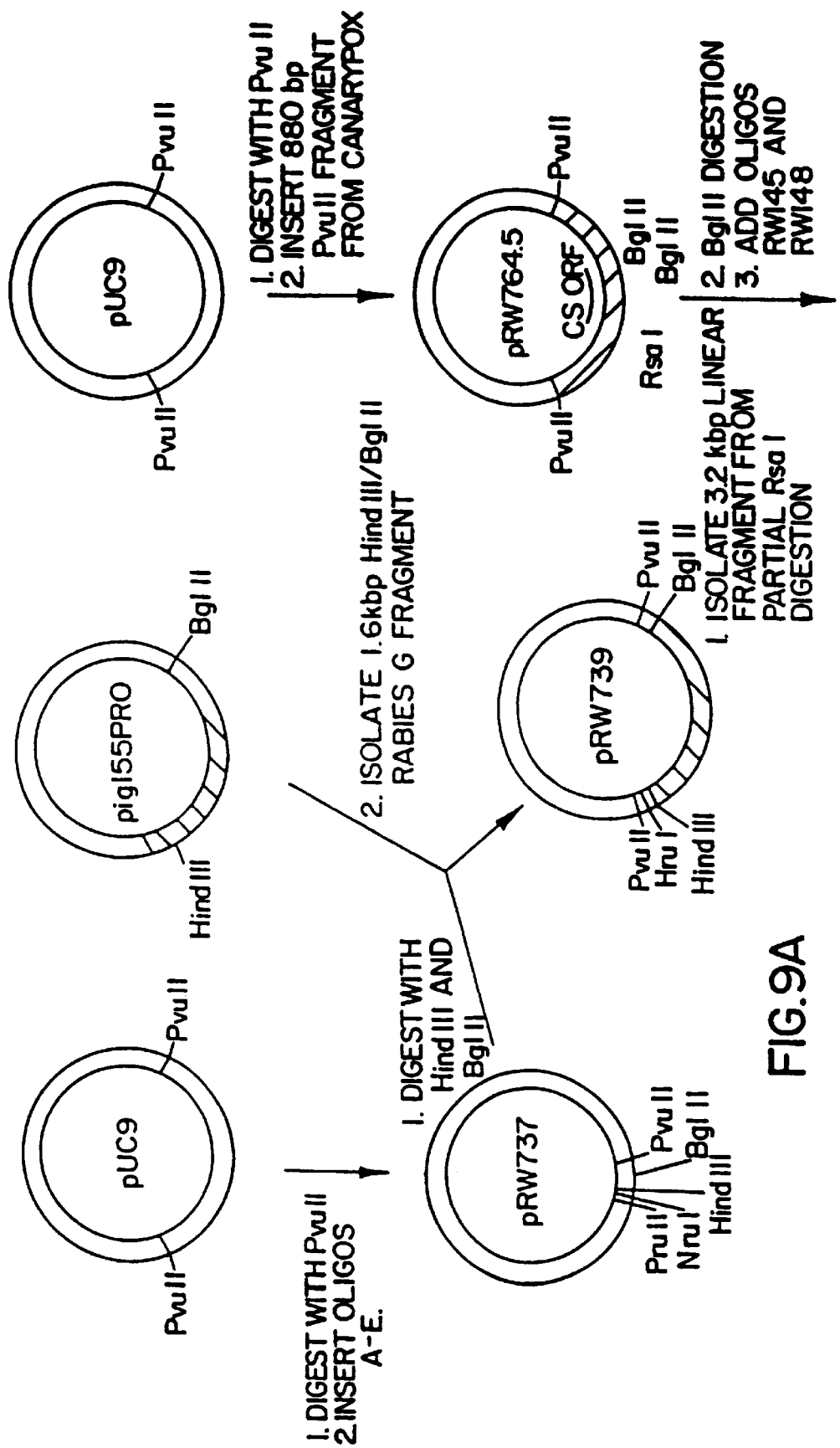
FIGS. 9A and 9B schematically show a method for the construction of recombinant canarypox virus vCP65 (ALVAC-RG)
Figure 9B:
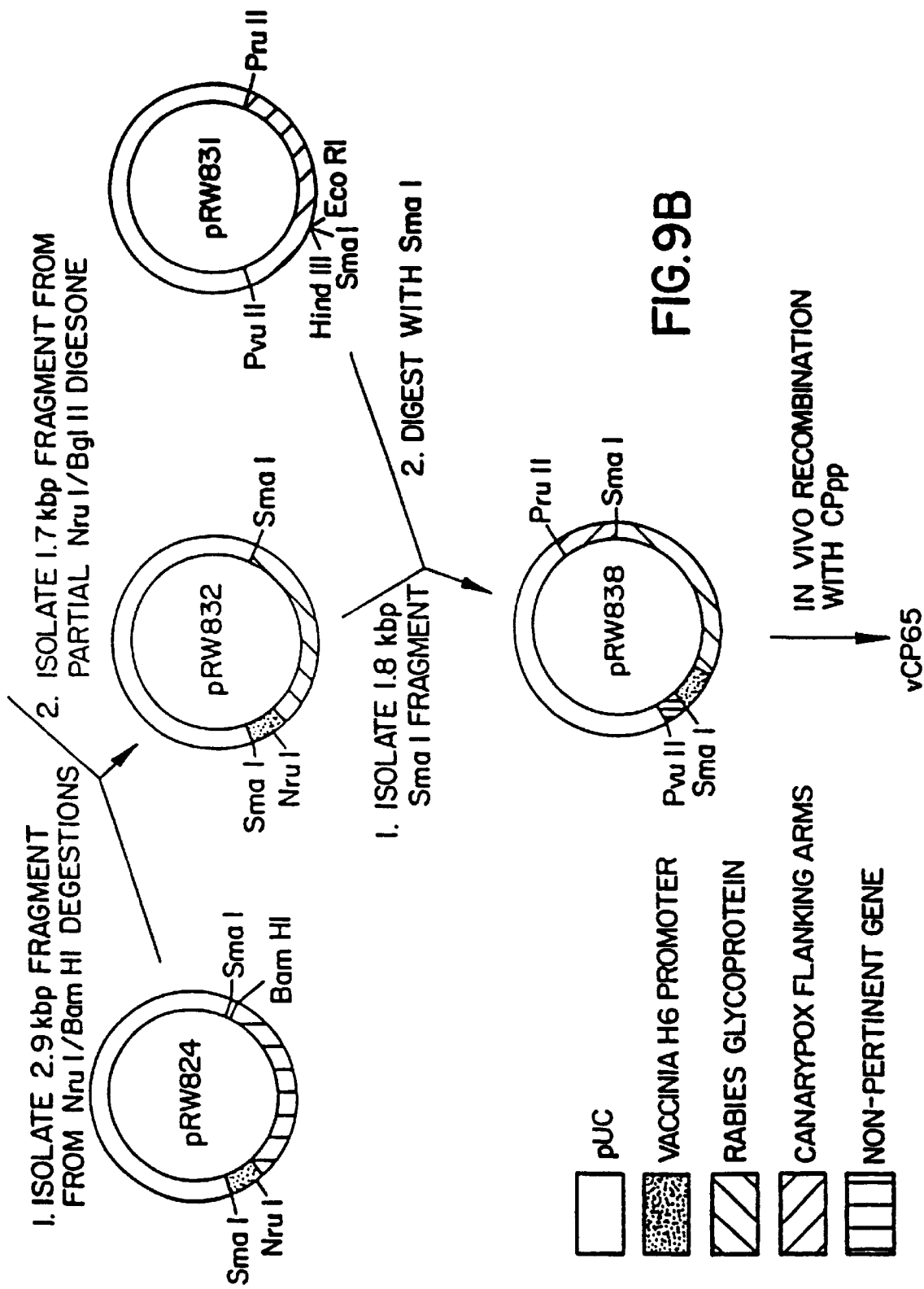
Figure 10:
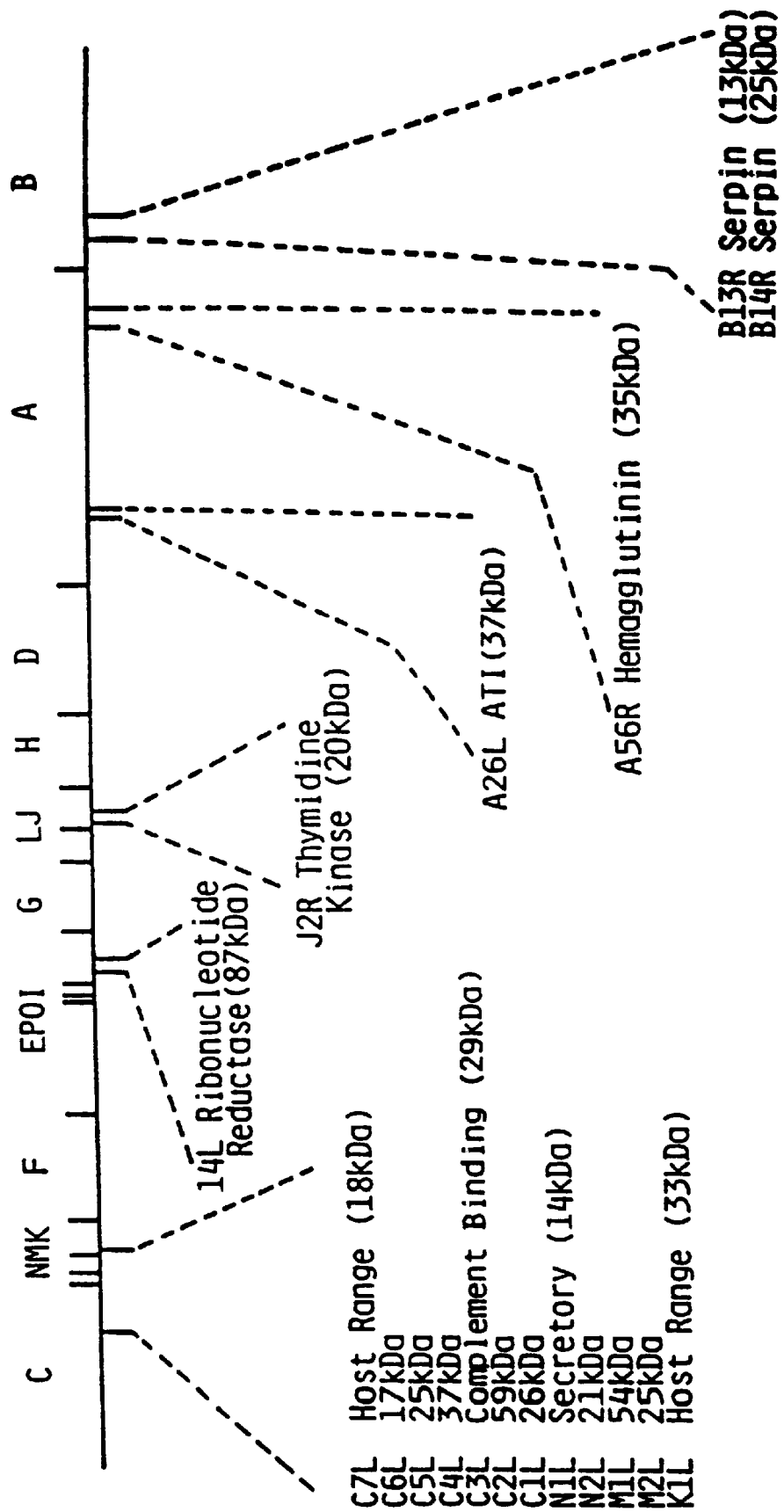
FIG. 10 shows schematically the ORFs deleted to generate NYVAC.
Figure 11B:
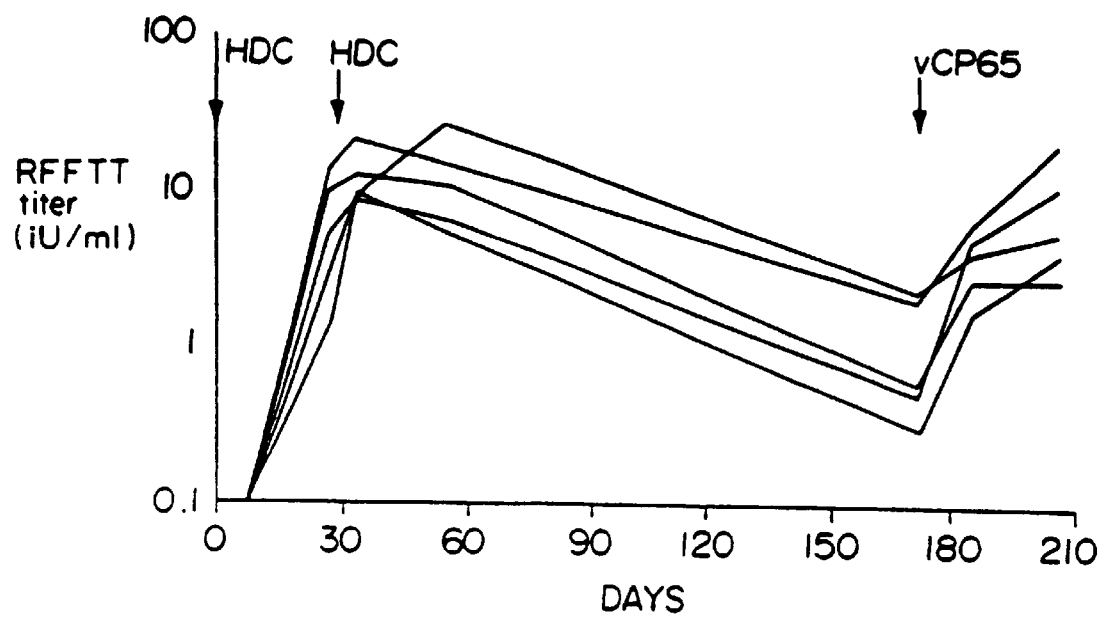
Figure 11D:
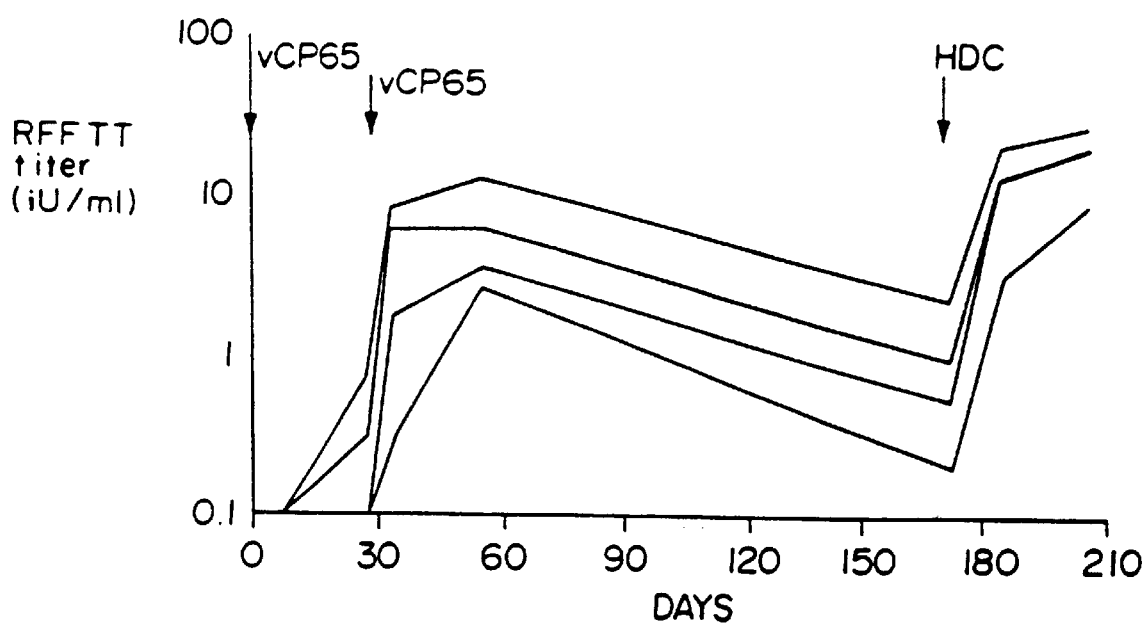

ALVAC-RG (vCP65) was generated as described in Example 9 and FIGS. 9A and 9B. For scaling-up and vaccine manufacturing ALVAC-RG (vCP65) was grown in primary CEF derived from specified pathogen free eggs. Cells were infected at a multiplicity of 0.1 and incubated at 37° C. for three days.

The vaccine virus suspension was obtained by ultrasonic disruption in serum free medium of the infected cells; cell debris were then removed by centrifugation and filtration. The resulting clarified suspension was supplemented with lyophilization stabilizer (mixture of amino-acids), dispensed in single dose vials and freeze dried. Three batches of decreasing titer were prepared by ten-fold serial dilutions of the virus suspension in a mixture of serum free medium and lyophilization stabilizer, prior to lyophilization.

Quality control tests were applied to the cell substrates, media and virus seeds and final product with emphasis on the search for adventitious agents and inocuity in laboratory rodents. No undesirable trait was found.

Preclinical data. Studies in vitro indicated that VERO or MRC-5 cells do not support the growth of ALVAC-RG (vCP65); a series of eight (VERO) and 10 (MRC) blind serial passages caused no detectable adaptation of the virus to grow in these non avian lines. Analyses of human cell lines (MRC-5, WISH, Detroit 532, HEL, HNK or EBV-transformed lymphoblastoid cells) infected or inoculated with ALVAC-RG (vCP65) showed no accumulation of virus specific DNA suggesting that in these cells the block in replication occurs prior to DNA synthesis. Significantly, however, the expression of the rabies virus glycoprotein gene in all cell lines tested indicating that the abortive step in the canarypox replication cycle occurs prior to viral DNA replication.

The safety and efficacy of ALVAC-RG (vCP65) were documented in a series of experiments in animals. A number of species including canaries, chickens, ducks, geese, laboratory rodents (suckling and adult mice), hamsters, guinea-pigs, rabbits, cats and dogs, squirrel monkeys, rhesus macaques and chimpanzees, were inoculated with doses ranging from $10^5$ to $10^8$ pfu. A variety of routes were used, most commonly subcutaneous, intramuscular and intradermal but also oral (monkeys and mice) and intracerebral (mice).

In canaries, ALVAC-RG (vCP65) caused a "take" lesion at the site of scarification with no indication of disease or death. Intradermal inoculation of rabbits resulted in a typical poxvirus inoculation reaction which did not spread and healed in seven to ten days. There was no adverse side effects due to canarypox in any of the animal tests. Immunogenicity was documented by the development of anti-rabies antibodies following inoculation of ALVAC-RG (vCP65) in rodents, dogs, cats, and primates, as measured by Rapid Fluorescent Focus Inhibition Test (RFFIT). Protection was also demonstrated by rabies virus challenge experiments in mice, dogs, and cats immunized with ALVAC-RG (vCP65).

Volunteers. Twenty-five healthy adults aged 20–45 with no previous history of rabies immunization were enrolled. Their health status was assessed by complete medical histories, physical examinations, hematological and blood chemistry analyses. Exclusion criteria included pregnancy, allergies, immune depression of any kind, chronic debilitating disease, cancer, injection of immune globins in the past three months, and seropositivity to human immunodeficiency virus (HIV) or to hepatitis B virus surface antigen.

Study design. Participants were randomly allocated to receive either standard Human Diploid Cell Rabies Vaccine (HDC) batch no E0751 (Pasteur Merieux Serums & Vaccine, Lyon, France) or the study vaccine ALVAC-RG (vCP65).

The trial was designated as a dose escalation study. Three batches of experimental ALVAC-RG (vCP65) vaccine were used sequentially in three groups of volunteers (Groups A, B and C) with two week intervals between each step. The concentration of the three batches was $10^{3.5}$, $10^{4.5}$, $10^{5.5}$ Tissue Culture Infectious Dose ($TCID_{50}$) per dose, respectively.

Each volunteer received two doses of the same vaccine subcutaneously in the deltoid region at an interval of four weeks. The nature of the injected vaccine was not known by the participants at the time of the first injection but was known by the investigator.

In order to minimize the risk of immediate hypersensitivity at the time of the second injection, the volunteers of Group B allocated to the medium dose of experimental vaccine were injected 1 h previously with the lower dose and those allocated to the higher dose (Group C) received successively the lower and the medium dose at hourly intervals.

Six months later, the recipients of the highest dosage of ALVAC-RG (vCP65) (Group C) and HDC vaccine were offered a third dose of vaccine; they were then randomized to receive either the same vaccine as previously or the alternate vaccine. As a result, four groups were formed corresponding to the following immunization scheme: 1. HDC, HDC—HDC; 2. HDC, HDC—ALVAC-RG (vCP65); 3. ALVAC-RG (vCP65), ALVAC-RG (vCP65)—HDC; 4. ALVAC-RG (vCP65), ALVAC-RG (vCP65), ALVAC-RG (vCP65).

Monitoring of Side Effects. All subjects were monitored for 1 h after injection and re-examined every day for the next five days. They were asked to record local and systemic reactions for the next three weeks and were questioned by telephone two times a week.

Laboratory Investigators. Blood specimens were obtained before enrollment and two, four and six days after each injection. Analysis included complete blood cell count, liver enzymes and creatine kinase assays.

Antibody assays. Antibody assays were performed seven days prior to the first injection and at days 7, 28, 35, 56, 173, 187 and 208 of the study.

The levels of neutralizing antibodies to rabies were determined using the Rapid Fluorescent Focus Inhibition test (RFFIT) (Smith et al., 1973). Canarypox antibodies were measured by direct ELISA. The antigen, a suspension of purified canarypox virus disrupted with 0.1% Triton X100, was coated in microplates. Fixed dilutions of the sera were reacted for two hours at room temperature and reacting antibodies were revealed with a peroxidase labelled anti-human IgG goat serum. The results are expressed as the optical density read at 490nm.

Analysis. Twenty-five subjects were enrolled and completed the study. There were 10 males and 15 females and the mean age was 31.9 (21 to 48). All but three subjects had evidence of previous smallpox vaccination; the three remaining subjects had no typical scar and vaccination history. Three subjects received each of the lower doses of experimental vaccine ($10^{3.5}$ and $10^{4.5}$ $TCID_{50}$), nine subjects received $10^{5.5}$ $TCID_{50}$ and ten received the HDC vaccine.

Safety (Table 11). During the primary series of immunization, fever greater than 37.7° C. was noted within 24 hours after injection in one HDC recipient (37.8° C.) and in one vCP65 $10^{5.5}$ $TCID_{50}$ recipient (38° C.). No other systemic reaction attributable to vaccination was observed in any participant.

Local reactions were noted in 9/10 recipients of HDC vaccine injected subcutaneously and in 0/3, 1/3 and 9/9 recipients of vCP65 $10^{3.5}$, $10^{4.5}$, $10^{5.5}$ $TCID_{50}$, respectively.

Tenderness was the most common symptoms and was always mild. Other local symptoms included redness and induration which were also mild and transient. All symptoms usually subsided within 24 hours and never lasted more than 72 hours.

There was no significant change in blood cell counts, liver enzymes or creatine kinase values.

Immune Responses: Neutralizing Antibodies to Rabies (Table 12). Twenty eight days after the first injection all the HDC recipients had protective titers ($\geq 0.5$ IU/ml). By contrast none in groups A and B ($10^{3.5}$ and $10^{4.5}$ $TCID_{50}$) and only 2/9 in group C ($10^{5.5}$ $TCID_{50}$) ALVAC-RG (vCP65) recipients reached this protective titer.

At day 56 (i.e. 28 days after the second injection) protective titers were achieved in 0/3 of Group A, 2/3 of Group B and 9/9 of Group C recipients of ALVAC-RG (vCP65) vaccine and persisted in all 10 HDC recipients.

At day 56 the geometric mean titers were 0.05, 0.47, 4.4 and 11.5 IU/ml in groups A, B, C and HDC respectively.

At day 180, the rabies antibody titers had substantially decreased in all subjects but remained above the minimum protective titer of 0.5 IU/ml in 5/10 HCD recipients and in 5/9 ALVAC-RG (vCP65) recipients; the geometric mean titers were 0.51 and 0.45 IU/ml in groups HCD and C, respectively.

Antibodies to the Canarypox virus (Table 13). The pre-immune titers observed varied widely with titers varying from 0.22 to 1.23 O.D. units despite the absence of any previous contact with canary birds in those subjects with the highest titers. When defined as a greater than two-fold increase between preimmunization and post second injection titers, a seroconversion was obtained in 1/3 subjects in group B and in 9/9 subjects in group C whereas no subject seroconverted in groups A or HDC.

Booster Injection. The vaccine was similarly well tolerated six months later, at the time of the booster injection: fever was noted in 2/9 HDC booster recipients and in 1/10 ALVAC-RG (vCP65) booster recipients. Local reactions were present in 5/9 recipients of HDC booster and in 6/10 recipients of the ALVAC-RG (vCP65) booster.

Observations. FIGS. 11A–11D show graphs of rabies neutralizing antibody titers (Rapid Fluorescent Focus Inhibition Test or RFFIT, IU/ml): Booster effect of HDC and vCP65 ($10^{5.5}$ $TCID_{50}$) in volunteers previously immunized with either the same or the alternate vaccine. Vaccines were given at days 0, 28 and 180. Antibody titers were measured at days 0, 7, 28, 35, 56, 173, and 187 and 208.

As shown in FIGS. 11A to 11D, the booster dose given resulted in a further increase in rabies antibody titers in every subject whatever the immunization scheme. However, the ALVAC-RG (vCP65) booster globally elicited lower immune responses than the HDC booster and the ALVAC-RG (vCP65), ALVAC-RG (vCP65)—ALVAC-RG (vCP65) group had significantly lower titers than the three other groups. Similarly, the ALVAC-RG (vCP65) booster injection resulted in an increase in canarypox antibody titers in 3/5 subjects who had previously received the HDC vaccine and in all five subjects previously immunized with ALVAC-RG (vCP65).

In general, none of the local side effects from administration of vCP65 was indicative of a local replication of the virus. In particular, lesions of the skin such as those observed after injection of vaccine were absent. In spite of the apparent absence of replication of the virus, the injection resulted in the volunteers generating significant amounts of antibodies to both the canarypox vector and to the expressed rabies glycoprotein.

Rabies neutralizing antibodies were assayed with the Rapid Fluorescent Focus Inhibition Test (RFFIT) which is known to correlate well with the sero neutralization test in mice. Of 9 recipients of $10^{5.5}$ TCID$_{50}$, five had low level responses after the first dose. Protective titers of rabies antibodies were obtained after the second injection in all recipients of the highest dose tested and even in 2 of the 3 recipients of the medium dose. In this study, both vaccines were given subcutaneously as usually recommended for live vaccines, but not for the inactivated HDC vaccine. This route of injection was selected as it best allowed a careful examination of the injection site, but this could explain the late appearance of antibodies in HDC recipients: indeed, none of the HDC recipients had an antibody increase at day 7, whereas, in most studies where HDC vaccine is give intramuscularly a significant proportion of subjects do (Klietmann et al., Int'l Green Cross—Geneva, 1981; Kuwert et al., Int'l Green Cross—Geneva, 1981). However, this invention is not necessarily limited to the subcutaneous route of administration.

The GMT (geometric mean titers) of rabies neutralizing antibodies was lower with the investigational vaccine than with the HDC control vaccine, but still well above the minimum titer required for protection. The clear dose effect response obtained with the three dosages used in this study suggest that a higher dosage might induce a stronger response. Certainly from this disclosure the skilled artisan can select an appropriate dosage for a given patient.

The ability to boost the antibody response is another important result of this Example; indeed, an increase in rabies antibody titers was obtained in every subject after the 6 month dose whatever the immunization scheme, showing that preexisting immunity elicited by either the canarypox vector or the rabies glycoprotein had no blocking effect on the booster with the recombinant vaccine candidate or the conventional HDC rabies vaccine. This contrasts findings of others with vaccinia recombinants in humans that immune response may be blocked by pre-existing immunity (Cooney et al., 1991; Etinger et al.).

Thus, this Example clearly demonstrates that a non-replicating poxvirus can serve as an immunizing vector in humans, with all of the advantages that replicating agents confer on the immune response, but without the safety problem created by a fully permissive virus. And, from this disclosure such as this Example and other Examples suitable dosages and modes or routes for administration or immunization of recombinants containing either rabies or other coding, or expression products thereof, are within the ambit of the skilled artisan as well modes for in vitro expression.

TABLE 11

Reactions in the 5 days following vaccination

| vCP65 dosage (TCID50) | $10^{3.5}$ | | $10^{4.5}$ | | $10^{5.5}$ | | HDC control | |
|---|---|---|---|---|---|---|---|---|
| Injection | 1st | 2nd | 1st | 2nd | 1st | 2nd | 1st | 2nd |
| No. vaccinees | 3 | 3 | 3 | 3 | 9 | 9 | 10 | 10 |
| temp >37.7° C. | 0 | 0 | 0 | 0 | 0 | 1 | 1 | 0 |
| soreness | 0 | 0 | 1 | 1 | 6 | 8 | 8 | 6 |
| redness | 0 | 0 | 0 | 0 | 0 | 4 | 5 | 4 |
| induration | 0 | 0 | 0 | 0 | 0 | 4 | 5 | 4 |

TABLE 12

Rabies neutralizing antibodies (REFIT; IU/ml)
Individual titers and geometric mean titers (GMT)

| No. | TCID50/ dose | Days | | | | |
|---|---|---|---|---|---|---|
| | | 0 | 7 | 28 | 35 | 56 |
| 1 | $10^{3.5}$ | <0.1 | <0.1 | <0.1 | <0.1 | 0.2 |
| 3 | $10^{3.5}$ | <0.1 | <0.1 | <0.1 | <0.1 | <0.1 |
| 4 | $10^{3.5}$ | <0.1 | <0.1 | <0.1 | <0.1 | <0.1 |
| G.M.T. | | <0.1 | <0.1 | <0.1 | <0.1 | <0.1 |
| 6 | $10^{4.5}$ | <0.1 | <0.1 | <0.1 | <0.1 | <0.1 |
| 7 | $10^{4.5}$ | <0.1 | <0.1 | <0.1 | 2.4 | 1.9 |
| 10 | $10^{4.5}$ | <0.1 | <0.1 | <0.1 | 1.6 | 1.1 |
| G.M.T. | | <0.1 | <0.1 | 0.1 | 0.58 | 0.47 |
| 11 | $10^{5.5}$ | <0.1 | <0.1 | 1.0 | 3.2 | 4.3 |
| 13 | $10^{5.5}$ | <0.1 | <0.1 | 0.3 | 6.0 | 8.8 |
| 14 | $10^{5.5}$ | <0.1 | <0.1 | 0.2 | 2.1 | 9.4 |
| 17 | $10^{5.5}$ | <0.1 | <0.1 | <0.1 | 1.2 | 2.5 |
| 18 | $10^{5.5}$ | <0.1 | <0.1 | 0.7 | 8.3 | 12.5 |
| 20 | $10^{5.5}$ | <0.1 | <0.1 | <0.1 | 0.3 | 3.7 |
| 21 | $10^{5.5}$ | <0.1 | <0.1 | 0.2 | 2.6 | 3.9 |
| 23 | $10^{5.5}$ | <0.1 | <0.1 | <0.1 | 1.7 | 4.2 |
| 25 | $10^{5.5}$ | <0.1 | <0.1 | <0.1 | 0.6 | 0.9 |
| G.M.T. | | <0.1 | <0.1 | 0.16 | 1.9 | 4.4* |
| 2 | HDC | <0.1 | <0.1 | 0.8 | 7.1 | 7.2 |
| 5 | HDC | <0.1 | <0.1 | 9.9 | 12.8 | 18.7 |
| 8 | HDC | <0.1 | <0.1 | 12.7 | 21.1 | 16.5 |
| 9 | HDC | <0.1 | <0.1 | 6.0 | 9.9 | 14.3 |
| 12 | HDC | <0.1 | <0.1 | 5.0 | 9.2 | 25.3 |
| 15 | HDC | <0.1 | <0.1 | 2.2 | 5.2 | 8.6 |
| 16 | HDC | <0.1 | <0.1 | 2.7 | 7.7 | 20.7 |
| 19 | HDC | <0.1 | <0.1 | 2.6 | 9.9 | 9.1 |
| 22 | HDC | <0.1 | <0.1 | 1.4 | 8.6 | 6.6 |
| 24 | HDC | <0.1 | <0.1 | 0.8 | 5.8 | 4.7 |
| G.M.T. | | <0.1 | <0.1 | 2.96 | 9.0 | 11.5* |

*p = 0.007 student t test

TABLE 13

Canarypox antibodies: ELISA Geometric Mean Titers*

| vCP65 dosage | Days | | | | |
|---|---|---|---|---|---|
| TCID50/dose | 0 | 7 | 28 | 35 | 56 |
| $10^{3.5}$ | 0.69 | ND | 0.76 | ND | 0.68 |
| $10^{4.5}$ | 0.49 | 0.45 | 0.56 | 0.63 | 0.87 |
| $10^{5.5}$ | 0.38 | 0.38 | 0.77 | 1.42 | 1.63 |
| HDC control | 0.45 | 0.39 | 0.40 | 0.35 | 0.39 |

*optical density at 1/25 dilution

EXAMPLE 10

COMPARISON OF THE LD$_{50}$ OF ALVAC AND NYVAC WITH VARIOUS VACCINIA VIRUS STRAINS

Mice. Male outbred Swiss Webster mice were purchased from Taconic Farms (Germantown, N.Y.) and maintained on mouse chow and water ad libitum until use at 3 weeks of age ("normal" mice). Newborn outbred Swiss Webster mice were of both sexes and were obtained following timed pregnancies performed by Taconic Farms. All newborn mice used were delivered within a two day period.

Viruses. ALVAC was derived by plaque purification of a canarypox virus population and was prepared in primary chick embryo fibroblast cells (CEF). Following purification by centrifugation over sucrose density gradients, ALVAC was enumerated for plaque forming units in CEF cells. The WR(L) variant of vaccinia virus was derived by selection of large plaque phenotypes of WR (Panicali et al., 1981). The Wyeth New York State Board of Health vaccine strain of vaccinia virus was obtained from Pharmaceuticals Calf Lymph Type vaccine Dryvax, control number 302001B. Copenhagen strain vaccinia virus VC-2 was obtained from Institut Merieux, France. Vaccinia virus strain NYVAC was derived from Copenhagen VC-2. All vaccinia virus strains except the Wyeth strain were cultivated in Vero African green monkey kidney cells, purified by sucrose gradient density centrifugation and enumerated for plaque forming units on Vero cells. The Wyeth strain was grown in CEF cells and enumerated for plaque forming units in CEF cells.

Inoculations. Groups of 10 normal mice were inoculated intracranially (ic) with 0.05 ml of one of several dilutions of virus prepared by 10-fold serially diluting the stock preparations in sterile phosphate-buffered saline. In some instances, undiluted stock virus preparation was used for inoculation.

Groups of 10 newborn mice, 1 to 2 days old, were inoculated ic similarly to the normal mice except that an injection volume of 0.03 ml was used.

All mice were observed daily for mortality for a period of 14 days (newborn mice) or 21 days (normal mice) after inoculation. Mice found dead the morning following inoculation were excluded due to potential death by trauma.

The lethal dose required to produce mortality for 50% of the experimental population (LD$_{50}$) was determined by the proportional method of Reed and Muench.

Comparison of the LD$_{50}$ of ALVAC and NYVAC with Various Vaccinia Virus Strains for Normal. Young Outbred Mice by the ic Route. In young, normal mice, the virulence of NYVAC and ALVAC were several orders of magnitude lower than the other vaccinia virus strains tested (Table 14). NYVAC and ALVAC were found to be over 3,000 times less virulent in normal mice than the Wyeth strain; over 12,500 times less virulent than the parental VC-2 strain; and over 63,000,000 times less virulent than the WR(L) variant. These results would suggest that NYVAC is highly attenuated compared to other vaccinia strains, and that ALVAC is generally nonvirulent for young mice when administered intracranially, although both may cause mortality in mice at extremely high doses (3.85×10$^8$ PFUs, ALVAC and 3×10$^8$ PFUs, NYVAC) by an undetermined mechanism by this route of inoculation.

Comparison of the LD$_{50}$ of ALVAC and NYVAC with Various Vaccinia Virus Strains for Newborn Outbred Mice by the ic Route. The relative virulence of 5 poxvirus strains for normal, newborn mice was tested by titration in an intracranial (ic) challenge model system (Table 15). With mortality as the endpoint, LD$_{50}$ values indicated that ALVAC is over 100,000 times less virulent than the Wyeth vaccine strain of vaccinia virus; over 200,000 times less virulent than the Copenhagen VC-2 strain of vaccinia virus; and over 25,000,000 times less virulent than the WR-L variant of vaccinia virus. Nonetheless, at the highest dose tested, 6.3×10$^7$ PFUS, 100% mortality resulted. Mortality rates of 33.3% were observed at 6.3×10$^6$ PFUs. The cause of death, while not actually determined, was not likely of toxicological or traumatic nature since the mean survival time (MST) of mice of the highest dosage group (approximately 6.3 LD$_{50}$) was 6.7±1.5 days. When compared to WR(L) at a challenge dose of 5 LD$_{50}$, wherein MST is 4.8±0.6 days, the MST of ALVAC challenged mice was significantly longer (P=0.001).

Relative to NYVAC, Wyeth was found to be over 15,000 times more virulent; VC-2, greater than 35,000 times more virulent; and WR(L), over 3,000,000 times more virulent. Similar to ALVAC, the two highest doses of NYVAC, 6×10$^8$ and 6×10$^7$ PFUs, caused 100% mortality. However, the MST of mice challenged with the highest dose, corresponding to 380 LD$_{50}$, was only 2 days (9 deaths on day 2 and 1 on day 4). In contrast, all mice challenged with the highest dose of WR-L, equivalent to 500 LD$_{50}$, survived to day 4.

TABLE 14

Calculated 50% Lethal Dose for mice by various vaccinia virus strains and for canarypox virus (ALVAC) by the ic route.

| POXVIRUS STRAIN | CALCULATED LD$_{50}$ (PFUs) |
|---|---|
| WR (L) | 2.5 |
| VC-2 | 1.26 × 10$^4$ |
| WYETH | 5.00 × 10$^4$ |
| NYVAC | 1.58 × 10$^8$ |
| ALVAC | 1.58 × 10$^8$ |

TABLE 15

Calculated 50% Lethal Dose for newborn mice by various vaccinia virus strains for canarypox virus (ALVAC) by the ic route.

| POXVIRUS STRAIN | CALCULATED LD$_{50}$ (PFUs) |
|---|---|
| WR (L) | 0.4 |
| VC-2 | 0.1 |
| WYETH | 1.6 |
| NYVAC | 1.58 × 10$^6$ |
| ALVAC | 1.00 × 10$^7$ |

EXAMPLE 11

EVALUATION OF NYVAC (vP866) AND NYVAC-RG (vP879)

Immunoprecipitations. Preformed monolayers of avian or non-avian cells were inoculated with 10 pfu per cell of parental NYVAC (vP866) or NYVAC-RG (vP879) virus. The inoculation was performed in EMEM free of methionine and supplemented with 2% dialyzed fetal bovine serum. After a one hour incubation, the inoculum was removed and the medium replaced with EMEM (methionine free) containing 20 µCi/ml of $^{35}$S-methionine. After an overnight incubation of approximately 16 hours, cells were lysed by the addition of Buffer A (1% Nonidet P-40, 10 mM Tris pH7.4, 150 mM NaCl, 1 mM EDTA, 0.01% sodium azide, 500 units per ml of aprotinin, and 0.02% phenyl methyl sulfonyl fluoride). Immunoprecipitation was performed using a rabies glycoprotein specific monoclonal antibody designated 24-3F10 supplied by Dr. C. Trinarchi, Griffith Laboratories, New York State Department of Health, Albany, N.Y., and a rat anti-mouse conjugate obtained from Boehringer Mannheim Corporation (Cat. #605-500). Protein A Sepharose CL-48 obtained from Pharmacia LKB Biotechnology Inc., Piscataway, N.J., was used as a support matrix. Immunoprecipitates were fractionated on 10% polyacrylamide gels according to the method of Dreyfuss et. al. (1984). Gels were fixed, treated for fluorography with 1M Na-salicylate for one hour, and exposed to Kodak XAR-2 film to visualize the immunoprecipitated protein species.

Sources of Animals. New Zealand White rabbits were obtained from Hare-Marland (Hewitt, N.J.). Three week old male Swiss Webster outbred mice, timed pregnant female Swiss Webster outbred mice, and four week old Swiss Webster nude ($nu^+nu^+$) mice were obtained from Taconic Farms, Inc. (Germantown, N.Y.). All animals were maintained according to NIH guidelines. All animal protocols were approved by the institutional IACUC. When deemed necessary, mice which were obviously terminally ill were euthanized.

Evaluation of Lesions in Rabbits. Each of two rabbits was inoculated intradermally at multiple sites with 0.1 ml of PBS containing $10^4$, $10^5$, $10^6$, $10^7$, or $10^8$ pfu of each test virus or with PBS alone. The rabbits were observed daily from day 4 until lesion resolution. Indurations and ulcerations were measured and recorded.

Virus Recovery from Inoculation Sites. A single rabbit was inoculated intradermally at multiple sites of 0/1 ml of PBS containing $10^6$, $10^7$, or $10^8$ pfu of each test virus or with PBS alone. After 11 days, the rabbit was euthanized and skin biopsy specimens taken from each of the inoculation sites were aseptically prepared by mechanical disruption and indirect sonication for virus recovery. Infectious virus was assayed by plaque titration on CEF monolayers.

Virulence in Mice. Groups of ten mice, or five in the nude mice experiment, were inoculated ip with one of several dilutions of virus in 0.5 ml of sterile PBS. Reference is also made to Example 11.

Cyclophosphamide (CY) Treatment. Mice were injected by the ip route with 4 mg (0.02 ml) of CY (SIGMA) on day −2, followed by virus injection on day 0. On the following days post infection, mice were injected ip with CY: 4 mg on day 1; 2 mg on days 4, 7 and 11; 3 mg on days 14, 18, 21, 25 and 28. Immunosuppression was indirectly monitored by enumerating white blood cells with a Coulter Counter on day 11. The average white blood cell count was 13,500 cells per $\mu l$ for untreated mice (n=4) and 4,220 cells per $\mu l$ for CY-treated control mice (n=5).

Calculation of $LD_{50}$. The lethal dose required to produce 50% mortality ($LD_{50}$) was determined by the proportional method of Reed and Muench (Reed and Muench 1938).

Potency Testing of NYVAC-RG in Mice. Four to six week old mice were inoculated in the footpad with 50 to 100 $\mu l$ of a range of dilutions (2.0–8.0 $\log_{10}$ tissue culture infective dose 50% ($TCID_{50}$)) of either VV-RG (Kieny et al., 1984), ALVAC-RG (Taylor et al., 1991b), or the NYVAC-RG. Each group consisted of eight mice. At 14 days post-vaccination, the mice were challenged by intracranial inoculation with 15 $LD_{50}$ of the rabies virus CVS strain (0.03 ml). On day 28, surviving mice were counted and protective does 50% ($PD_{50}$) calculated.

Derivation of NYVAC (vP866). The NYVAC strain of vaccinia virus was generated from VC-2, a plaque cloned isolate of the COPENHAGEN vaccine strain. To generate NYVAC from VC-2, eighteen vaccinia ORFs, including a number of viral functions associated with virulence, were precisely deleted in a series of sequential manipulations as described earlier in this disclosure. These deletions were constructed in a manner designed to prevent the appearance of novel unwanted open reading frames. FIG. 10 schematically depicts the ORFs deleted to generate NYVAC. At the top of FIG. 10 is depicted the HindIII restriction map of the vaccinia virus genome (VC-2 plaque isolate, COPENHAGEN strain). Expanded are the six regions of VC-2 that were sequentially deleted in the generation of NYVAC. The deletions were described earlier in this disclosure (Examples 1 through 6). Below such deletion locus is listed the ORFs which were deleted from that locus, along with the functions or homologies and molecular weight of their gene products.

Replication Studies of NYVAC and ALVAC on Human Tissue Cell Lines. In order to determine the level of replication of NYVAC strain of vaccinia virus (vP866) in cells of human origin, six cell lines were inoculated at an input multiplicity of 0.1 pfu per cell under liquid culture and incubated for 72 hours. The COPENHAGEN parental clone (VC-2) was inoculated in parallel. Primary chick embryo fibroblast (CEF) cells (obtained from 10–11 day old embryonated eggs of SPF origin, Spafas, Inc., Storrs, Conn.) were included to represent a permissive cell substrate for all viruses. Cultures were analyzed on the basis of two criteria: the occurrence of productive viral replication and expression of an extrinsic antigen.

The replication potential of NYVAC in a number of human derived cells are shown in Table 16. Both VC-2 and NYVAC are capable of productive replication in CEF cells, although NYVAC with slightly reduced yields. VC-2 is also capable of productive replication in the six human derived cell lines tested with comparable yields except in the EBV transformed lymphoblastoid cell line JT-1 (human lymphoblastoid cell line transformed with Epstein-Barr virus, see Rickinson et al., 1984). In contrast, NYVAC is highly attenuated in its ability to productively replicate in any of the human derived cell lines tested. Small increases of infectious virus above residual virus levels were obtained from NYVAC-infected MRC-5 (ATCC #CCL171, human embryonic lung origin), DETROIT 532 (ATCC #CCL54, human foreskin, Downs Syndrome), HEL 299 (ATCC #CCL137, human embryonic lung cells) and HNK (human neonatal kidney cells, Whittiker Bioproducts, Inc. Walkersville, Md., Cat #70-151) cells. Replication on these cell lines was significantly reduced when compared to virus yields obtained from NYVAC-infected CEF cells or with parental VC-2 (Table 16). It should be noted that the yields at 24 hours in CEF cells for both NYVAC and VC-2 is equivalent to the 72-hour yield. Allowing the human cell line cultures to incubate an additional 48 hours (another two viral growth cycles) may, therefore, have amplified the relative virus yield obtained.

Consistent with the low levels of virus yields obtained in the human-derived cell lines, MRC-5 and DETROIT 532, detectable but reduced levels of NYVAC-specific DNA accumulation were noted. The level of DNA accumulation in the MRC-5 and DETROIT 532 NYVAC-infected cell lines relative to that observed in NYVAC-infected CEF cells paralleled the relative virus yields. NYVAC-specific viral DNA accumulation was not observed in any of the other human-derived cells.

An equivalent experiment was also performed using the avipox virus, ALVAC. The results of virus replication are also shown in Table 16. No progeny virus was detectable in any of the human cell lines consistent with the host range restriction of canarypox virus to avian species. Also consistent with a lack of productive replication of ALVAC in these human-derived cells is the observation that no ALVAC-specific DNA accumulation was detectable in any of the human-derived cell lines.

Expression of Rabies Glycoprotein by NYVAC-RG (vP879) in Human Cells. In order to determine whether efficient expression of a foreign gene could be obtained in the absence of significant levels of productive viral replication, the same cell lines were inoculated with the NYVAC recombinant expressing the rabies virus glycoprotein (vP879, Example 7) in the presence of $^{35}$S-methionine. Immunoprecipitation of the rabies glycoprotein was performed from the radiolabelled culture lysate using a monoclonal antibody specific for the rabies glycoprotein. Immunoprecipitation of a 67 kDa protein was detected consistent with a fully glycosylated form of the rabies glycoprotein. No serologically crossreactive product was detected in uninfected or parental NYVAC infected cell lysates. Equivalent results were obtained with all other human cells analyzed.

Inoculations on the Rabbit Skin. The induction and nature of skin lesions on rabbits following intradermal (id) inoculations has been previously used as a measure of pathogenicity of vaccinia virus strains (Buller et al., 1988; Child et al., 1990; Fenner, 1958, Flexner et al., 1987; Ghendon and Chernos 1964). Therefore, the nature of lesions associated with id inoculations with the vaccinia strains WR (ATCC #VR119 plaque purified on CV-1 cells, ATCC #CCL70, and a plaque isolate designated L variant, ATCC #VR2035 selected, as described in Panicali et al., 1981)), WYETH (ATCC #VR325 marketed as DRYVAC by Wyeth Laboratories, Marietta, Pa.), COPENHAGEN (VC-2), and NYVAC was evaluated by inoculation of two rabbits (A069 and A128). The two rabbits displayed different overall sensitivities to the viruses, with rabbit A128 displaying less severe reactions than rabbit A069. In rabbit A128, lesions were relatively small and resolved by 27 days post-inoculation. On rabbit A069, lesions were intense, especially for the WR inoculation sites, and resolved only after 49 days. Intensity of the lesions was also dependent on the location of the inoculation sites relative to the lymph drainage network. In particular, all sites located above the backspine displayed more intense lesions and required longer times to resolve the lesions located on the flanks. All lesions were measured daily from day 4 to the disappearance of the last lesion, and the means of maximum lesion size and days to resolution were calculated (Table 17). No local reactions were observed from sites injected with the control PBS. Ulcerative lesions were observed at sites injected with WR, VC-2 and WYETH vaccinia virus strains. Significantly, no induration or ulcerative lesions were observed at sites of inoculation with NYVAC.

Persistence of Infectious Virus at the Site of Inoculation. To assess the relative persistence of these viruses at the site of inoculation, a rabbit was inoculated intradermally at multiple sites with 0.1 ml PBS containing $10^6$, $10^7$ or $10^8$ pfu of VC-2, WR, WYETH or NYVAC. For each virus, the $10^7$ pfu dose was located above the backspine, flanked by the $10^6$ and $10^8$ doses. Sites of inoculation were observed daily for 11 days. WR elicited the most intense response, followed by VC-2 and WYETH (Table 18). Ulceration was first observed at day 9 for WR and WYETH and day 10 for VC-2. Sites inoculated with NYVAC or control PBS displayed no induration or ulceration. At day 11 after inoculation, skin samples from the sites of inoculation were excised, mechanically disrupted, and virus was titrated on CEF cells.

The results are shown in Table 18. In no case was more virus recovered at this timepoint than was administered. Recovery of vaccinia strain, WR, was approximately $10^6$ pfu of virus at each site irrespective of amount of virus administered. Recovery of vaccinia strains WYETH and VC-2 was $10^3$ to $10^4$ pfu regardless of amount administered. No infectious virus was recovered from sites inoculated with NYVAC.

Inoculation of Genetically or Chemically Immune Deficient Mice. Intraperitoneal inoculation of high doses of NYVAC ($5\times10^8$ pfu) or ALVAC ($10^9$ pfu) into nude mice caused no deaths, no lesions, and no apparent disease through the 100 day observation period. In contrast, mice inoculated with WR ($10^3$ to $10^4$ pfu), WYETH ($5\times10^7$ or $5\times10^8$ pfu) or VC-2 ($10^4$ to $10^9$ pfu) displayed disseminated lesions typical of poxviruses first on the toes, then on the tail, followed by severe orchitis in some animals. In mice infected with WR or WYETH, the appearance of disseminated lesions generally led to eventual death, whereas most mice infected with VC-2 eventually recovered. Calculated $LD_{50}$ values are given in Table 19.

In particular, mice inoculated with VC-2 began to display lesions on their toes (red papules) and 1 to 2 days later on the tail. These lesions occurred between 11 and 13 days post-inoculation (pi) in mice given the highest doses ($10^9$, $10^8$, $10^7$ and $10^6$ pfu), on day 16 pi in mice given $10^5$ pfu and on day 21 pi in mice given $10^4$ pfu. No lesions were observed in mice inoculated with $10^3$ and $10^2$ pfu during the 100 day observation period. Orchitis was noticed on day 23 pi in mice given $10^9$ and $10^8$ pfu, and approximately 7 days later in the other groups ($10^7$ to $10^4$ pfu). Orchitis was especially intense in the $10^9$ and $10^8$ pfu groups and, although receding, was observed until the end of the 100 day observation period. Some pox-like lesions were noticed on the skin of a few mice, occurring around 30–35 days pi. Most pox lesions healed normally between 60–90 days pi. Only one mouse died in the group inoculated with $10^9$ pfu (Day 34 pi) and one mouse died in the group inoculated with $10^8$ pfu (Day 94 pi). No other deaths were observed in the VC-2 inoculated mice.

Mice inoculated with $10^4$ pfu of the WR strain of vaccinia started to display pox lesions on Day 17 pi. These lesions appeared identical to the lesions displayed by the VC-2 injected mice (swollen toes, tail). Mice inoculated with $10^3$ pfu of the WR strain did not develop lesions until 34 days pi. Orchitis was noticed only in the mice inoculated with the highest dose of WR ($10^4$ pfu). During the latter stages of the observation period, lesions appeared around the mouth and the mice stopped eating. All mice inoculated with $10^4$ pfu of WR died or were euthanized when deemed necessary between 21 days and 31 days pi. Four out of the 5 mice injected with $10^3$ pfu of WR died or were euthanized when deemed necessary between 35 days and 57 days pi. No deaths were observed in mice inoculated with lower doses of WR (1 to 100 pfu).

Mice inoculated with the WYETH strain of vaccinia virus at higher doses $5\times10^7$ and $5\times10^8$ pfu) showed lesions on toes and tails, developed orchitis, and died. Mice injected with $5\times10^6$ pfu or less of WYETH showed no signs of disease or lesions.

As shown in Table 19, CY-treated mice provided a more sensitive model for assaying poxvirus virulence than did nude mice. $LD_{50}$ values for the WR, WYETH, and VC-2 vaccinia virus strains were significantly lower in this model system than in the nude mouse model. Additionally, lesions developed in mice injected with WYETH, WR and VC-2 vaccinia viruses, as noted below, with higher doses of each virus resulting in more rapid formation of lesions. As was seen with nude mice, CY-treated mice injected with NYVAC or ALVAC did not develop lesions. However, unlike nude mice, some deaths were observed in CY-treated mice challenged with NYVAC or ALVAC, regardless of the dose. These random incidences are suspect as to the cause of death.

Mice injected with all doses of WYETH ($9.5 \times 10^4$ to $9.5 \times 10^8$ pfu) displayed pox lesions on their tail and/or on their toes between 7 and 15 days pi. In addition, the tails and toes were swollen. Evolution of lesions on the tail was typical of pox lesions with formation of a papule, ulceration and finally formation of a scab. Mice inoculated with all doses of VC-2 ($1.65 \times 10^5$ to $1.65 \times 10^9$) also developed pox lesions on their tails and/or their toes analogous to those of WYETH injected mice. These lesions were observed between 7–12 days post inoculation. No lesions were observed on mice injected with lower doses of WR virus, although deaths occurred in these groups.

Potency Testing of NYVAC-RG. In order to determine that attenuation of the COPENHAGEN strain of vaccinia virus had been effected without significantly altering the ability of the resulting NYVAC strain to be a useful vector, comparative potency tests were performed. In order to monitor the immunogenic potential of the vector during the sequential genetic manipulations performed to attenuate the virus, a rabiesvirus glycoprotein was used as a reporter extrinsic antigen. The protective efficacy of the vectors expressing the rabies glycoprotein gene was evaluated in the standard NIH mouse potency test for rabies (Seligmann, 1973). Table 20 demonstrates that the $PD_{50}$ values obtained with the highly attenuated NYVAC vector are identical to those obtained using a COPENHAGEN-based recombinant containing the rabies glycoprotein gene in the tk locus (Kieny et al., 1984) and similar to $PD_{50}$ values obtained with ALVAC-RG, a canarypox based vector restricted to replication to avian species.

Observations. NYVAC, deleted of known virulence genes and having restricted in vitro growth characteristics, was analyzed in animal model systems to assess its attenuation characteristics. These studies were performed in comparison with the neurovirulent vaccinia virus laboratory strain, WR, two vaccinia virus vaccine strains, WYETH (New York City Board of Health) and COPENHAGEN (VC-2), as well as with a canarypox virus strain, ALVAC (See also Example 11). Together, these viruses provided a spectrum of relative pathogenic potentials in the mouse challenge model and the rabbit skin model, with WR being the most virulent strain, WYETH and COPENHAGEN (VC-2) providing previously utilized attenuated vaccine strains with documented characteristics, and ALVAC providing an example of a poxvirus whose replication is restricted to avian species. Results from these in vivo analyses clearly demonstrate the highly attenuated properties of NYVAC relative to the vaccinia virus strains, WR, WYETH and COPENHAGEN (VC-2) (Tables 14–20). Significantly, the $LD_{50}$ values for NYVAC were comparable to those observed with the avian host restricted avipoxvirus, ALVAC. Deaths due to NYVAC, as well as ALVAC, were observed only when extremely high doses of virus were administered via the intracranial route (Example 11, Tables 14, 15, 19). It has not yet been established whether these deaths were due to nonspecific consequences of inoculation of a high protein mass. Results from analyses in immunocompromised mouse models (nude and CY-treated) also demonstrate the relatively high attenuation characteristics of NYVAC, as compared to WR, WYETH and COPENHAGEN strains (Tables 17 and 18). Significantly, no evidence of disseminated vaccinia infection or vaccinial disease was observed in NYVAC-inoculated animals or ALVAC-inoculated animals over the observation period. The deletion of multiple virulence-associated genes in NYVAC shows a synergistic effect with respect to pathogenicity. Another measure of the inocuity of NYVAC was provided by the intradermal administration on rabbit skin (Tables 17 and 18). Considering the results with ALVAC, a virus unable to replicate in nonavian species, the ability to replicate at the site of inoculation is not the sole correlate with reactivity, since intradermal inoculation of ALVAC caused areas of induration in a dose dependent manner. Therefore, it is likely that factors other than the replicative capacity of the virus contribute to the formation of the lesions. Deletion of specific virulence-associated genes in NYVAC prevents lesion occurrence.

Together, the results in this Example and in foregoing Examples, including Example 10, demonstrate the highly attenuated nature of NYVAC relative to WR, and the previously utilized vaccinia virus vaccine strains, WYETH and COPENHAGEN. In fact, the pathogenic profile of NYVAC, in the animal model systems tested, was similar to that of ALVAC, a poxvirus known to productively replicate only in avian species. The apparently restricted capacity of NYVAC to productively replicate on cells derived from humans (Table 16) and other species, including the mouse, swine, dog and horse, provides a considerable barrier that limits or prevents potential transmission to unvaccinated contacts or to the general environment in addition to providing a vector with reduced probability of dissemination within the vaccinated individual.

Significantly, NYVAC-based vaccine candidates have been shown to be efficacious. NYVAC recombinants expressing foreign gene products from a number of pathogens have elicited immunological responses towards the foreign gene products in several animal species, including primates. In particular, a NYVAC-based recombinant expressing the rabies glycoprotein was able to protect mice against a lethal rabies challenge. The potency of the NYVAC-based rabies glycoprotein recombinant was comparable to the $PD_{50}$ value for a COPENHAGEN-based recombinant containing the rabies glycoprotein in the tk locus (Table 20). NYVAC-based recombinants have also been shown to elicit measles virus neutralizing antibodies in rabbits and protection against pseudorabies virus and Japanese encephalitis virus challenge in swine. The highly attenuated NYVAC strain confers safety advantages with human, animal, medical and veterinary applications (Tartaglia et al., 1992). Furthermore, the use of NYVAC as a general laboratory expression vector system may greatly reduce the biological hazards associated with using vaccinia virus.

By the following criteria, the results of this Example and the Examples herein, including Example 10, show NYVAC to be highly attenuated: a) no detectable induration or ulceration at site of inoculation (rabbit skin); b) rapid clearance of infectious virus from intradermal site of inoculation (rabbit skin); c) absence of testicular inflammation (nude mice); d) greatly reduced virulence (intracranial challenge, both three-week old and newborn mice); e) greatly reduced pathogenicity and failure to disseminate in immunodeficient subjects (nude and cyclophosphamide treated mice); and f) dramatically reduced ability to replicate on a variety of human tissue culture cells. Yet, in spite of being highly attenuated, NYVAC, as a vector, retains the ability to induce strong immune responses to extrinsic antigens.

TABLE 16

Replication of COPENHAGEN (VC-2), NYVAC and ALVAC in avian or human derived cell lines

| Cells | Hours post-infection | Yield[a] VC-2 | NYVAC | ALVAC | % Yield |
|---|---|---|---|---|---|
| CEF | 0 | 3.8[b] | 3.7 | 4.5 | |
| | 24 | 8.3 | 7.8 | 6.6 | |
| | 48 | 8.6 | 7.9 | 7.7 | |
| | 72 | 8.3 | 7.7 | 7.5 | 25 |
| | 72A[c] | <1.4 | 1.8 | 3.1 | |
| MRC-5 | 0 | 3.8 | 3.8 | 4.7 | |
| | 72 | 7.2 | 4.6 | 3.8 | 0.25 |
| | 72A | 2.2 | 2.2 | 3.7 | |
| WISH* | 0 | 3.4 | 3.4 | 4.3 | |
| | 72 | 7.6 | 2.2 | 3.1 | 0.0004 |
| | 72A | —[d] | 1.9 | 2.9 | |
| DETROIT | 0 | 3.8 | 3.7 | 4.4 | |
| | 72 | 7.2 | 5.4 | 3.4 | 1.6 |
| | 72A | 1.7 | 1.7 | 2.9 | |
| HEL | 0 | 3.8 | 3.5 | 4.3 | |
| | 72 | 7.5 | 4.6 | 3.3 | 0.125 |
| | 72A | 2.5 | 2.1 | 3.6 | |
| JT-1 | 0 | 3.1 | 3.1 | 4.1 | |
| | 72 | 6.5 | 3.1 | 4.2 | 0.039 |
| | 72A | 2.4 | 2.1 | 4.4 | |
| HNK | 0 | 3.8 | 3.7 | 4.7 | |
| | 72 | 7.6 | 4.5 | 3.6 | 0.079 |
| | 72A | 3.1 | 2.7 | 3.7 | |

[a]Yield of NYVAC at 72 hours post-infection expressed as a percentage of yield of VAC-2 after 72 hours on the same cell line.
[b]Titer expressed as $LOG_{50}$ pfu per ml.
[c]Sample was incubated in the presence of 40 μg/ml of cytosine arabinoside.
[d]Not determined.
*ATCC #CCL25 Human amnionic cells.

TABLE 17

Induration and ulceration at the site of intradermal inoculation of the rabbit skin

| VIRUS STRAIN | DOSE[a] | INDURATION Size[b] | Days[c] | ULCERATION Size | Days |
|---|---|---|---|---|---|
| WR | $10^4$ | 386 | 30 | 88 | 30 |
| | $10^5$ | 622 | 35 | 149 | 32 |
| | $10^6$ | 1057 | 34 | 271 | 34 |
| | $10^7$ | 877 | 35 | 204 | 35 |
| | $10^8$ | 581 | 25 | 88 | 26 |
| WYETH | $10^4$ | 32 | 5 | —[d] | — |
| | $10^5$ | 116 | 15 | — | — |
| | $10^6$ | 267 | 17 | 3 | 15 |
| | $10^7$ | 202 | 17 | 3 | 24 |
| | $10^8$ | 240 | 29 | 12 | 31 |
| VC-2 | $10^4$ | 64 | 7 | — | — |
| | $10^5$ | 86 | 8 | — | — |
| | $10^6$ | 136 | 17 | — | — |
| | $10^7$ | 167 | 21 | 6 | 10 |
| | $10^8$ | 155 | 32 | 6 | 8 |
| NYVAC | $10^4$ | — | — | — | — |
| | $10^5$ | — | — | — | — |
| | $10^6$ | — | — | — | — |
| | $10^7$ | — | — | — | — |
| | $10^8$ | — | — | — | — |

[a]pfu of indicated vaccinia virus in 0.1 ml PBS inoculated intradermally into one site.
[b]mean maximum size of lesions (mm²)
[c]mean time after inoculation for complete healing of lesion.
[d]no lesions discernable.

TABLE 18

Persistence of poxviruses at the site of intradermal inoculation

| Virus | Inoculum Dose | Total Virus Recovered |
|---|---|---|
| WR | 8.0[a] | 6.14 |
| | 7.0 | 6.26 |
| | 6.0 | 6.21 |
| WYETH | 8.0 | 3.66 |
| | 7.0 | 4.10 |
| | 6.0 | 3.59 |
| VC-2 | 8.0 | 4.47 |
| | 7.0 | 4.74 |
| | 6.0 | 3.97 |
| NYVAC | 8.0 | 0 |
| | 7.0 | 0 |
| | 6.0 | 0 |

[a]expressed as $log_{10}$ pfu.

TABLE 19

Virulence studies in immunocompromised mice

| | $LD_{50}$[a] | |
|---|---|---|
| Poxvirus Strain | Nude mice | Cyclophosphamide treated mice |
| WR | 422 | 42 |
| VC-2 | $>10^9$ | $<1.65 \times 10^5$ |
| WYETH | $1.58 \times 10^7$ | $1.83 \times 10^6$ |
| NYVAC | $>5.50 \times 10^8$ | $7.23 \times 10^8$ |
| ALVAC | $>10^9$ | $\geq 5.00 \times 10^{8b}$ |

[a]Calculated 50% lethal dose (pfu) for nude or cyclophosphamide treated mice by the indicated vaccinia viruses and for ALVAC by intraperitoneal route.
[b]5 out of 10 mice died at the highest dose of $5 \times 10^8$ pfu.

TABLE 20

Comparative efficacy of NYVAC-RG and ALVAC-RG in mice

| Recombinant | $PD_{50}$[a] |
|---|---|
| VV-RG | 3.74 |
| ALVAC-RG | 3.86 |
| NYVAC-RG | 3.70 |

[a]Four to six week old mice were inoculated in the footpad with 50–100 μl of a range of dilutions (2.0–8.0 $log_{10}$ tissue culture infection dose 50% ($TCID_{50}$)) of either the VV-RG (Kieny et al., 1984), ALVAC-RG (vCP65) or NYVAC-RG (vP879). At day 14, mice of each group were challenged by intracranial inoculation of 30 μl of a live CVS strain rabies virus corresponding to 15 lethal dose 50% ($LD_{50}$) per mouse. At day 28, surviving mice were counted and aprotective dose 50% ($PD_{50}$) was calculated.

EXAMPLE 12

GENERATION OF A NYVAC AND ALVAC RECOMBINANT EXPRESSING RHDV CAPSID

Cell Lines and Virus Strains

The rescuing viruses used in the production of the NYVAC recombinant vP1249 and the canarypox recombinant vCP309 were respectively, the NYVAC virus vP866 (Tartaglia et al. 1992) and the canarypox ALVAC (CPpp) (Taylor et al. 1991). RHDV (Saône et Loire isolate) was obtained from infected rabbits in France. Viruses were grown and titers were determined on either Vero or CEF cell monolayers.

Viral Propagation and RNA Preparation.

RHDV (Saone et Loire isolate) was propagated in rabbits after intramuscular injection of filtered liver homogenates. Livers from animals which died from RHDV infection were frozen at −70° C. Total RNA preparation was performed using a procedure based on the Chomczynski and Sachi (1987) method. All enzymes described in this report were purchased from Boehringer Mannheim Gmbh (Germany).

Briefly, 2.0 g of infected rabbit liver tissue was ground using a mortar and pestle in the presence of liquid nitrogen followed by sequential extraction with 0.1 ml sodium acetate (2M, pH 4.0), 1.0 ml H$_2$O saturated phenol and 0.2 ml chloroform:isoamyl alcohol (49:1). The final emulsion was mixed vigorously and placed on ice for 15 minutes before being centrifuged at 13K rpm for 20 minutes at 4° C. Nucleic acid was recovered by addition of isopropanol and centrifugation at 13K rpm for 20 minutes at 4° C. The pellet was dissolved by heating at 65° C. for 5 minutes in 0.2 ml of a 3M guanidine thiocyanate solution containing 20 mM sodium citrate and 0.37% sarkosyl and made 0.5 M 2-mercaptethanol on day of use. The RNA pellet was recovered by centrifugation at 13K rpm at 4° C. and washed twice with cold 75% ethanol before being resuspended in 50 μl of diethylpyrocarbonate (DEPC) treated H$_2$O. All solutions were made with DEPC-treated water.

cDNA Cloning of the RHDV Capsid Gene.

Total RNA was used to generated first strand CDNA as previously described (Taylor et al. 1990). Single stranded CDNA, was subsequently heated at 95° C. for 5 minutes and cooled on ice before being mixed with 5 μl of 10×PCR buffer, 3.75 μl of 2 mM dNTPs, 5 μl of 5 μM 5'end primer (SEQ ID NO:40) 5' CTGGAATTCTATCGCGATATCCGTTAAGTTTGTATCGTAATGGAGGGCAAAGCCCGT 3', 5 μl of 5 μM 3'end primer (SEQ ID NO:41) 5'GTAAGCTTATCAGACATAAGAAAAGCC 3', 26 μl $H_2O$ and 0.25 μl of Taq polymerase (5.0 u/μl). A 30 cycle PCR amplification was performed in a 0.5 ml tube containing 40 μl of mineral oil using the following profile: 94° C. 1 minute, 60° C. 1 minute and 72° C. 1 minute. The PCR aqueous phase reaction was phenolchloroform extracted and ethanol precipitated before being digested by EcoRI and HindIII. The amplified 1.8 bp DNA fragment was purified on a 1% agarose gel and isolated using the Gene Clean procedure according to the manufacturer (Bio 101, Inc., La Jolla, Calif.) specifications, before being ligated into the corresponding sites of the vector pBluescript SK+ (Stratagene, La Jolla, Calif.) generating plasmid pLF11.

Mutagenesis Experiments.

To remove the first potential early transcription termination signal (STAT position # 1600, FIG. 12A) (Yuen and Moss, 1987), a double mutation was based on a PCR amplification of pLF11 DNA with the primers LF093 (SEQ ID NO:42) (5'- TGGCAGTTAACCTTTGCATCTGGTTTCATGGAGATCGGTTTAAGTGTGGACGGGTACTTCTATGC A-3') and LF094 (SEQ ID NO:43) (5'- TATAAGCTTTCAGACATAAGAAAAGCC-3'). The 190 bp resultant fragment was digested with HpaI and HindIII and subsequently purified and ligated with the 4.5 bp HindIII/HpaI pLF11 fragment, generating pLF11a. To remove the second potential early transcription termination signal (5TAT position # 213, FIG. 12A), a second double mutation was engineered by a double round PCR amplification in pLF11a DNA. A first PCR round was performed on pLF11a DNA using the following primer couples [LF070 (SEQ ID NOS:44,45) 5'- TCATTCGAATTCTATCGCGATATCCGTTAAGTTTGTATCGTAATG-3')/LF095 (5'- ATTGTAATAGAAGTTTGTTCT-3')] and [LF096 (SEQ ID NOS:46,47) (5'- AGAACAAACTTCTATTACAAT-3')/LF097 (5'-GCGAAACTGCATGCCACCAGC-3')] generating two partially overlapping DNA fragments of 250 bp and 140 bp, respectively. The second round of PCR amplification was performed in presence of both partially overlapping purified 250 bp and 140 bp DNA fragments and both external primers LF070 and LF097. The resultant 380 bp DNA fragment was digested with EcoRI and SphI before being purified and ligated with the EcoRI/SphI 4.3K bp DNA fragment of pLF11a, generating pLF11b. All PCR amplifications were performed using the conditions previously described.

Construction of the Donor Plasmid pLF14.

The 1.8 bp NruI/HindIII DNA fragment of pLF11b was purified and ligated with the 4.5 bp NruI/HindIII DNA fragment of a modified pBluescript SK+ plasmid containing the 100 bp NruI/HinfI DNA fragment of the vaccinia early/late H6 promoter (Perkus et al.1989) cloned between the canary pox C6 locus left (377 bp) and right (1155 bp) arms (Goebel et al. 1995), generating pLF14.

Construction of the Donor Plasmid pLF12.

The 1.8 bp NruI/BamHI DNA fragment of pLF11b was purified and ligated with the 3.6 bp NruI/BamHI DNA fragment of. pSD550VC, generating pLF12. To derive pSD550VC a polylinker containing the BglII and BamHI restrictions sites was cloned between the pSD548 (Tartaglia et al., 1992) BglII and SmaI sites and the vaccinia early/late H6 promoter was subsequently introduced into the BglII site.

Nucleotide Sequencing and Sequence Analysis

Plasmid DNA was sequenced according to Sequenase 2.0 kit instructions (US Biochemical) and sequence analysis was performed using the PC Gene software (Intelligenetics).

In Vivo Recombination, Purification, Amplification and Concentration of the NYVAC Recombinant vP1249 and the Canarypoxvirus Recombinant vCP309.

Recombination experiments were performed as previously described (Perkus et al. 1993) using pLF14 and pLF12 as donor DNAs and ALVAC (CPpp) and NYVAC as rescue viruses, respectively. Viruses were plated on CEF monolayers under agarose and recombinant plaques were identified by in-situ hybridization using a radiolabelled probe specific for the entire RHDV capsid gene, as described in Perkus et al., 1993. For each recombination experiment a positive plaque was purified and the recombinant virus was amplified and concentrated according to Taylor et al. (1991).

Radioimmunoprecipitation and Polyacrylamide Gel Electrophoresis.

Radioimmunoprecipitation analyses were performed as previously described (Pincus et al. 1992) using [$^{35}$S] methionine (1000 Ci/mmol, NEN) labelled lysates derived from either vCP309 or vP1249 infected Vero cells and RHDV monoclonal antibodies preparations (3H6 and 1H8) (Wirblich et al. 1994). Immunoprecipitates were fractioned on a 10% SDS-PAG. The precipitated polypeptides species were visualized by standard fluorography using sodium salicylate (Sambrook et al. 1989).

FACs Analysis of vCP309 Infected Cells.

FACScan analysis was conducted as described in Tine et al. (1990) using the RHDV monoclonal antibodies 3H6 and 1H8.

Rabbit VHD Challenge Study.

Groups of four, five or nine week old SPF rabbits were vaccinated (0.2 ml doses) either via the subcutaneous or intradermal routes with vCP309. Vaccine groups were inoculated with either $10^5$ or $10^7$ plaque-forming-units (pfu) of vCP309 on day 0. One group of four SPF rabbits was vaccinated intradermally with $10^7$ plaque-forming-units (pfu) of vP1249 on day 0. For those groups which received a booster injection on day 28 (Table 21), the second injection was done with the same inoculum. A live RHDV challenge exposure was administrated on day 42 using $10^2$ $LD_{50}$ of the LST L4/90.10 RHDV strain. The animals were observed for an 8-day period before the surviving animals were necropsied and inspected for RHDV-induced lesions. Blood samples were collected on days 28 and 42. Anti-RHDV antibodies were titrated in both an ELISA and a hemagglutination inhibition assay (HIA).

Sequences Analysis of the Capsid Gene.

Using a nucleotide sequence for another RHDV isolate (Meyers et al. 1991) to design primers homologous to the 3' portion of the genomic RHDV RNA for the subsequent PCR amplification of the putative capsid gene region of a RHDV (Saône et Loire strain), the derived 1,740 bp DNA sequence of the RHDV capsid gene and the deduced amino-acid sequence are shown in FIG. 12A. Nucleotide sequence comparison with the RHDV genomic sequence for another isolate (Meyers et al. 1991) shows 97.3% sequence identity over the complete capsid gene. The same analysis at the amino acid level demonstrates an even higher homology (99.1%). Nine putative N-glycosylation sites centered on Asn # 45, 281, 308, 369, 393, 430, 474, 481 and 502 can be predicted from the deduced amino-acid sequence. Interestingly, eight of them are localized in the carboxy half of the capsid gene primary sequence.

Construction of the ALVAC-Based Recombinant Virus vCP309 and the NYVAC-Based Recombinant Virus vP1249.

Figure 13:
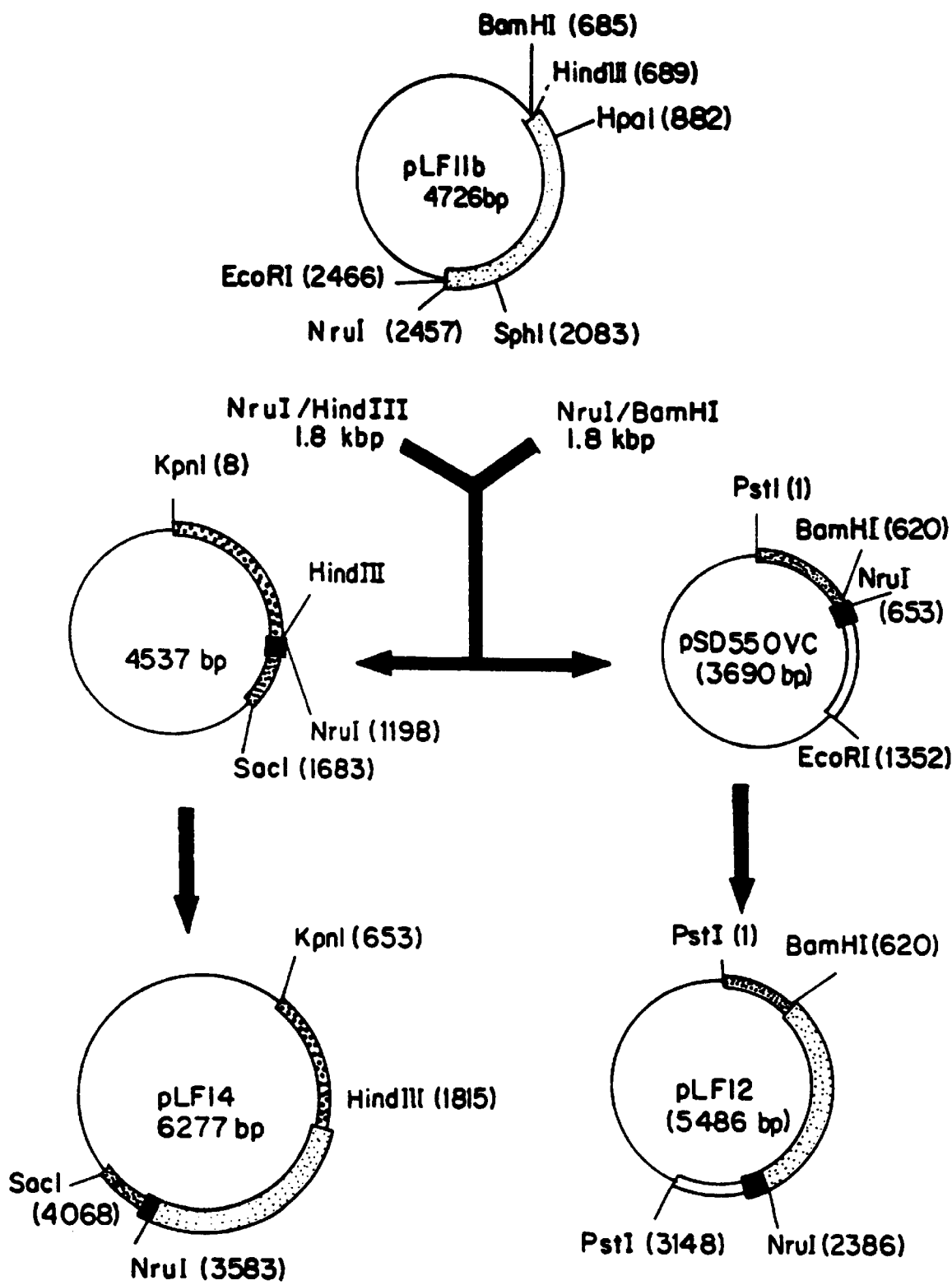
FIG. 13 shows a schematic construction of the donor plasmid pLF14 and pLF12 (A 1.8 kbp NruI/HindIII and a 1.8 kbp NruI/BamHI DNA fragments from pLF11b, both containing the RHDV capsid coding sequence and the first 30 bp of the vaccinia H6 promoter, were ligated respectively with either the 4.5 kbp NruI/HindIII DNA fragment of a modified pBluescript SK+ plasmid containing the remaining of the H6 promoter cloned between the canarypox C6 locus right and left flanking arms or with the 3.7 kbp NruI/BamHI DNA fragment of pSD550VC; the resulting plasmids pLF14 and pLF12 were used in in vitro recombination experiments to generate the recombinants ALVAC vCP309 and NYVAC vP1249, respectively); and, FIG. 14 shows immunoprecipitations of the RHDV recombinant capsid protein from vCP309 and vP1249 infected Vero cells (immunoprecipitations were performed as described in the Examples using RHDV MAbs 1H8 (lanes 1–5) and 3H6 (lanes 6–10), respectively; Lanes 1 and 6, uninfected Vero cells; lanes 2 and 7, Vero cells infected with the parental canarypox ALVAC (CPpp); lanes 3 and 8, Vero cells infected with the parental NYVAC; lanes 4 and 9, Vero cells infected with the recombinant vCP309; lanes 5 and 10, Vero cells infected with the recombinant vP1249; figures in the left hand margin correspond to the migration of standard molecular weight markers).

The ALVAC vCP309 and NYVAC vP1249 recombinant viruses, expressing the RHDV putative capsid gene were developed using a strategy similar to that previously described (Perkus et al. 1993). FIG. 13 depicts the engineering of the donor plasmids pLF14 and pLF12, utilized to yield vCP309 and vP1249, respectively, with FIG. 12B showing the sequence of the canarypox C6 locus flanking arms in pLF14 (1,162 bp KpnI\HindIII and 386 bp HinfI\SacI sequences correspond respectively to right and left flanking arms). No amino acid analysis of the RHDV capsid gene NH2- extremity was available prior to this invention. However, since members of the Calicivirus family express their capsid polypeptide from the 3' end of their genome and since the calculated molecular weight (60.257 Da) of the polypeptide encoded by the ORF initiated at Met#1766 in Meyers et al. (1991) would be in good agreement with the size of the polypeptide detected in purified virus preparations (Prieto et al. 1990), the RHDV capsid gene NH2- extremity was assumed to correspond to Met#1766 in the sequence described in (Meyers et al. 1991).

Immunoprecipitation Analysis of the RHDV Capsid Expressed by vCP309 and vP1249.

Figure 14:
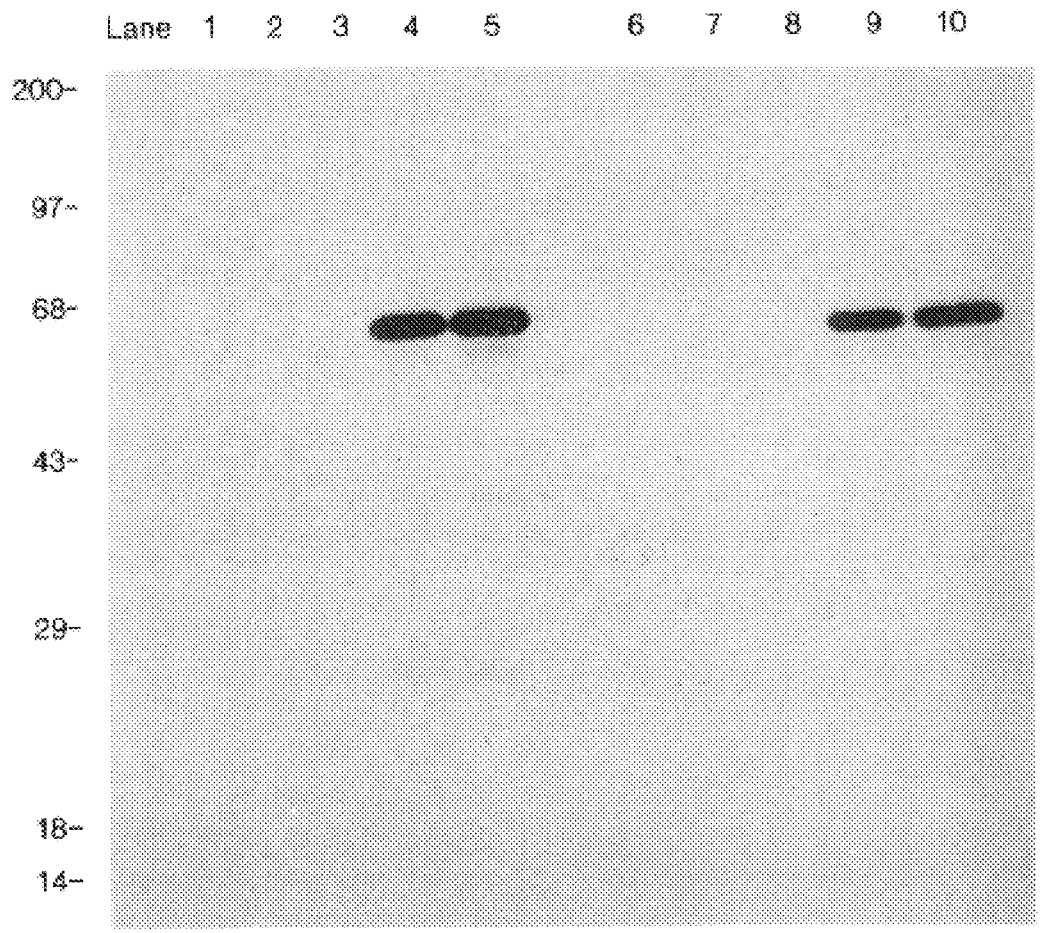

In order to demonstrate that vCP309 and vP1249 both express an authentic capsid protein, immunoprecipitation experiments were performed using the monoclonal antibodies preparations, 3H6 and 1H8. Briefly, Vero cell monolayers were infected at 10 PFU per cell with either parental or the appropriate recombinant virus in the presence of [$^{35}$S] methionine. The recombinant RHDV capsid protein was immunoprecipitated from the infected lysates as described. No radio labeled product was detected in uninfected Vero cell lysates (FIG. 4, lanes 1 and 6) or in parental-ALVAC or NYVAC-infected Vero cell lysates (FIG. 14, lanes 2–3 and 7–8). Significantly, a polypeptide with an apparent molecular weight of 60 kDa was precipitated from vCP309 Vero cell lysates by monoclonal antibodies 1H8 and 3H6 (FIG. 14, lanes 4 and 9, respectively). Similarly, a polypeptide with the same apparent molecular weight was precipitated from vP1249 Vero cell lysates by monoclonal antibodies 1H8 and 3H6 (FIG. 14, lanes 5 and 10, respectively). The estimated molecular weight of 60 kDa is consistent with both the predicted molecular mass from the deduced RHDV capsid sequence and SDS-PAGE analysis of purified virus (Prieto and Parra, 1990). Further, this shows that the initiation codon (ATG) described above does indeed constitute the authentic translation initiation codon. The 26- and 36-kDa polypeptides which had been previously described in purified RHDV samples (Meyers et al. 1991; Rodak et al. 1990) and in lysates derived from baculovirus RHDV capsid recombinant virus (Laurent et al. 1994) were not detected in either vCP309 or vP1249 cell lysates.

FACScan analysis performed with the same MAbs and vCP309 or vP1249 infected Vero cells confirmed RHDV expression in vCP309 or vP1249 infected cells. Further, results from such analyses demonstrated internal capsid expression but no expression on the surface of infected cells.

Protective Immunity Induced in Rabbits by ALVAC Recombinant vCP309 and NYVAC Recombinant Virus vP1249.

The protective immunity induced in rabbits by ALVAC recombinant vCP309 was analyzed using a factorial matrix which combines the effects of the route of administration, the age of the animal at the initial vaccination, the presence of a booster injection and the dose of vCP309. All rabbits immunized with one or two doses of $10^7$ pfu of vCP309 survived a strong lethal RHDV challenge which killed 100% of the non vaccinated animals (Table 21, lanes 1–5). Necropsy of 14 out of these 16 rabbits one week after challenge failed to detect any RHDV-induced lesions. When rabbits were vaccinated with $10^5$ pfu of vCP309, 4 out of 16 (25%) died and RHDV-induced lesions were apparent in 3 surviving animals (Table 21, lanes 6–9). These results indicate a clear effect of the vaccine dosage (Student t=1.9) but only a weaker effect of the route of administration (Student t=1.2). Serological analysis indicate that the principal effect is related to vCP309 dosage (Student t=1.6) but no clear correlations between protection and antibodies titers can be evidenced.

The protective immunity induced in rabbits by NYVAC recombinant vP1249 was analyzed in one group of rabbits vaccinated intradermally with two inoculations of $10^7$ pfu of vP1249. All four rabbits survived the challenge but RHDV-induced lesions were apparent in 1 surviving animal (Table 21, lanes 10).

TABLE 21

Protection of rabbits vaccinated with recombinants vCP309 and vP1249 against lethal RHDV challenge.

| Grp # | vCP309[a] | Age[b] | Booster[c] | Route[d] | HAI[g] d28 | d42 | ELISA[e] d28 | d42 | Deaths[f] | Lesion[g] | PROTECTION (%) |
|---|---|---|---|---|---|---|---|---|---|---|---|
| 1[h] | — | | | — | <5 | <5 | <5 | <5 | 6 | | 0 |
| 2 | 7 | 5 | Yes | sc | 9 | 181 | 5 | 143 | 0 | 0 | 100 |
| 3 | 7 | 9 | No | sc | ND | <5 | ND | <5 | 0 | 1 | 75 |

TABLE 21-continued

Protection of rabbits vaccinated with recombinants vCP309 and vP1249 against lethal RHDV challenge.

| Grp # | vCP309[a] | Age[b] | Booster[c] | Route[d] | HAI[g] d28 | d42 | ELISA[e] d28 | d42 | Deaths[f] | Lesion[g] | PROTECTION (%) |
|---|---|---|---|---|---|---|---|---|---|---|---|
| 4 | 7 | 5 | No | id | 27 | 9 | 17 | 7 | 0 | 0 | 100 |
| 5 | 7 | 9 | Yes | id | 10 | 133 | 6 | 59 | 0 | 1 | 75 |
| 6 | 5 | 5 | No | sc | <5 | <5 | 8 | <5 | 1 | 0 | 75 |
| 7 | 5 | 9 | Yes | sc | <5 | <5 | 8 | 32 | 1 | 0 | 75 |
| 8 | 5 | 5 | Yes | id | <5 | <5 | <5 | <5 | 0 | 3 | 25 |
| 9 | 5 | 9 | No | id | ND | <5 | ND | 34 | 2 | 0 | 50 |
| 10 | | 9 | Yes | id | 20 | 100 | 12 | 106 | 0 | 1 | 75 |

[a]Expressed in $\log_{10}$ pfu of vCP309 or vP1249.
[b]Age in weeks at the primo-vaccination (d0).
[c]At d28 with the same amount of virus used at d0.
[d]Inoculation routes were either subcutaneous (sc) or intradermal (id).
[e]For each group, mean value of 4 rabbits.
[f]Challenge at d42 with RHDV LST L4/90.10 at $10_2$ $LD_{50}$ (0.5 ml).
[g]RHDV pulmonary or hepatic lesions at necropsy on surviving rabbits.
[h]Control group of unchallenged rabbits.

The results presented here demonstrate the ability of the NYVAC and ALVAC-calicivirus (e.g., RHDV) recombinants and products therefrom to be employed in the compositions and utilities aforementioned, for instance, immunological, antigenic or vaccine compositions, or for use in preparing antigens or antibodies for assays, kits or tests, as suitable for uses in vaccine or immunization strategies; and, to provide DNA for probes or to generate DNA primers for detection or amplification of calicivirus (e.g., RHDV) DNA.

Having thus described in detail preferred embodiments of the present invention, it is to be understood that the invention defined by the appended claims is not to be limited by particular details set forth in the above description as many apparent variations thereof are possible without departing from the spirit or scope thereof.

REFERENCES

1. Altenburger, W., C-P. Suter and J. Altenburger, Archives Virol. 105:15–27 (1989).
2. Behbehani, A. M., Microbiological Reviews 47:455–509 (1983).
3. Bergoin, M., and Dales, S., In Comparative Virology, eds. K. Maramorosch and E. Kurstak, (Academic Press, NY) pp. 169–205 (1971).
4. Bertholet, C., Drillien, R., and Wittek, R., Proc. Natl. Acad. Sci. USA 82:2096–2100 (1985).
5. Buller, R. M. L., G. L. Smith, Cremer, K., Notkins, A. L., and Moss, B., Nature 317:813–815 (1985).
6. Buller, R. M. L., Chakrabarti, S., Cooper, J. A., Twardzik, D. R., and Moss, B., J.Virol. 62:866–874 (1988).
7. Cadoz, M., A. Strady, B. Meignier, J. Taylor, J. Tartaglia, E. Paoletti and S. Plotkin, The Lancet, 339:1429 (1992).
8. Child, S. J., Palumbo, G. J., Buller, R. M. L., and Hruby, D. E. Virology 174:625–629 (1990).
9. Clewell, D. B. and D. R. Helinski, Proc. Natl. Acad. Sci. USA 62:1159–1166 (1969).
10. Clewell, D. B., J. Bacteriol 110:667–676 (1972).
11. Colinas, R. J., R. C. Condit and E. Paoletti, Virus Research 18:49–70 (1990).
12. Cooney, E. L., Corrier, A. C., Greenberg, P. D., et al., Lancet 337:567–572 (1991).
13. Dreyfuss, G., Adam, S. A., and Choi, Y. D., Mol. Cell. Biol. 4:415–423 (1984).
14. Edbauer, C., R. Weinberg, J. Taylor, A. Rey-Senelonge, J. F. Bouquet, P. Desmettre, E. Paoletti, Virology 179:901–904 (1990).
15. Engelke, D. R., Hoener, P. A., Collins, F. S., Proc. Natl. Acad. Sci. USA 85:544–548 (1988).
16. Fenner, F., Virology 5:502–529 (1958).
17. Flexner, C., Hugen, A., and Moss, B., Nature 330:259–262 (1987).
18. Fries et al., 32nd Interscience Conference on Antimicrobial Agents and Chemotherapy, Anaheim, Calif. (October 1992).
19. Funahashi, S., T. Sato and H. Shida, J. Gen. Virol. 69:35–47 (1988).
20. Ghendon, Y. Z., and Chernos, V. I., Acta Virol. 8:359–368 (1964).
21. Gillard, S., Spehner, D., Drillien, R., and Kirn, A., Proc. Natl. Acad. Sci. USA 83:5573–5577 (1986).
22. Goebel, S. J., Johnson, G. P., Perkus, M. E., Davis, S. W., Winslow, J. P., Paoletti, E., Virology 179:247–266 (1990a).
23. Goebel, S. J., G. P. Johnson, M. E. Perkus, S. W. Davis, J. P. Winslow and E. Paoletti, Virology 179:517–563 (1990b).
24. Goldstein, D. J. and S. K. Weller, Virology 166:41–51 (1988).
25. Guo, P., Goebel, S., Davis, S., Perkus, M. E., Languet, B., Desmettre, P., Allen, G., and Paoletti, E., J. Virol. 63:4189–4198 (1989).
26. Guo et al., J. Virol. 64:2399–2406 (1990).
27. Hruby, D. E., R. A. Maki, D. B. Miller and L. A. Ball, Proc. Natl. Acad. Sci. USA 80:3411–3415 (1983).
28. Hruby, D. E. and L. A. Ball, J. Virol. 43:403–409 (1982).
29. Ichihashi, Y. and Dales, S., Virology 46:533–543 (1971).
30. Itamura, S., H. Iinuma, H. Shida, Y. Morikawa, K. Nerome and A. Oya, J. Gen. Virol. 71:2859–2865 (1990).
31. Jacobson, J. G., D. A. Leib, D. J. Goldstein, C. L. Bogard, P. A. Schaffer, S. K. Weller and D. M. Coen, Virology 173:276–283 (1989).
32. Jamieson, A. T., G. A. Gentry and J. H. Subak-Sharpe, J. Gen. Virol. 24:465–480 (1974).
33. Kato, S., M. Takahashi, S. Kameyama and J. Kamahora, Biken's 2:353–363 (1959).
34. Kieny, M. P., Lathe, R., Drillien, R., Spehner, D., Skory, S., Schmitt, D., Wiktor, T., Koprowski, H., and Lecocq, J. P., Nature (London) 312:163–166 (1984).
35. Konishi et al., Virology 190:454–458 (1992).
36. Kotwal, G. J. and Moss, B., Nature (London) 335:176–178 (1988).
37. Kotwal, G. J., S. N. Isaacs, R. McKenzie, M. M. Frank and B. Moss, Science 250:827–830 (1990).

38. Kotwal, G. J., A. W. Hugin and B. Moss, Virology 171:579–587 (1989a).
39. Kotwal, G. J. and B. Moss, J. Virol. 63:600–606 (1989b).
40. Mandecki, W., Proc. Natl. Acad. Sci. USA 83:7177–7182 (1986).
41. Maniatis, T., Fritsch, E. F., and Sambrook, J., In Molecular cloning: a laboratory manual, (Cold Spring Harbor Laboratory, Cold Spring Harbor, N.Y.) (1982).
42. Matthews, R. E. F., Intervirology 17:42–44 (1982).
43. Morgan, A. J., M. Mackett, S. Finerty, J. R. Arrand, F. T. Scullion and M. A. Epstein, J. Med. Virol. 25:189–195 (1988).
44. Morisse, J. P., Le Gall, G., & E. Boilletot. Bull. Soc. Vet. Prat. de France (1990).
45. Moss, B., E. Winters and J. A. Cooper, J. Virol. 40:387–395 (1981).
46. Palumbo, G. J., Pickup, D. J., Fredrickson, T. N., Mcintyre, L. J., and Buller, R. M. L., Virology 172:262–273 (1989).
47. Panicali, D. and E. Paoletti, Proc. Natl. Acad. Sci. USA 79:4927–4931 (1982).
48. Panicali, D., Davis, S. W., Mercer, S. R., and Paoletti, E., J. Virol. 37:1000–1010 (1981).
49. Patel, D. D. and Pickup, D. J., EMBO 6:3787–3794 (1987).
50. Patel, D. D., Ray, C. A., Drucker, R. P., and Pickup, D. J., Proc. Natl. Acad. Sci. USA 85:9431–9435 (1988).
51. Perkus, M. E., Goebel, S. J., Davis, S. W., Johnson, G. P., Limbach, K., Norton, E. K., and Paoletti, E., Virology 179:276–286 (1990).
52. Perkus, M. E., S. J. Goebel, S. W. Davis, G. P. Johnson, E. K. Norton and E. Paoletti, Virology 180:406–410 (1991).
53. Perkus, M. E., Limbach, K., and Paoletti, E., J. Virol. 63:3829–3836 (1989).
54. Perkus, M. E., A. Piccini, B. R. Lipinskas and E. Paoletti, Science 229:981–984 (1985).
55. Perkus, M. E., D. Panicali, S. Mercer and E. Paoletti, Virology 152:285–297 (1986).
56. Piccini, A., M. E. Perkus, and E. Paoletti, Methods in Enzymology 153:545–563 (1987).
57. Pickup, D. J., B. S. Ink, B. L. Parsons, W. Hu and W. K. Joklik, Proc. Natl. Acad. Sci. USA 81:6817–6821 (1984).
58. Pickup, D. J., B. S. Ink, W. Hu, C. A. Ray and W. K. Joklik, Proc. Natl. Acad. Sci. USA 83:7698–7702 (1986).
59. Rodak, L, Granatova, M., Smid, L. V., Vesely, T., & Z. Neverorankova. J. Gen. Virol. 71:2593–2598 (1990).
60. Sanger, F., Nickel, S. Coulson, A. R., Proc. Natl. Acad. Sci. 74:5463–5467 (1977).
61. Schmidtt, J. F. C. and H. G. Stunnenberg, J. Virol. 62:1889–1897 (1988).
62. Shapira, S. K., Chou, J., Richaud, F. V. and Casadaban, M. J., Gene 25:71–82 (1983).
63. Shida, H., Hinuma, Y., Hatanaka, M., Morita, M., Kidokoro, M., Suzuki, K., Maruyzam, T., Takahashi-Nishimaki, F., Sugimoto, M., Kitamura, R., Miyazawa, T., and Hayami, M., J. Virol. 62:4474–4480 (1988).
64. Shida, H., Virology 150:451–462 (1986).
65. Shida, H., T. Tochikura, T. Sato, T. Konno, K. Hirayoshi, M. Seki, Y. Ito, M. Hatanaka, Y. Hinuma, M. Sugimoto, F. Takahashi-Nishimaki, T. Maruyama, K. Miki, K. Suzuki, M. Morita, H. Sashiyama and M. Hayami, EMBO 6:3379–3384 (1987).
66. Slabaugh, M., N. Roseman, R. Davis and C. Mathews, J. Virol. 62:519–527 (1988).
67. Smith, J. S., P. A. Yager and G. M. Baer, In Laboratory Techniques in Rabies, eds. M. M. Kaplan and H. Koprowski (WHO Geneva) pp. 354–357 (1973).
68. Stanbery, L. R., Kit, S., Myers, M. G., J. Virol. 55:322–328 (1985).
69. Tabor, S. and C. C. Richardson, Proc. Natl. Acad. Sci. USA 84:4767–4771 (1987).
70. Tartaglia, J., Jarrett, O., Neil, J. C., Desmettre, P., Paoletti, E., J. Virol. 67:2370–2375 (1993).
71. Tartaglia, J., Perkus, M. E., Taylor, J., Norton, E. K., Audonnet, J.-C., Cox, W. I., Davis, S. W., Van der Hoeven, J., Meignier, B., Riviere, M., Languet, B., Paoletti, E., Virology 188:217–232 (1992).
72. Tartaglia, J., J. Taylor, W. I. Cox, J.-C. Audonnet, M. E. Perkus, A. Radaelli, C. de Giuli Morghen, B. Meignier, M. Riviere, K. Weinhold & E. Paoletti, In AIDS Research Reviews, eds. W. Koff, F. Wong-Staal & R. C. Kenedy, Vol. 3, (Marcel Dekker, NY) pp. 361–378 (1993a).
73. Tartaglia, J., Pincus, S., Paoletti, E., Critical Reviews in Immunology 10:13–30 (1990a).
74. Taylor, G., E. J. Stott, G. Wertz and A. Ball, J. Gen. Virol. 72:125–130 (1991a).
75. Taylor, J., C. Trimarchi, R. Weinberg, B. Languet, F. Guillemin, P. Desmettre and E. Paoletti, Vaccine 9:190–193 (1991b).
76. Taylor, J., Weinberg, R., Kawaoka, Y., Webster, R. G., and Paoletti, E., Vaccine 6:504–508 (1988a).
77. Taylor, J., R. Weinberg, B. Lanquet, P. Desmettre, and E. Paoletti, Vaccine 6:497–503 (1988b).
78. Taylor, J., R. Weinberg, J. Tartaglia, C. Richardson, G. Alkhatib, D. Briedis, M. Appel, E. Norton & E. Paoletti, Virology 187:321–328 (1992).
79. Taylor, J., Edbauer, C., Rey-Senelonge, A., Bouquet, J.-F., Norton, E., Goebel, S., Desmettre, P., & E. Paoletti, J. Virol. 64:1441–1450 (1990).
80. Tine, J. A., Walsh, A., Rathburn, D., Leonard, L., Wakeland, E. K., Dilwith, R., & L. Flaherty, Immunogenetics 31:315–325 (1990).
81. Weir, J. P. and B. Moss, J. Virol. 46:530–537 (1983).
82. Yuen, L., and Moss, B., Proc. Natl. Acad. Sci. USA 84:6417–6421 (1987).
83. Zhou, J., L. Crawford, L. McLean, X. Sun, M. Stanley, N. Almond and G. L. Smith, J. Gen. Virol. 71:2185–2190 (1990).
84. Boga, J. A., Marin, M. S., Casais, R., Prieto, M. and F. Parra, Virus Research. 26:33–40 (1992).
85. Boga, J. A., Casais, R., Marin, M. S., Martin-Alonso, J. M., Carmenes, R. S., Prieto, M. and F. Parra, J. Gen. Virol. 75:2409–2413 (1994).
86. Burroughs, J. N. and Brown, F., J. Gen. Virol. 22: 281–286 (1974).
87. Carter, M. J., Milton, I. D., Turner, P. C., Meanger, J., Bennett, M. and R. M. Gaskell, Arch. Virol. 122:223–235 (1992).
88. Chomczynski, P. and N. Sachi, Anal. Biochem.162: 156–159 (1987).
89. Cox, W. I., Tartaglia, J. and E. Paoletti, In Recombinant Poxviruses, M. M. Binns and G. L. Smith eds., (CRC Press) pp. 123–162 (1992).
90. David, E., Morisse, J. P., Nouaille, L. and M. P. Durand, Bull. Soc. Vet. de France, 75:385–395 (1991).
91. Huang, C. C, D. Nguyen, J. Fernandez, K. Y. Yun, K. E. Fry, D. W. Bradley, B. W. Tam and G. R. Reyes, Virology 191: 550–558 (1992).
92. Kapikian, A. Z. and R. M. Chanock, In Virology, 2nd ed. B. N. Fields and D. M. Knipe, eds., (Raven Press, Ltd., New-York) (1990).
93. Laurent, S., Vautherot, J. F., Madelaine, M. A., Le Gall, G. and D. Rasschaert, J. Virol. 68:6794–6798 (1994).
94. Meyers, G., Wirblich, C. and H. J. Thiel, Virology 184:664–676 (1991).

95. J. D. Neill, Virus Research, 24:211–222 (1992).
96. Parra, F., Boga, J. A., Marin, M. S. and R. Casais, Virus Research 27:219–228 (1993).
97. Perkus, M. E., Kauffman, E. B., Taylor, J., Mercer, S., Smith, D., Vanderhoeven, J. and E. Paoletti, J. Tiss. Cult. Meth. 15:72–81 (1993).
98. Pincus, S., Mason, P. W., Konishi, E., Fonseca, B. A., Shope, R., Rice, C. M. and E. Paoletti, Virology 187:290–297 (1992).
99. Prieto, M. and F. Parra, J. Virol. 64:4013–4015 (1990).
100. Sambrook, J., Fritsch, E. F. and T. Maniatis, A Laboratory Manual, Second edition (Cold Spring Harbor Laboratory Press) (1989.).
101. Seal, B. S., Ridpath, J. F. and W. L. Mengeling, J. Virol. 74:2519–2524 (1993).
102. Smid, B., Valicek, L., L. Rodak, Stepanek, J., Jurak, Vet. Microbiol. 26:77–85 (1991).
103. Studdert, M. J., Arch. Virol.58:157–191 (1978).
104. Tam, A. W., Smith, M. M., Guerra, M. E., Huang, C., Bradley, D. W., Fry, K. E. and G. R. Reyes, Virology 185:120–131 (1991).
105. Villares, A., Rev. Sci. Tech. Off. Int. Epizoot. 10:471–480 (1991).
106. von Haralambiev, H., Peschlejski, P., Jotov, M., Dimitrov, K., Vasilek, V. and P. Petkov, Tierarztl. Umschau. 46:155–158 (1991).
107. Wirblich, C., Meyers, G., Ohlinger, V. F., Capucci, L., Eskens, U., Haas, B. and H. J. Thiel, J. Virol. 68: 5164–5173 (1994).
Yu, G., Jiang, Y., Wan, Z., Zheng, J., Zhang, Y. and W. Guo, Int. Symp. on RHDV, Beijing China:376–379 (1991).

What is claimed is:

1. A recombinant poxvirus comprising exogenous coding DNA derived from calicivirus.

2. The poxvirus of claim 1 wherein said poxvirus is an avipox virus.

3. The poxvirus of claim 1 wherein the poxvirus is a vaccinia virus.

4. The poxvirus of claim 3 wherein at least one genetic function associated with virulence is inactivated by deleting at least one open reading frame.

5. The poxvirus of claim 4 wherein the deleted genetic functions include a C7L-K1L open reading frame, or, a host range region.

6. The poxvirus of claim 5 wherein at least one additional open reading frame is deleted; and, the additional open reading frame is selected from the group consisting of: J2R, B13R+B14R, A26L, A56R, and I4L.

7. The poxvirus of claim 5 wherein at least one additional region is deleted; and, the additional open reading frame is selected from the group consisting of: a thymidine kinase gene, a hemorrhagic region, an A type inclusion body region, a hemagglutinin gene, and a large subunit, ribonucleotide reductase.

8. The poxvirus of claim 6 wherein J2R, B13R+B14R, A26L, A56R, C7L–K1L and I4L are deleted from the virus.

9. The poxvirus of claim 7 wherein a thymidine kinase gene, a hemorrhagic region, an A type inclusion body region, a hemagglutinin gene, a host range region, and a large subunit, ribonucleotide reductase are deleted from the virus.

10. The poxvirus of claim 8 or 9 which is a NYVAC recombinant virus.

11. The poxvirus of claim 10 wherein the exogenous DNA is coding DNA derived from rabbit hemorrhagic disease virus.

12. The poxvirus of claim 11 wherein the exogenous DNA codes for a capsid protein.

13. A method for inducing an immunological response in a host to a calicivirus comprising: administering a recombinant Doxvirus as claimed in claim 1 containing exogenous DNA derived from calicivirus and coding for an antigen of calicivirus as a priming administration; and then subsequently administering an antigen derived from calicivirus.

14. The poxvirus of claim 2 wherein said poxvirus is a canarypox virus.

15. The poxvirus of claim 14 wherein the canarypox virus is a Rentschler vaccine strain which was attenuated through more than 200 serial passages on chick embryo fibroblasts, a master seed therefrom was subjected to four successive plaque purifications under agar, from which a plaque clone was amplified through five additional passages.

16. The pozvirus of claim 14 which is an ALVAC recombinant virus.

17. The poxvirus of claim 14 wherein the exogenous DNA is coding DNA derived from rabbit hemorrhagic disease virus.

18. The poxvirus of claim 17 wherein the exogenous DNA codes for a capsid protein.

19. A method of inducing an immunological response in a host comprising administering to said host a composition comprising a poxvirus as claimed in any one of claims 1, 2, 3, 8, 9, 14, 16 or 18 in admixture with a suitable carrier.

20. A composition for inducing an immunological response comprising a poxvirus as claimed in any one of claims 1, 2, 3, 8, 9, 14, 16 or 18 in admixture with a suitable carrier.

21. A method for expressing a gene product in a cell cultured in vitro comprising: introducing into the cell a virus as claimed in any one of claims 1, 2, 3, 8, 9, 14, 16 or 18, and continuing cell culture in vitro under appropriate conditions for expression of the gene product.

* * * * *